(12) United States Patent
Hartono et al.

(10) Patent No.: US 11,628,265 B2
(45) Date of Patent: Apr. 18, 2023

(54) SEAL-FORMING STRUCTURE, POSITIONING AND STABILIZING STRUCTURE AND DIFFUSER VENT FOR PATIENT INTERFACE

(71) Applicant: RESMED PTY LTD, Bella Vista (AU)

(72) Inventors: Marvin Sugi Hartono, Singapore (SG); Michael Kenneth Truscott, Sydney (AU); Craig David Edwards, Sydney (AU); Chuan Foong Lee, Johor (MY); Min Li Tee, Singapore (SG); Shannon Day, Sydney (AU); Nigel Paul Greig, Sydney (AU); Christopher Daniel Parker, Sydney (AU); Angelene Marie Ozolins, Sydney (AU); Jessica Lea Dunn, Sydney (AU); Bishavjot Singh, Sydney (AU); Vinay Manjunath, Sydney (AU); Chee Keong Ong, Singapore (SG); Lorenz Eberl, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/310,284

(22) PCT Filed: Apr. 7, 2020

(86) PCT No.: PCT/IB2020/053311
§ 371 (c)(1),
(2) Date: Jul. 27, 2021

(87) PCT Pub. No.: WO2020/208523
PCT Pub. Date: Oct. 15, 2020

(65) Prior Publication Data
US 2022/0134039 A1 May 5, 2022

Related U.S. Application Data

(60) Provisional application No. 62/830,764, filed on Apr. 8, 2019, provisional application No. 62/830,745, filed on Apr. 8, 2019.

(51) Int. Cl.
*A61M 16/06* (2006.01)
*A61M 16/10* (2006.01)

(52) U.S. Cl.
CPC .... *A61M 16/0622* (2014.02); *A61M 16/0683* (2013.01); *A61M 16/1065* (2014.02);
(Continued)

(58) Field of Classification Search
CPC .......... A61M 16/0057; A61M 16/0066; A61M 16/06; A61M 16/0616; A61M 16/0622;
(Continued)

(56) References Cited

U.S. PATENT DOCUMENTS 2,939,458 A * 6/1960 Lundquist ............ A62B 18/025
128/206.25
4,782,832 A 11/1988 Trimble et al.
(Continued)

FOREIGN PATENT DOCUMENTS

JP 2016-538049 A 12/2016
NZ 585826 A 11/2011
(Continued)

OTHER PUBLICATIONS

"*Respiratory Physiology*", by John B. West, Lippincott Williams & Wilkins, 9th edition published 2012 (8 pages).
(Continued)

*Primary Examiner* — Annette Dixon
(74) *Attorney, Agent, or Firm* — Nixon & Vanderhye P.C.

(57) ABSTRACT

A patient interface to deliver a flow of air at a positive pressure with respect to ambient air pressure to an entrance to the patient's airways to ameliorate sleep disordered breathing includes a frame assembly and a cushion assembly configured to removably and repeatably connect to the frame assembly. The frame assembly and the cushion assembly form at least part of a plenum chamber pressurizable to a (Continued)

therapeutic pressure. The cushion assembly comprises a one-piece construction including a seal-forming structure configured to form a seal with a region of a patients face surrounding the entrance to the patients airways and a frame connection structure configured to removably and repeatably connect the cushion assembly to the frame assembly. The seal-forming structure comprises a first elastomeric material and the frame connection structure comprises a second elastomeric material, the first elastomeric material comprising a lower durometer or hardness than the second elastomeric material.

20 Claims, 67 Drawing Sheets

(52) U.S. Cl.
CPC ............... *A61M 2202/0225* (2013.01); *A61M 2205/0216* (2013.01); *A61M 2205/42* (2013.01); *A61M 2210/0618* (2013.01)

(58) Field of Classification Search
CPC .......... A61M 16/0633; A61M 16/0644; A61M 16/0666; A61M 16/0683; A61M 16/0694; A61M 16/0816; A61M 16/0825; A61M 16/0875; A61M 2016/0661; A61M 2205/0216; A61M 2205/0266; A61M 2206/14; A61M 2210/0618; A62B 18/084; Y10S 24/48
See application file for complete search history.

(56) References Cited

U.S. PATENT DOCUMENTS

| | | | |
|---|---|---|---|
| 4,944,310 A | 7/1990 | Sullivan | |
| 6,467,483 B1* | 10/2002 | Kopacko | A61M 16/06 128/912 |
| 6,532,959 B1 | 3/2003 | Berthon-Jones | |
| 6,581,594 B1 | 6/2003 | Drew et al. | |
| 6,662,803 B2 | 12/2003 | Gradon et al. | |
| 7,237,551 B2* | 7/2007 | Ho | A61M 16/0616 128/206.26 |
| 7,287,528 B2* | 10/2007 | Ho | A61M 16/0616 128/206.24 |
| 7,866,944 B2 | 1/2011 | Kenyon et al. | |
| 8,146,595 B2* | 4/2012 | Sherman | A61M 16/06 24/DIG. 48 |
| 8,397,727 B2 | 3/2013 | Ng et al. | |
| 8,636,479 B2 | 1/2014 | Kenyon et al. | |
| 8,638,014 B2 | 1/2014 | Sears et al. | |
| 8,684,004 B2* | 4/2014 | Eifler | A61M 16/0633 128/200.24 |
| 8,733,349 B2 | 5/2014 | Bath et al. | |
| 9,010,331 B2* | 4/2015 | Lang | A61M 16/0616 425/588 |
| 2003/0019495 A1* | 1/2003 | Palkon | A61M 16/06 128/206.24 |
| 2003/0196658 A1* | 10/2003 | Ging | A61M 16/0683 128/201.22 |
| 2004/0182398 A1* | 9/2004 | Sprinkle | A61M 16/0638 128/207.13 |
| 2005/0199239 A1* | 9/2005 | Lang | A61M 16/0605 128/206.24 |
| 2006/0096598 A1* | 5/2006 | Ho | A61M 16/0616 128/206.24 |
| 2006/0144399 A1* | 7/2006 | Davidowski | A61M 16/06 128/205.12 |
| 2008/0047559 A1* | 2/2008 | Fiori | A61M 16/0666 128/207.18 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0294281 A1* | 11/2010 | Ho | A61M 16/0633 128/206.24 |
| 2012/0138061 A1* | 6/2012 | Dravitzki | A61M 16/06 128/205.25 |
| 2013/0213402 A1 | 8/2013 | D'Souza et al. | |
| 2015/0314099 A1 | 11/2015 | Carroll et al. | |
| 2016/0074611 A1* | 3/2016 | Higgins | A61M 16/06 128/206.24 |
| 2016/0367778 A1 | 12/2016 | Eves et al. | |
| 2017/0021121 A1 | 1/2017 | Guney et al. | |
| 2017/0281894 A1 | 10/2017 | Walls et al. | |
| 2017/0281898 A1 | 10/2017 | Dantanarayana | |
| 2018/0140795 A1 | 5/2018 | Wells et al. | |
| 2018/0185598 A1 | 7/2018 | Olsen et al. | |
| 2018/0236200 A1 | 8/2018 | Goldspink et al. | |
| 2018/0289916 A1 | 10/2018 | Gunaratnam et al. | |
| 2020/0306503 A1* | 10/2020 | Prescher | A61M 1/0062 |

FOREIGN PATENT DOCUMENTS

| | | |
|---|---|---|
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2014/110626 A1 | 7/2014 |
| WO | WO 2018/053589 A1 | 3/2018 |
| WO | WO 2020/037359 A1 | 2/2020 |

OTHER PUBLICATIONS

International Search Report dated Jul. 17, 2020 in International Application No. PCT/IB2020/053311, 7 pages.
Written Opinion of the International Searching Authority dated Jul. 17, 2020 in International Application No. PCT/IB2020/053311, 8 pages.
Notice of Reasons for Rejection dated May 9, 2022 in Japanese Application No. 2021-559669, with English translation, 13 pages.
Notice of Submission of Opinion dated May 27, 2022 in Korean Application No. 10-2021-7034035, with English translation, 16 pages.

* cited by examiner

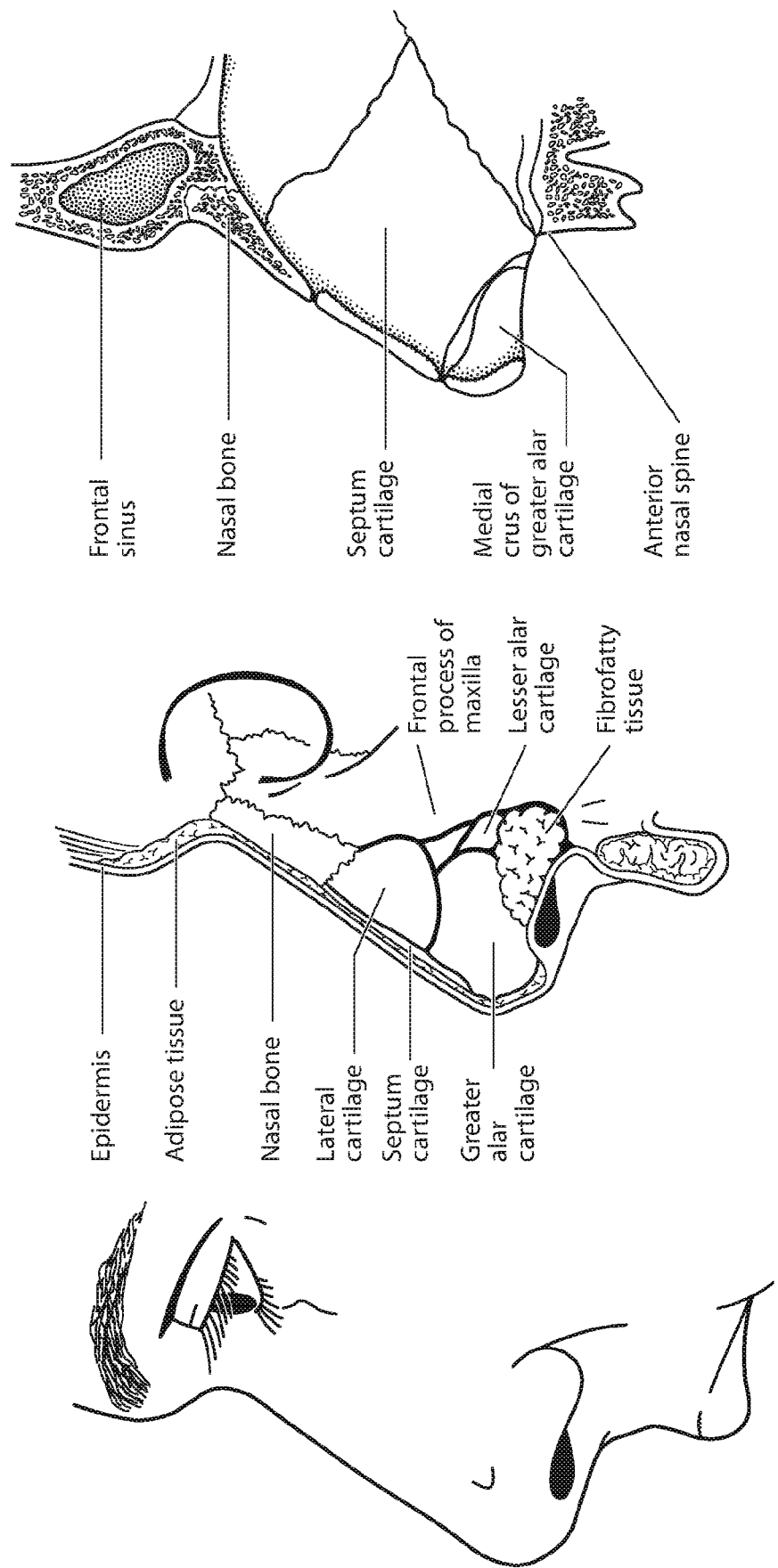

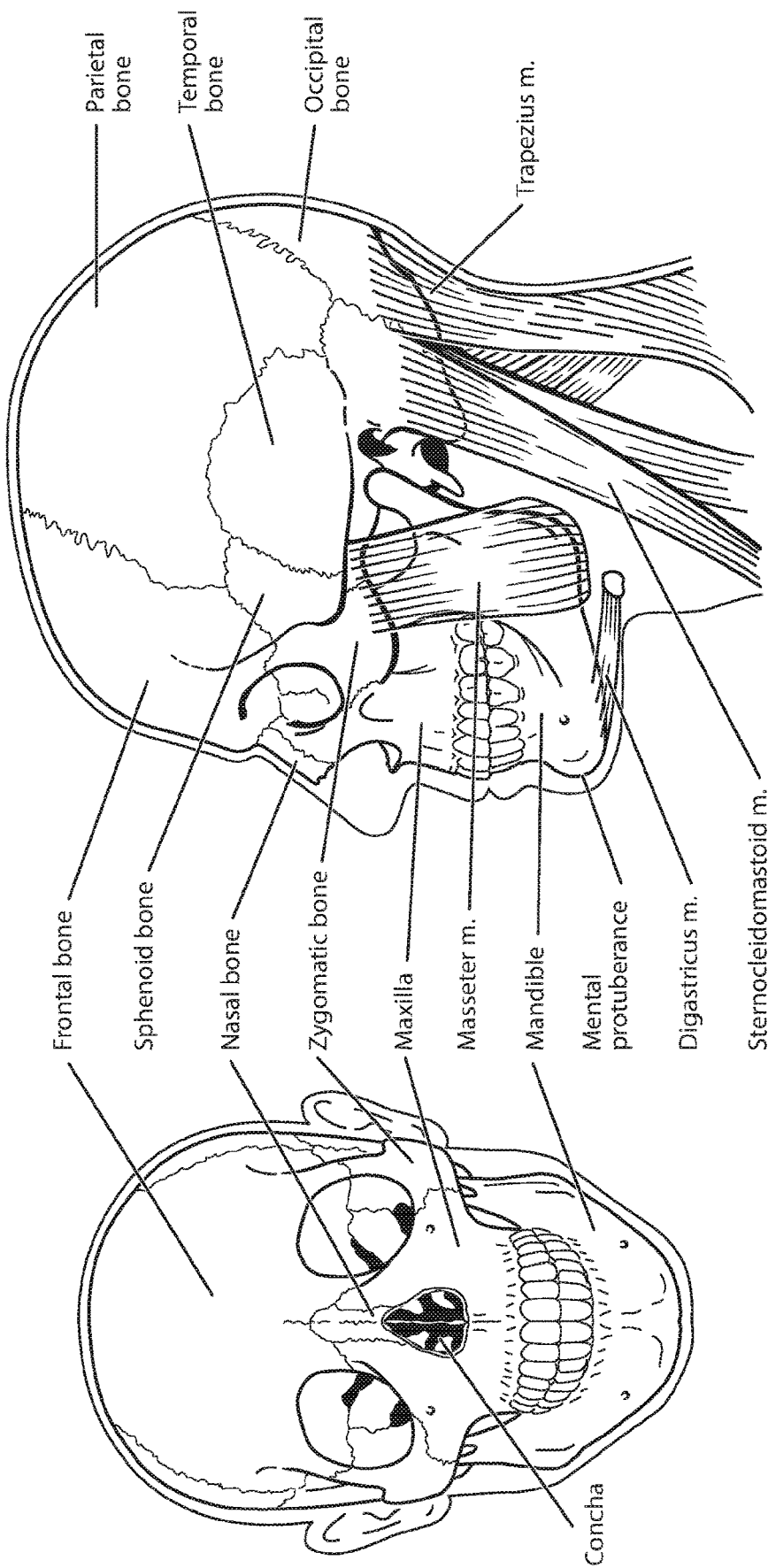

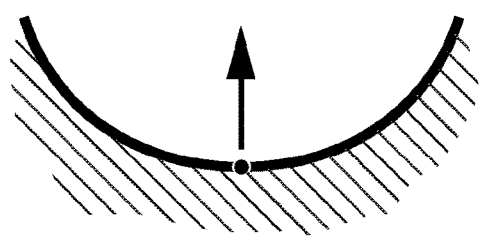
FIG. 3B — Relatively Large Positive Curvature
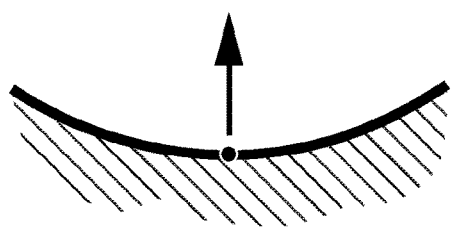
FIG. 3C — Relatively Small Positive Curvature
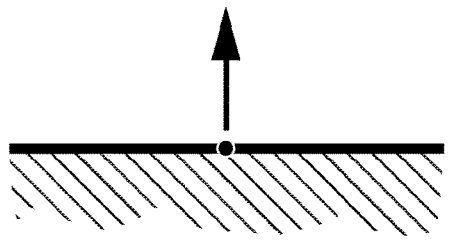
FIG. 3D — Zero Curvature
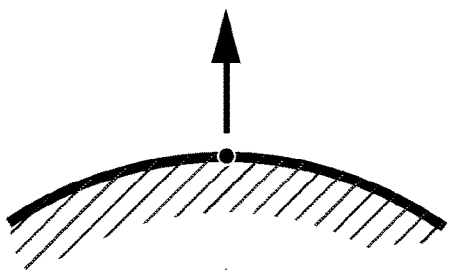
FIG. 3E — Relatively Small Negative Curvature
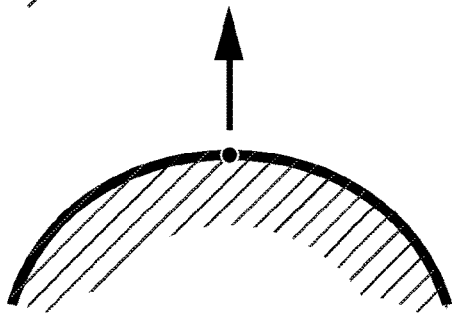
FIG. 3F — Relatively Large Negative Curvature
Copyright 2015 ResMed Limited

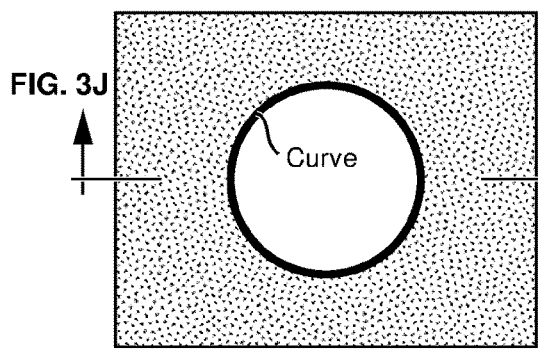
FIG. 3I
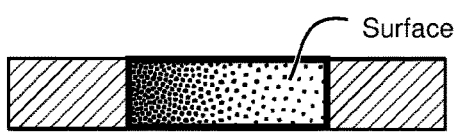
FIG. 3J
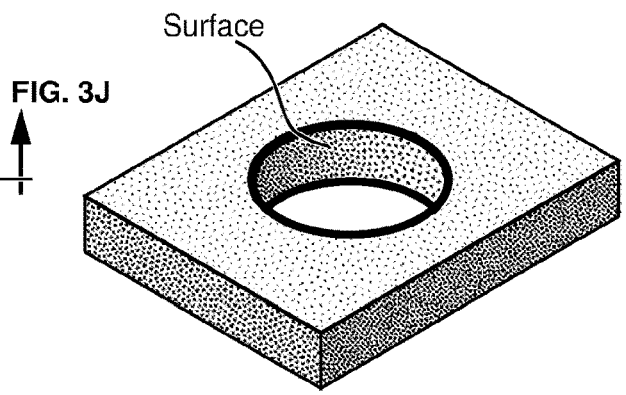
FIG. 3K
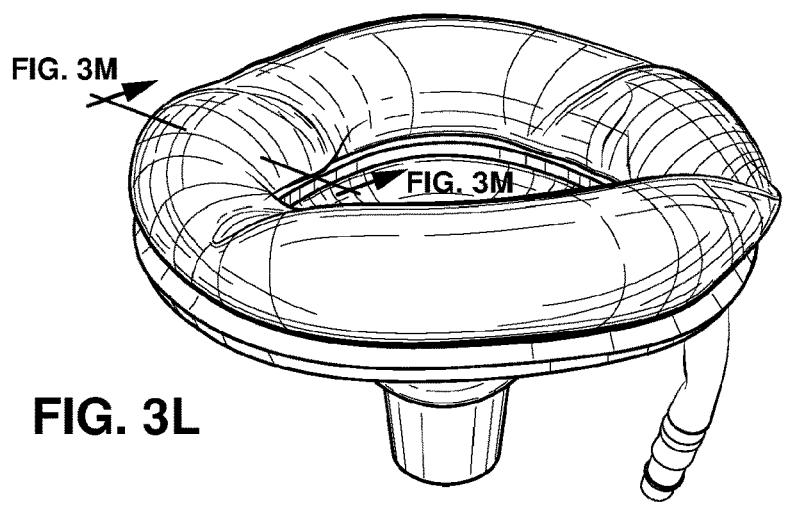
FIG. 3L
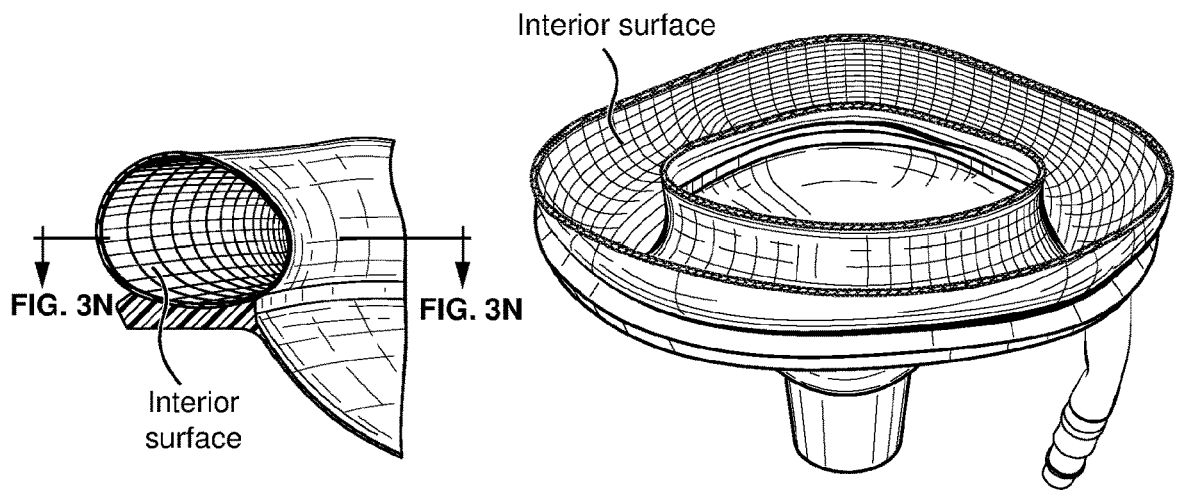
FIG. 3M  FIG. 3N

Left-hand rule

Right-hand rule

Left ear helix

Right-hand helix
Right-hand positive

Right ear helix

Copyright 2015 ResMed Limited

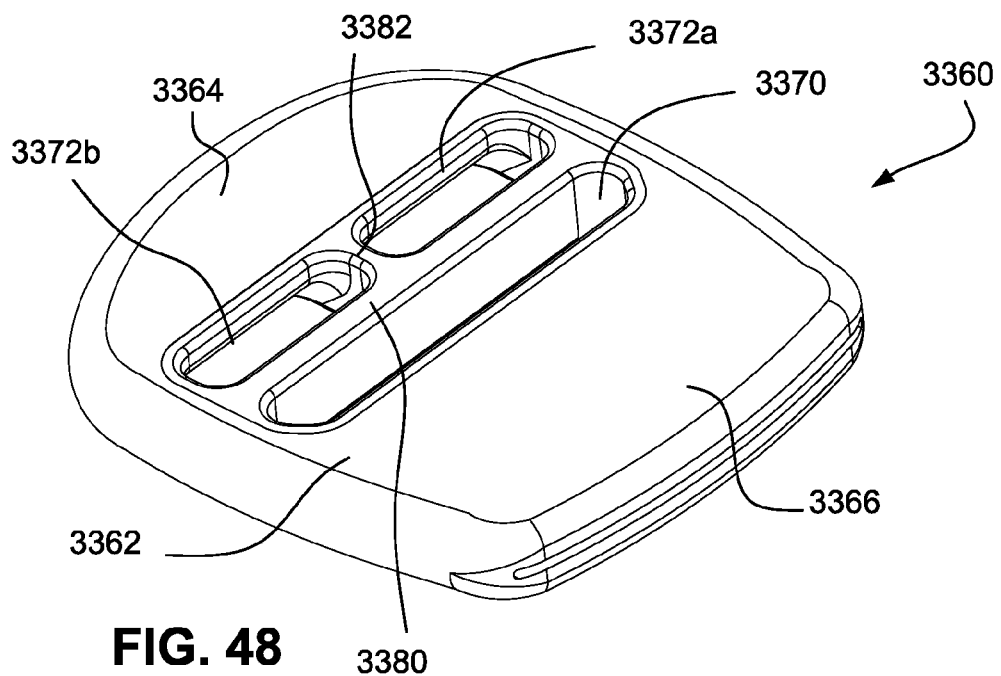
FIG. 48
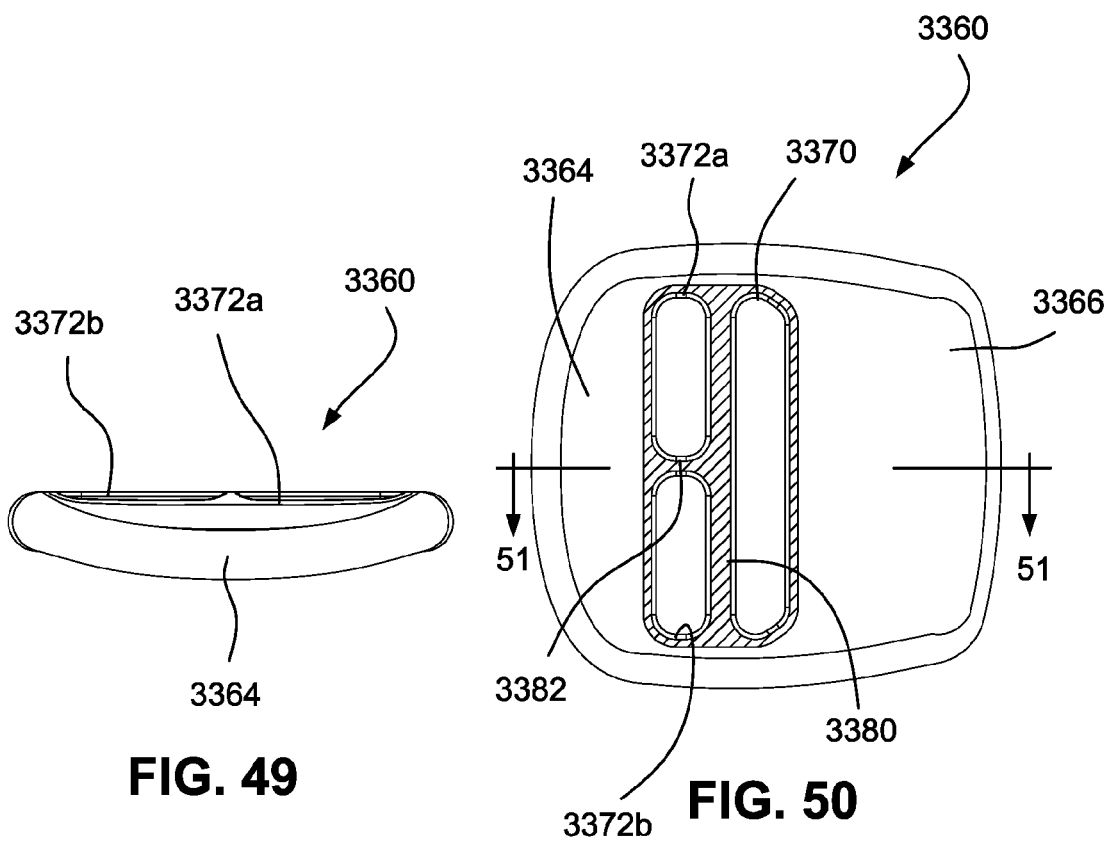
FIG. 49
FIG. 50

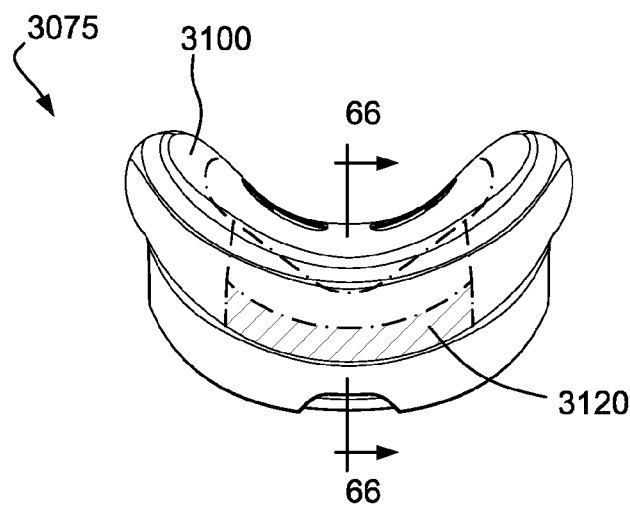
FIG. 62
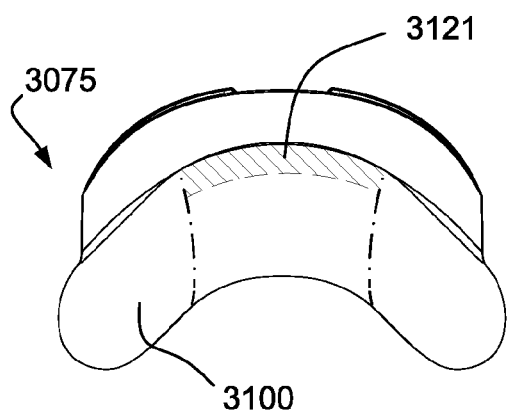
FIG. 63
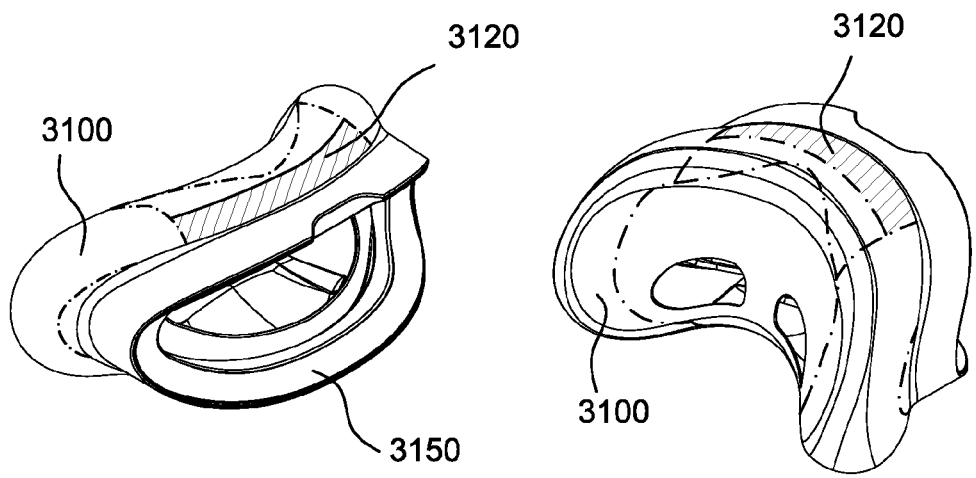
FIG. 64
FIG. 65

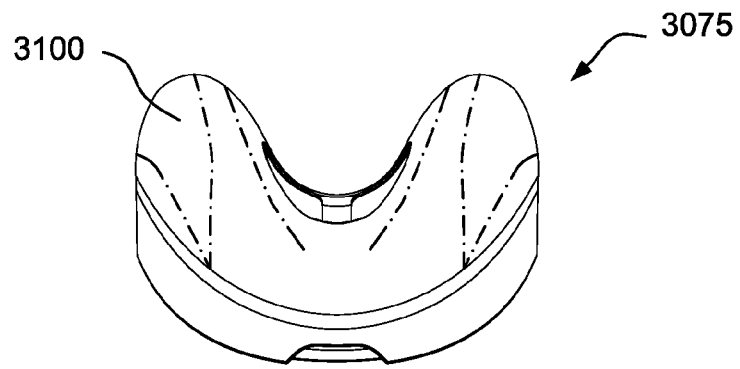
FIG. 68
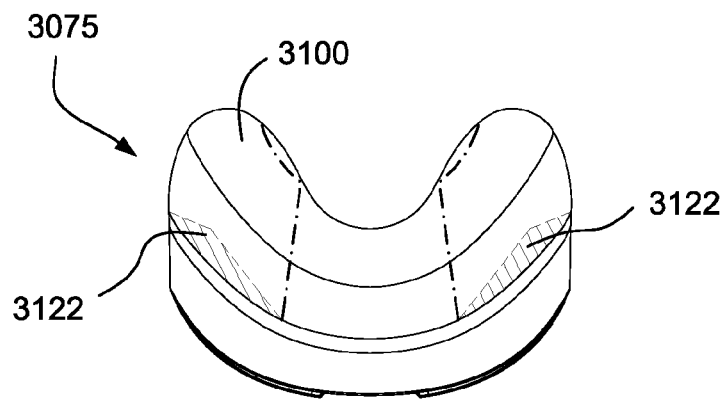
FIG. 69
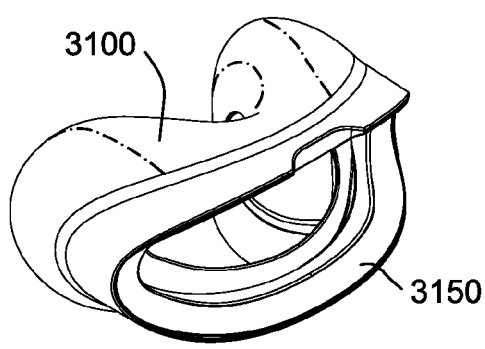 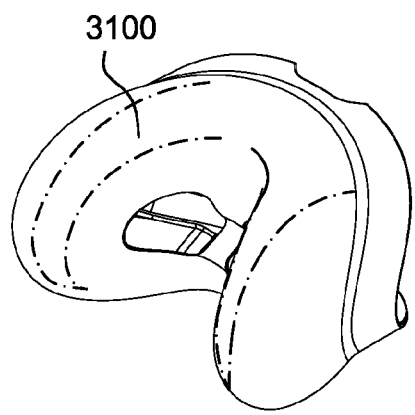
FIG. 70  FIG. 71

SEAL-FORMING STRUCTURE, POSITIONING AND STABILIZING STRUCTURE AND DIFFUSER VENT FOR PATIENT INTERFACE

1. CROSS-REFERENCE TO RELATED APPLICATIONS

This application is the U.S. national phase of International Application No. PCT/IB2020/053311 filed Apr. 7, 2020 which designated the U.S. and claims priority to U.S. Provisional Application No. 62/830,745 filed Apr. 8, 2019 and U.S. Provisional Application No. 62/830,764 filed Apr. 8, 2019, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2. BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "Respiratory Physiology", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

(*) one specimen only, measured using test method specified in ISO 3744 in CPAP mode at 10 cm H₂O Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

Another aspect of the present technology is directed to a patient interface that may comprise: a plenum chamber; a seal-forming structure; and a positioning and stabilising structure. The patient interface may further comprise a vent structure. The patient interface may further be configured to leave the patient's mouth uncovered, or if the seal-forming structure is configured to seal around the patient's nose and mouth, the patient interface may be further configured to allow the patient to breath from ambient in the absence of a flow of pressurised air through the plenum chamber inlet port.

Another aspect of the present technology is directed to a patient interface comprising: a plenum chamber pressurisable to a therapeutic pressure of at least 4 cmH2O above ambient air pressure, said plenum chamber including a plenum chamber inlet port sized and structured to receive a flow of air at the therapeutic pressure for breathing by a patient; a seal-forming structure constructed and arranged to seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; a positioning and stabilising structure configured to hold the seal-forming structure in a therapeutically effective position on the patient's head, the positioning and stabilising structure comprising a tie, the tie being constructed and arranged so that at least a portion overlies a region of the patient's head superior to an otobasion superior of the patient's head in use; and a vent structure configured to allow a continuous flow of gases exhaled by the patient from an interior of the plenum chamber to ambient, said vent structure being sized and shaped to maintain the therapeutic pressure in the plenum chamber in use; wherein the patient interface is configured to leave the patient's mouth uncovered, or if the seal-forming structure is configured to seal around the patient's nose and mouth, the patient interface is configured to allow the patient to breath from ambient in the absence of a flow of pressurised air through the plenum chamber inlet port.

An aspect of the present technology relates to a patient interface including a frame assembly and a cushion assembly configured to removably and repeatably connect to the frame assembly. The cushion assembly comprises a one-piece construction including a seal-forming structure constructed and arranged to form a seal with a region of a patient's face surrounding the entrance to the patient's airways and a frame connection structure constructed and arranged to removably and repeatably connect the cushion assembly to the frame assembly. The seal-forming structure comprises a first elastomeric material and the frame connection structure comprise a second elastomeric material, wherein the first elastomeric material comprises a lower durometer or hardness than the second elastomeric material.

In an example, each of the first elastomeric material and the second elastomeric material may comprise a TPE or silicone material.

An aspect of the present technology relates to a patient interface to deliver a flow of air at a positive pressure with respect to ambient air pressure to an entrance to the patient's airways including at least the entrance of a patient's nares while the patient is sleeping, to ameliorate sleep disordered breathing. The patient interface includes a frame assembly and a cushion assembly configured to removably and repeatably connect to the frame assembly. The frame assembly and the cushion assembly form at least part of a plenum chamber pressurizable to a therapeutic pressure. The cushion assembly comprises a one-piece construction including a seal-forming structure constructed and arranged to form a seal with a region of a patient's face surrounding the entrance to the patient's airways and a frame connection structure constructed and arranged to removably and repeatably connect the cushion assembly to the frame assembly. The seal-forming structure comprises a first elastomeric material and the frame connection structure comprise a second elastomeric material, wherein the first elastomeric material comprises a lower durometer or hardness than the second elastomeric material. The frame connection structure comprises an undercut that acts as an interface or catch adapted to connect to the frame assembly. The frame connection structure is arranged along an interior surface or interior periphery of the seal-forming structure such that the frame connection structure and the undercut thereof is arranged or oriented towards an interior of the cushion assembly that forms at least a portion of the plenum chamber.

In an example, the seal-forming structure may comprise a nasal cradle cushion adapted to from a seal against at least an underside of the patient's nose. In an example, the seal-forming structure and the frame connection structure may comprise an overmolded construction to form a one-piece integrated component. In an example, the frame connection structure may comprise a base mold and the seal-forming structure may comprise an overmold provided to the base mold. In an example, each of the first elastomeric material and the second elastomeric material may comprise a TPE or silicone material. In an example, the frame connection structure may comprise one or more interfacing surfaces structured to bond with the seal-forming structure. In an example, the first elastomeric material may comprise a durometer in the range of 30-50 Shore A and the second elastomeric material may comprise a durometer in the range of 60-90 Shore A. In an example, the patient interface may further comprise a sealing lip provided to the seal-forming structure of the first elastomeric material, the sealing lip constructed and arranged to form a seal with the frame assembly. In an example, the frame assembly may be relatively harder than the frame connection structure. In an example, the frame connection structure and the undercut thereof may extend around the entire perimeter or interior periphery of the seal-forming structure.

Another aspect of the present technology relates to a patient interface including a positioning and stabilising structure to provide a force to hold a seal-forming structure in a therapeutically effective position on a patient's head. The positioning and stabilizing structure includes a first strap comprising an elastic material, a second strap comprising an elastic material, and a buckle constructed and arranged to connect the first strap to the second strap and permit length adjustment in addition to length adjustment provided by the elasticity of the first and second straps.

Another aspect of the present technology relates to a patient interface to deliver a flow of air at a positive pressure with respect to ambient air pressure to an entrance to the patient's airways including at least the entrance of a patient's nares while the patient is sleeping, to ameliorate sleep disordered breathing. The patient interface includes a seal-forming structure constructed and arranged to form a seal with a region of a patient's face surrounding the entrance to the patient's airways and a positioning and stabilising structure to provide a force to hold the seal-forming structure in a therapeutically effective position on a patient's head. The positioning and stabilizing structure includes a first strap comprising an elastic, textile material, a second strap comprising an elastic, textile material, and a buckle constructed and arranged to connect the first strap to the second strap and permit length adjustment in addition to length adjustment provided by the elasticity of the first and second straps. The first strap includes a side strap portion that bifurcates into two back strap portions. The second strap includes a side strap portion. The side strap portion of the second strap includes an end that is non-adjustably connected to the buckle, and the two back strap portions of the first strap are threaded through the buckle to adjustably connect the first strap to the buckle and permit the length adjustment. The buckle includes a first opening and a pair of second openings, and the buckle includes a cross-bar that delineates the first opening from the pair of second openings. The two back strap portions of the first strap are threaded through the first opening, around the cross-bar, and through respective ones of the pair of second openings to adjustably connect the two back strap portions of the first strap to the buckle. The side strap portions of respective first and second straps are adapted to extend along the sides of the patient's head and the two back strap portions of the first strap are adapted to extend along the back of the patient's head.

In an example, the first strap may be longer than the second strap in its original length in a neutral, non-stretched state. In an example, one of the two back strap portions may be adapted to be positioned superior to the patient's occipital lobe and the other of the two back strap portions may be adapted to be positioned inferior to the patient's occipital lobe. In an example, the buckle may include a first end portion and a second end portion, the second end portion being connected to the end of the side strap portion of the second strap, and the first end portion may be curved or angled upwardly relative to the second end portion. In an example, each of the pair of second openings may include an angled edge or surface arranged to resist adjustment in use. In an example, the buckle may comprise a locked position when the buckle extends generally parallel to the two back strap portions to resist unintentional adjustment due to friction between the two back strap portions and the angled edge or surface in respective second openings, and the buckle may comprise an unlocked position when lifted or pivoted so that the buckle extends transverse to the two back strap portions to allow adjustment due to reduced friction between the two back strap portions and the angled edge or surface in respective second openings. In an example, the positioning and stabilizing structure may further comprise a pair of rigidizer arms, and the side strap portions of the first and second straps are provided to respective ones of the pair of rigidizer arms. In an example, each side strap portion may include a tube-like configuration adapted to receive a respective one of the rigidizer arms. In an example, each end of the first strap may include a reinforcement portion, and the second strap may include an opposite end, opposite to the end connected to the buckle, that includes a reinforcement portion, each reinforcement portion comprising a different material than the first and second straps.

An aspect of the present technology relates to a patient interface including a vent structured and arranged to improve diffusivity in air flow so as to minimize noise in use.

An aspect of the present technology relates to a patient interface including a vent with flow dividers to divide vent flow.

An aspect of the present technology relates to a patient interface including a vent with diffusing member(s) to diffuse vent flow and flow dividers to divide vent flow into spaced and separated vent flow paths around a perimeter of the patient interface.

An aspect of the present technology relates to a patient interface to deliver a flow of air at a positive pressure with respect to ambient air pressure to an entrance to the patient's airways including at least the entrance of a patient's nares while the patient is sleeping, to ameliorate sleep disordered breathing. The patient interface includes a seal-forming structure constructed and arranged to form a seal with a region of a patient's face surrounding the entrance to the patient's airways, the seal-forming structure forming at least a portion of a plenum chamber pressurizable to a therapeutic pressure and a vent assembly configured to provide a vent flow of gas to discharge gas exhaled by the patient from the plenum chamber to ambient. The vent assembly includes a main body including a plurality of orifices extending through the main body to allow gas to be discharged from the plenum chamber to ambient, a diffusing member configured and arranged such that the plurality of orifices are covered by the diffusing member so that the vent flow of gas passes through the diffusing member, and a plurality of ribs. The plurality of ribs are configured and arranged to support the diffusing member in spaced relation from an outlet end of each of the plurality of orifices and divide the vent flow of gas into spaced and separated vent flow paths downstream from the diffusing member around a perimeter of the main body.

In an example, the diffusing member may comprise a filter material. In an example, the plurality of orifices may be arranged in an arc or U-shape. In an example, the plurality of ribs may be arranged along an outer periphery of the plurality of orifices to support an outer edge of the diffusing member. In an example, the vent assembly may further comprise a spacer provided to the main body, the spacer arranged along an inner periphery of the plurality of orifices to support the diffusing member. In an example, the patient interface may further comprise a cover to retain the diffusing member to the main body. In an example, the main body and the cover may form a diffusion section including a diffusion section inlet and a diffusion section outlet, and the plurality of ribs are disposed within the diffusion section between the diffusion section inlet and the diffusion section outlet to divide the vent flow of gas. In an example, the diffusion section inlet of the diffusion section may be provided by an outlet end of each of the plurality of orifices. In an example, the plurality of ribs and the diffusing member may be provided within a recessed region of the main body, and the diffusion section outlet of the diffusion section may be provided by a gap formed between the cover and a periphery of the recessed region. In an example, the diffusion section outlet may be spaced radially outwardly of the diffusion section inlet. In an example, the plurality of ribs may be constructed and arranged to divide turbulent kinetic energy at the diffusion section inlet into segments towards the diffusion section outlet. In an example, the plurality of ribs may be constructed and arranged to divide the turbulent kinetic energy into substantially equal segments. In an example, one or more of the plurality of ribs may be provided to the cover. In an example, one or more of the plurality of ribs may comprise a one-piece construction with the cover. In an example, each of the plurality of ribs may extend in a generally orthogonal direction to a major face of the main body. In an example, the plurality of orifices may comprise a first multi-hole vent arrangement, and the vent assembly may further comprise a second multi-hole vent arrangement spaced apart from the first multi-hole vent arrangement, the second multi-hole vent arrangement including plurality of orifices extending through the main body. In an example, the vent assembly may further comprise a second diffusing member configured and arranged to cover the plurality of orifices of the second multi-hole vent arrangement, and the plurality of ribs may comprise ribs configured and arranged to support the second diffusing member. In an example, the patient interface may further comprise a frame assembly, and the seal-forming structure is provided to the frame assembly. In an example, the main body of the vent assembly may be provided by the frame assembly. In an example, the frame assembly may comprise a connection port adapted to connect to an air delivery conduit. In an example, the plurality of orifices may be configured and arranged to prevent cross flow. In an example, one or more of the plurality of ribs may be provided to the main body. In an example, one or more of the plurality of ribs may comprise a one-piece construction with the main body.

An aspect of the present technology relates to a patient interface to deliver a flow of air at a positive pressure with respect to ambient air pressure to an entrance to the patient's airways including at least the entrance of a patient's nares while the patient is sleeping, to ameliorate sleep disordered breathing. The patient interface includes a seal-forming structure constructed and arranged to form a seal with a region of a patient's face surrounding the entrance to the patient's airways, the seal-forming structure forming at least a portion of a plenum chamber pressurizable to a therapeutic pressure and a vent configured to provide a vent flow of gas to discharge gas exhaled by the patient from the plenum chamber to ambient. The vent comprises a main body including a plurality of orifices extending through the main body to allow gas to be discharged from the plenum chamber to ambient. The main body includes at least one ridge or rib providing a surface area, and an outlet end of each of the plurality of orifices is arranged along the surface area.

In an example, the main body may include a plurality of ridges or ribs providing spaced-apart surface areas, and the outlet end of each of the plurality of orifices may be arranged along a respective one of the spaced-apart surface areas. In an example, the plurality of ridges or ribs may be arranged to provide a stepped arrangement of surface areas. In an example, the spaced-apart surface areas may be generally parallel to one another. In an example, the plurality of orifices may be arranged in columns, and each of the columns may be arranged along a respective one of the spaced-apart surface areas. In an example, the plurality of orifices may comprise a first multi-hole vent arrangement, and the vent may further comprise a second multi-hole vent arrangement spaced apart from the first multi-hole vent arrangement, the second multi-hole vent arrangement may include plurality of orifices extending through the main body. In an example, the patient interface may further comprise a frame assembly, and the seal-forming structure may be provided to the frame assembly. In an example, the main body of the vent may be provided by the frame assembly.

An aspect of the present technology relates to a CPAP system for providing gas at positive pressure for respiratory therapy to a patient, the CPAP system including an RPT device configured to supply a flow of gas at a therapeutic pressure, a patient interface, and an air delivery conduit configured to pass a flow of gas at therapeutic pressure from the RPT device to the patient interface.

Another aspect of one form of the present technology is a patient interface that is moulded or otherwise constructed with a perimeter shape which is complementary to that of an intended wearer.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
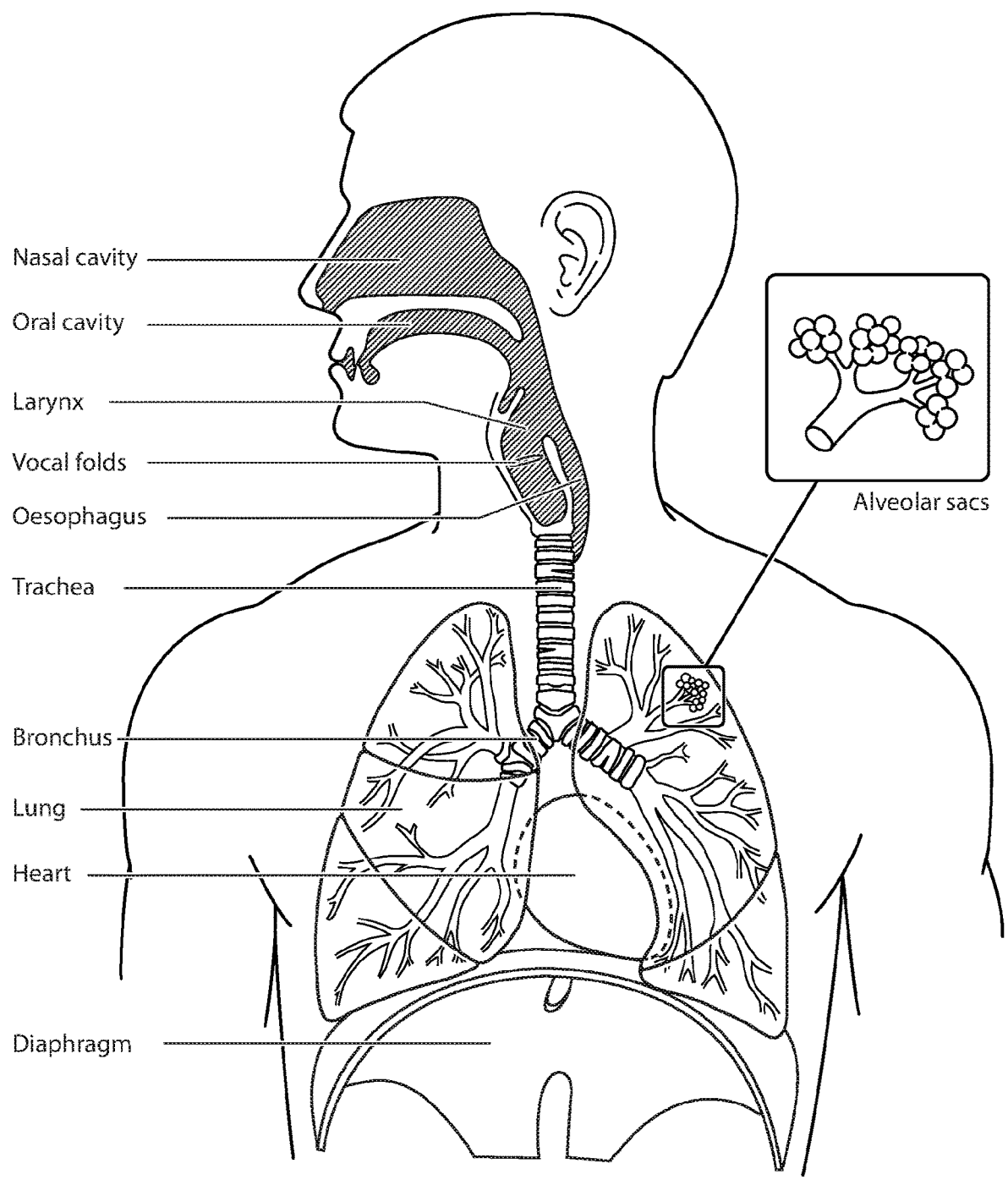
FIG. 2A shows an overview of a human respiratory system including the nasal and oral cavities, the larynx, vocal folds, oesophagus, trachea, bronchus, lung, alveolar sacs, heart and diaphragm.
Figure 2B:
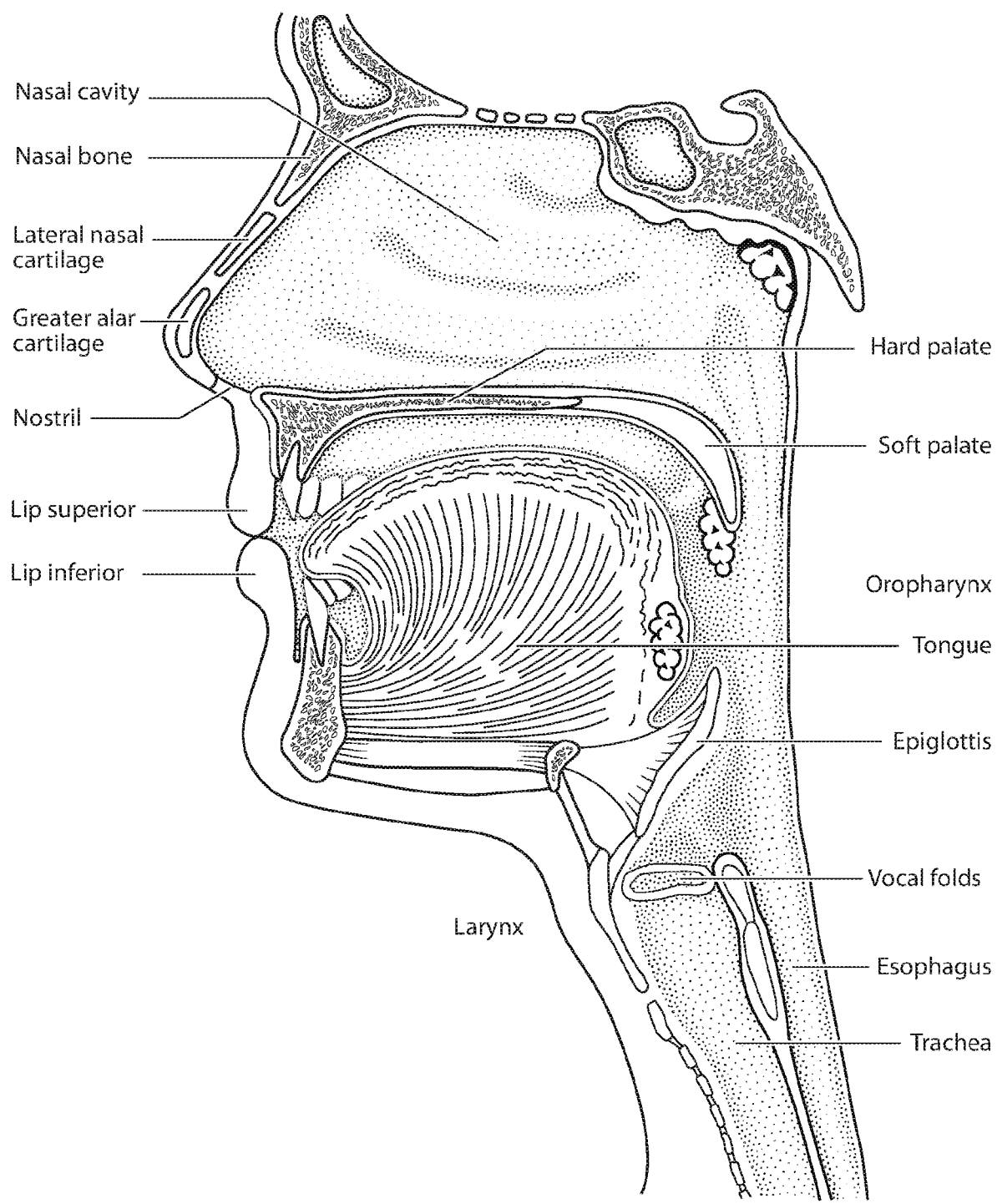
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
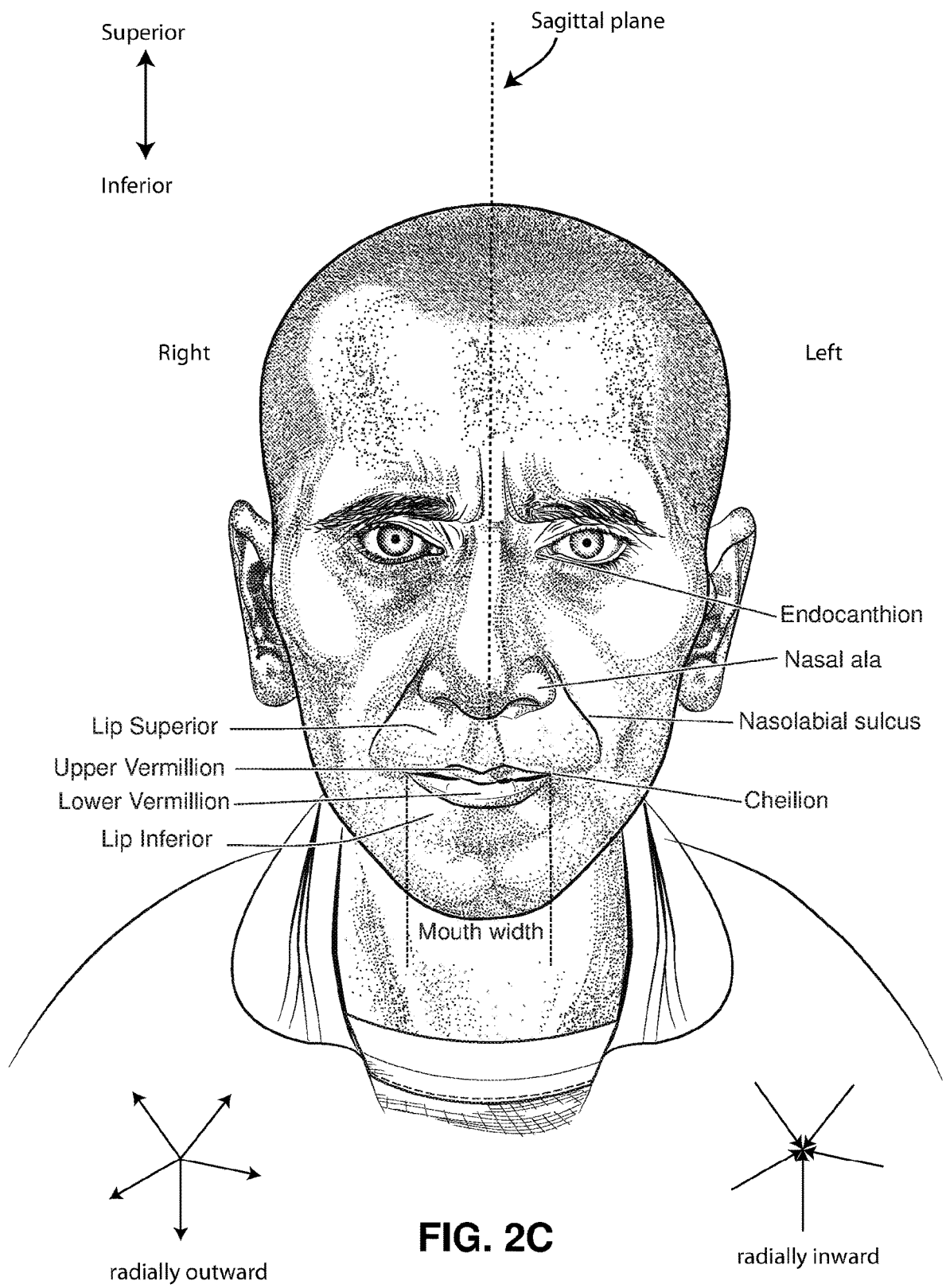
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
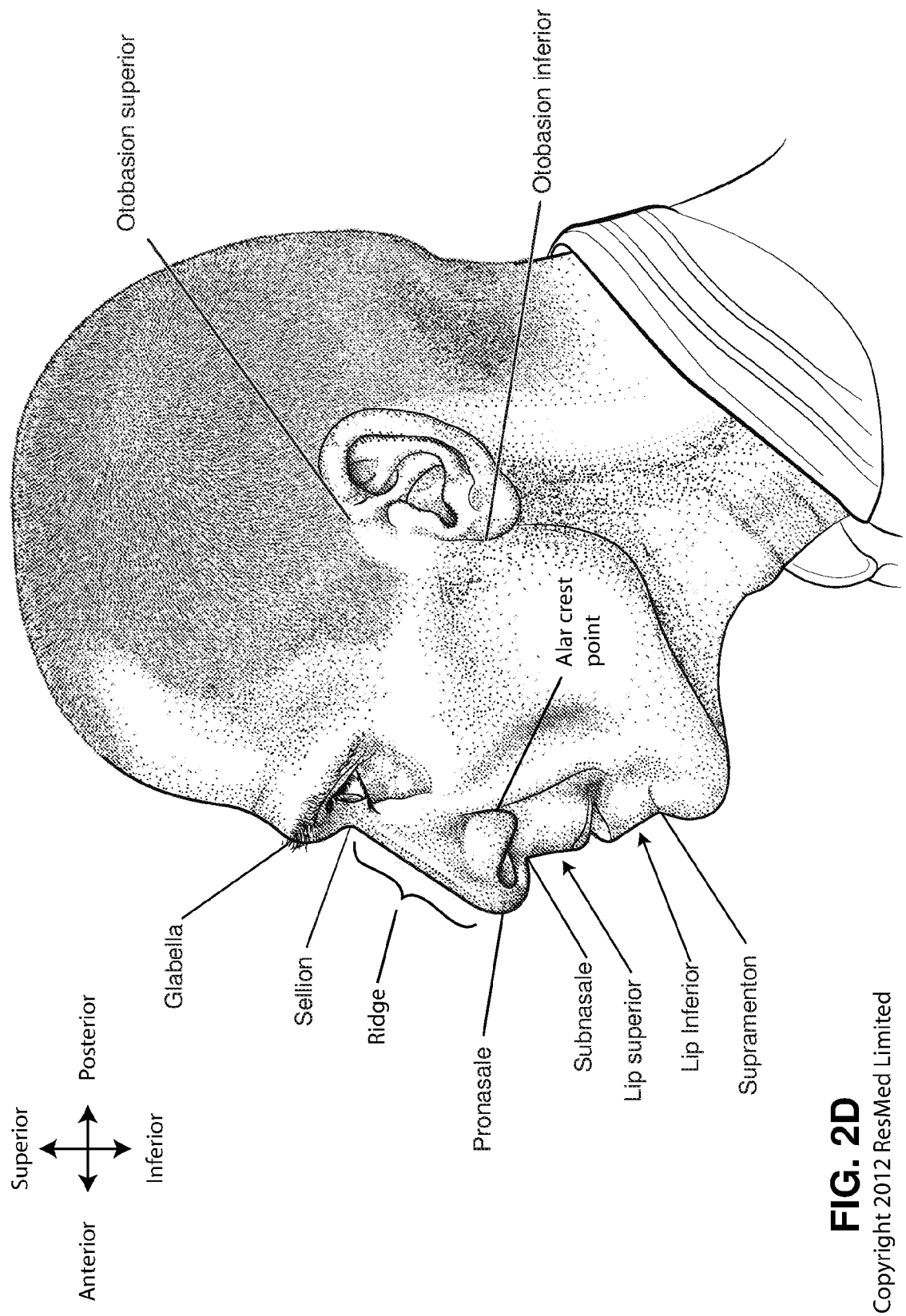
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
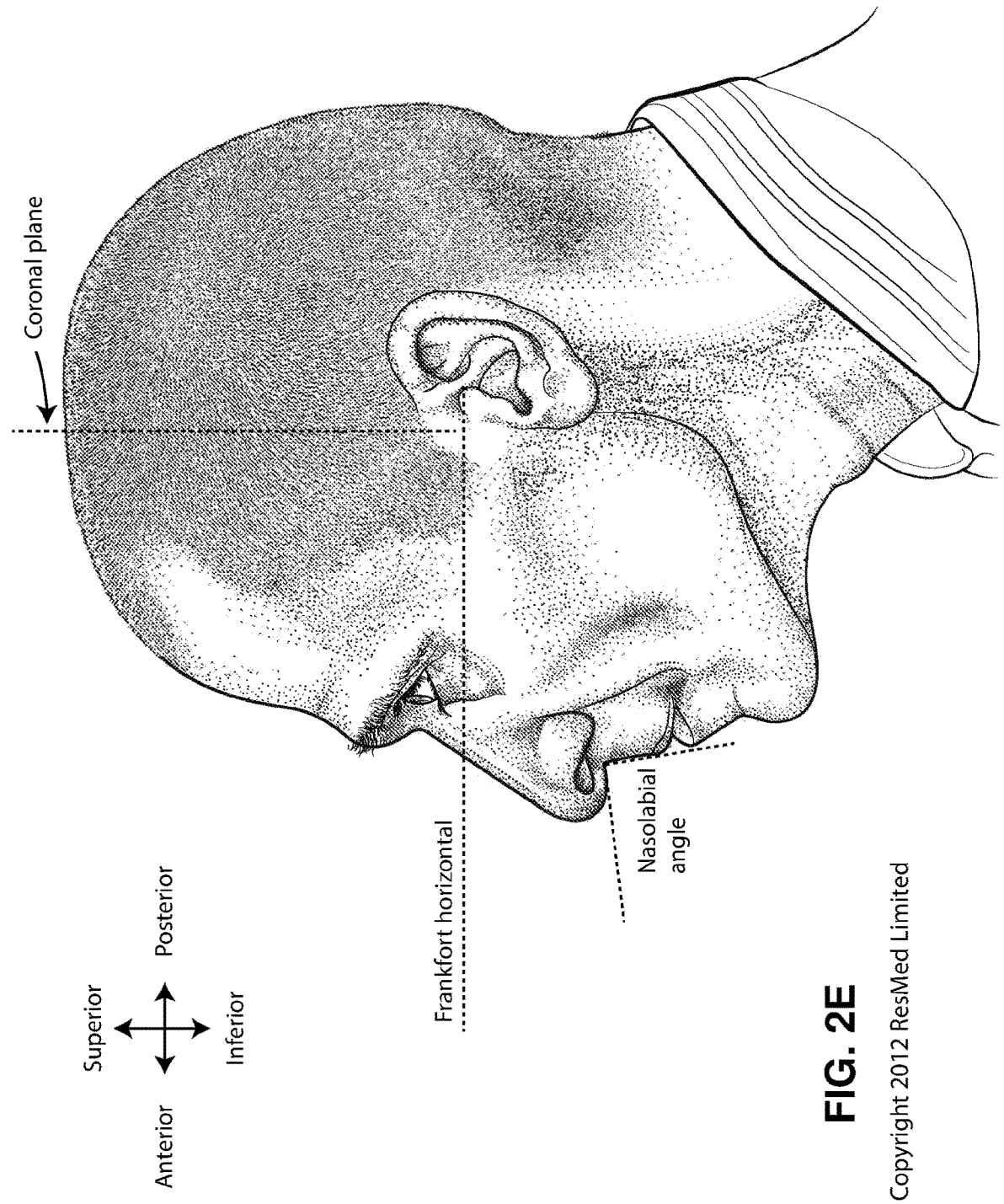

FIG. 2E is a further side view of a head. The approximate locations of the Frankfort horizontal and nasolabial angle are indicated. The coronal plane is also indicated.

Figure 2F:
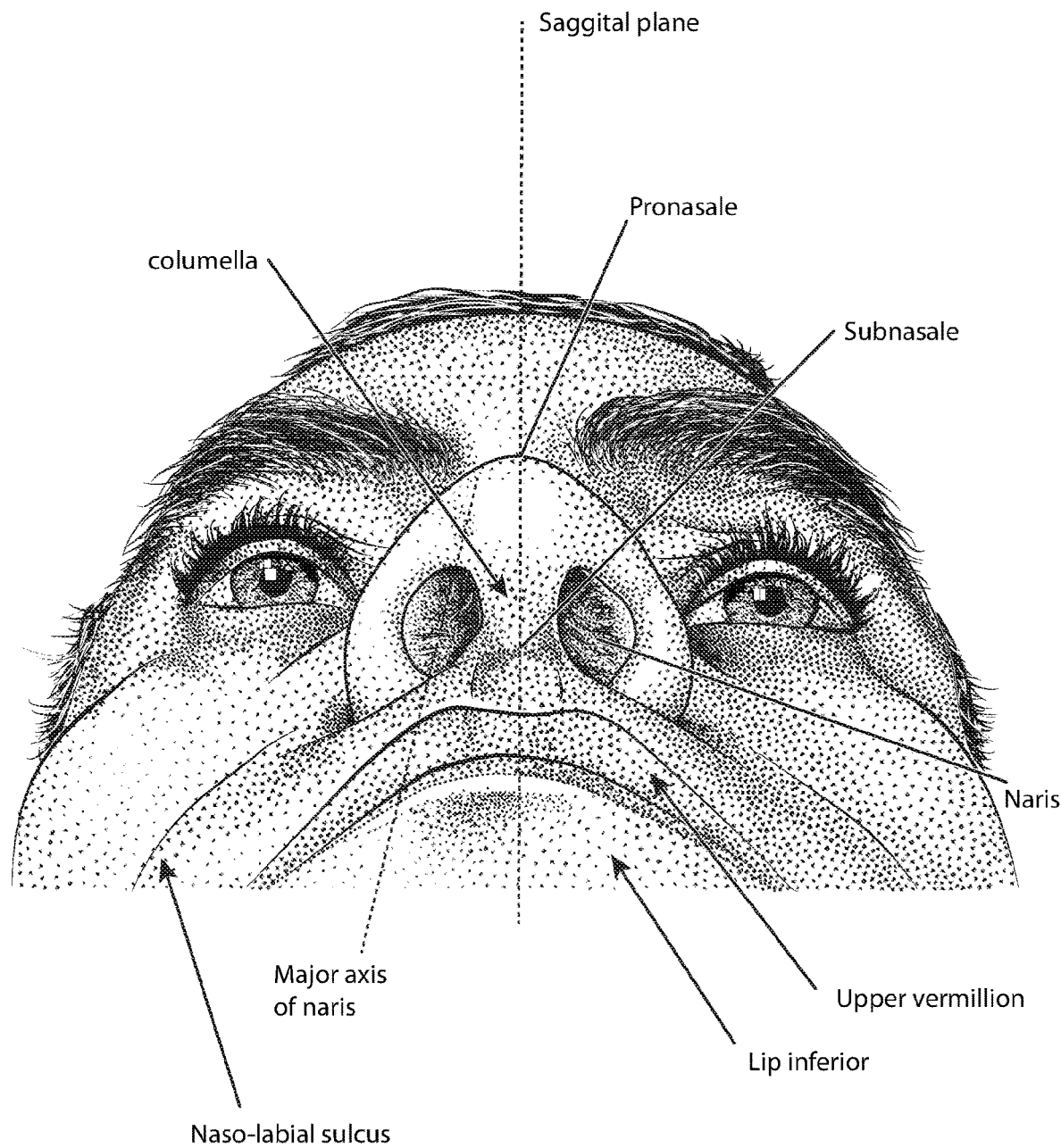

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
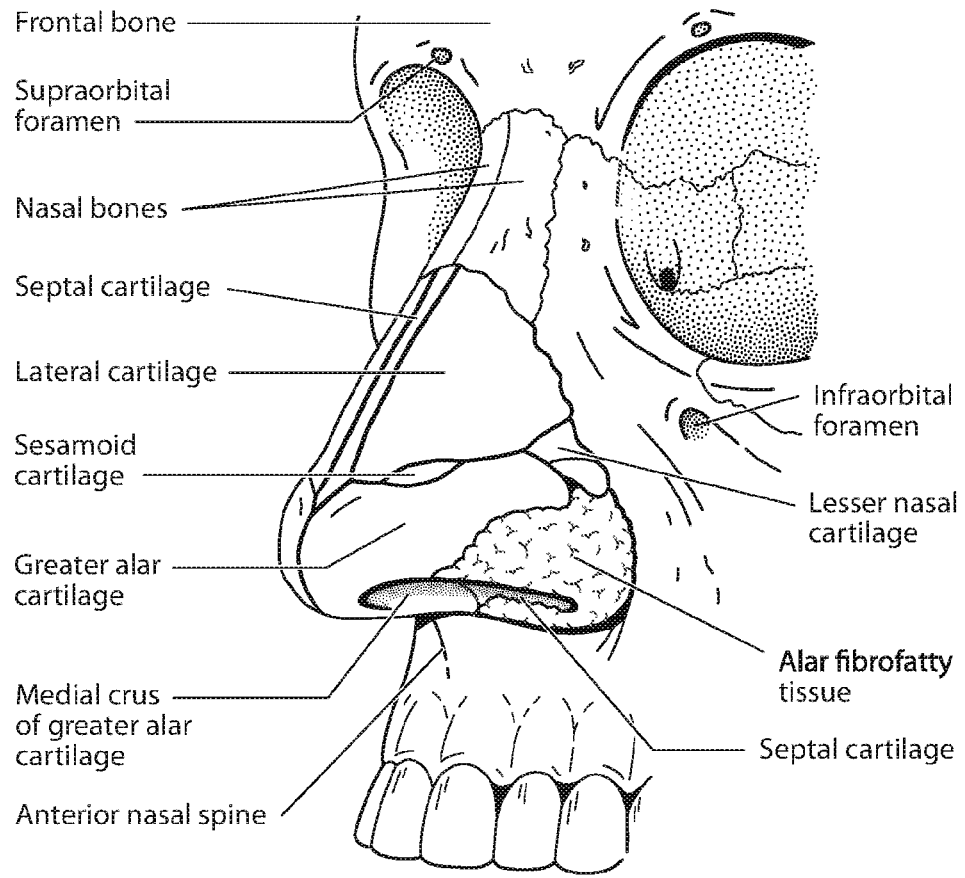

FIG. 2L shows an anterolateral view of a nose.

4.3 Patient Interface

Figure 3A:
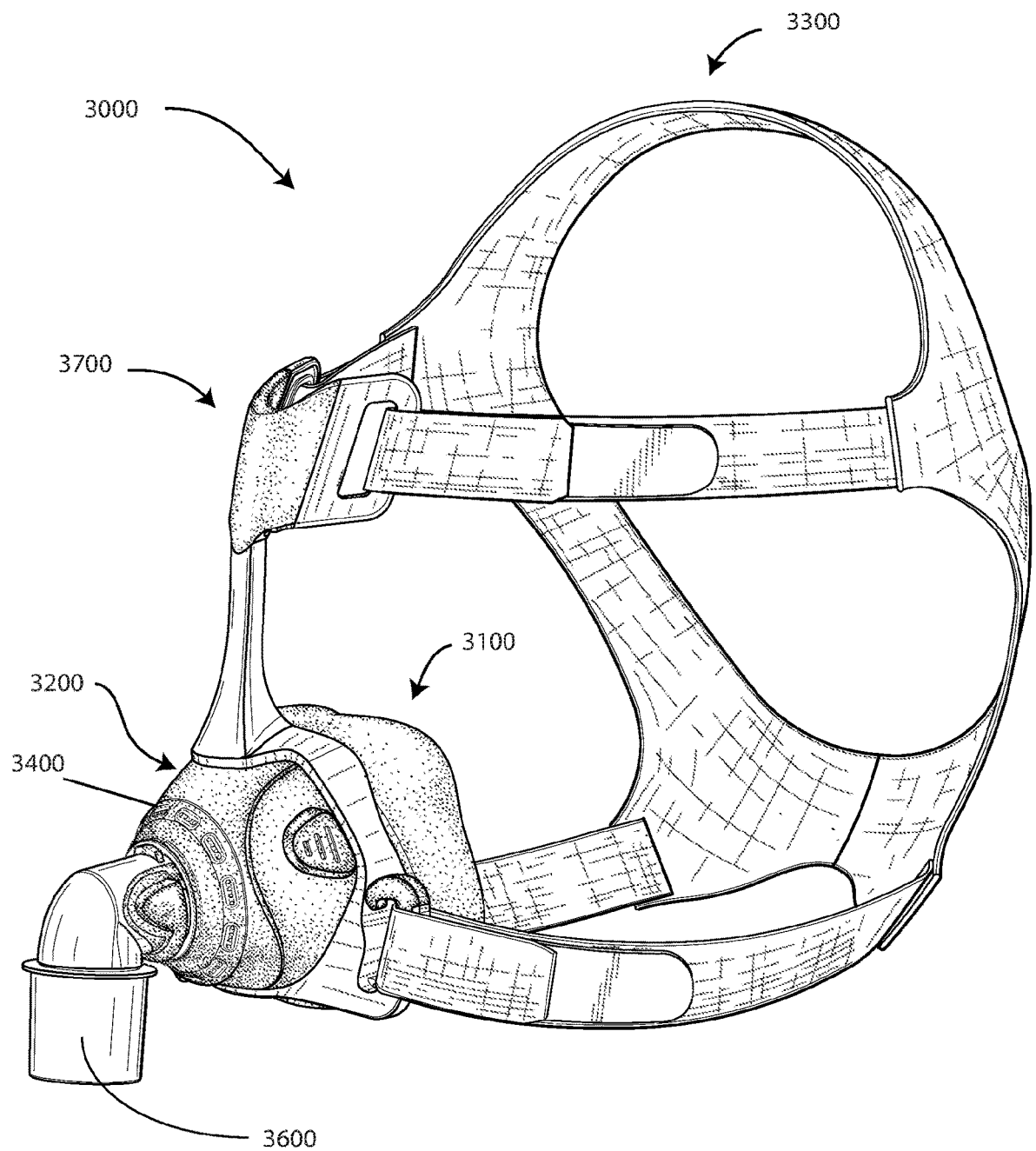

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
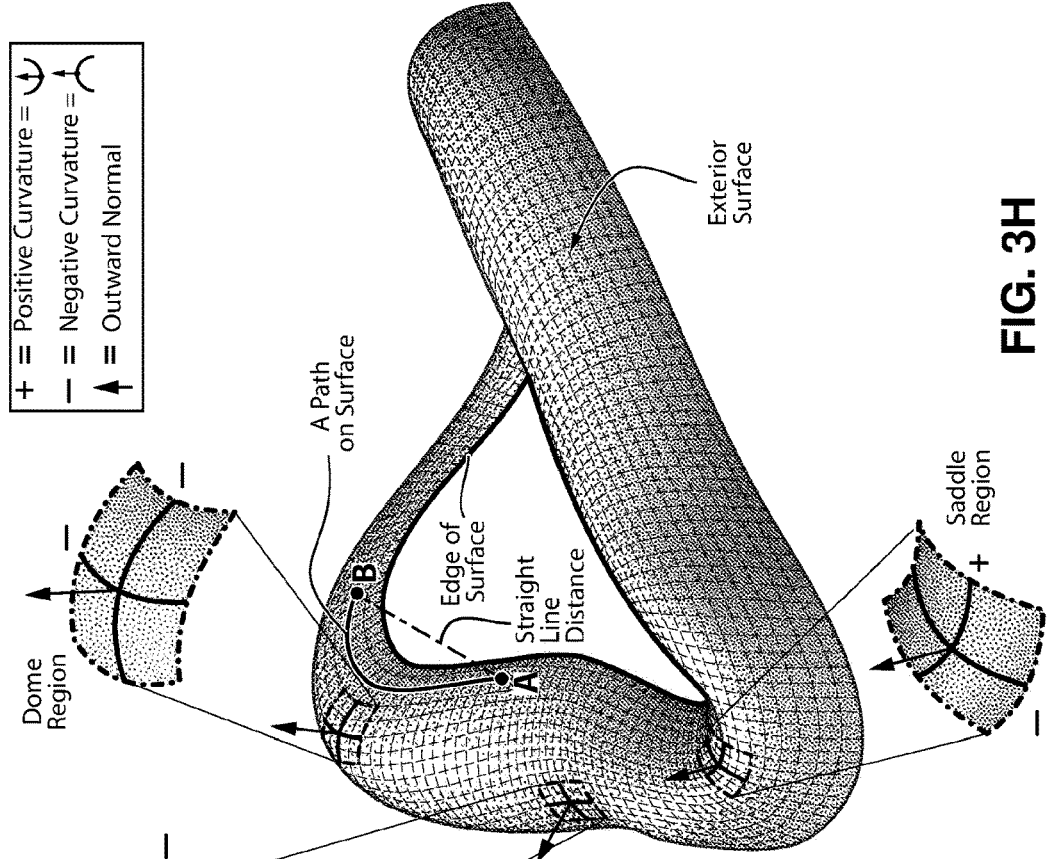
Figure 3G:
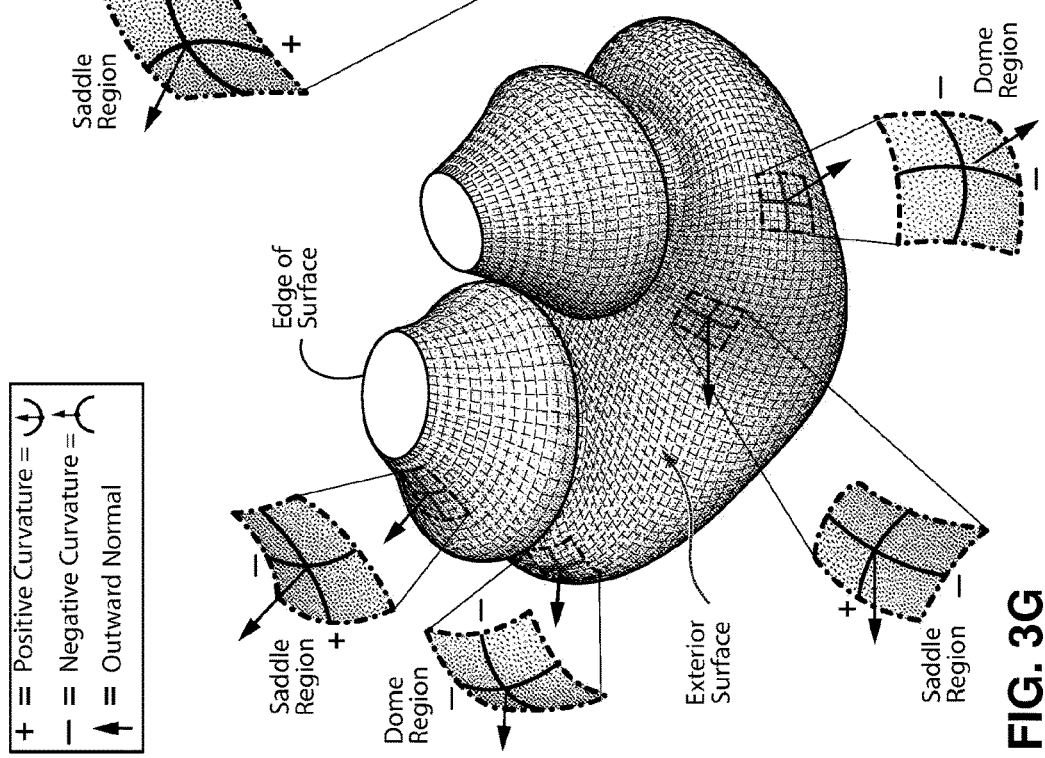

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
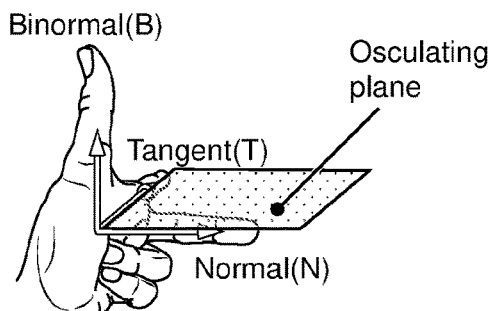

FIG. 3O illustrates a left-hand rule.

Figure 3P:
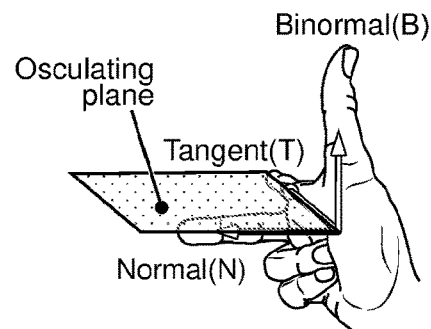

FIG. 3P illustrates a right-hand rule.

Figure 3Q:
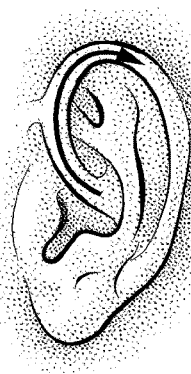

FIG. 3Q shows a left ear, including the left ear helix.

Figure 3S:
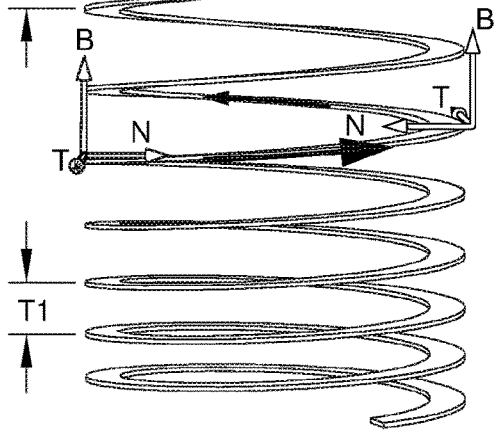
Figure 3R:

FIG. 3R shows a right ear, including the right ear helix.

FIG. 3S shows a right-hand helix.

Figure 3T:
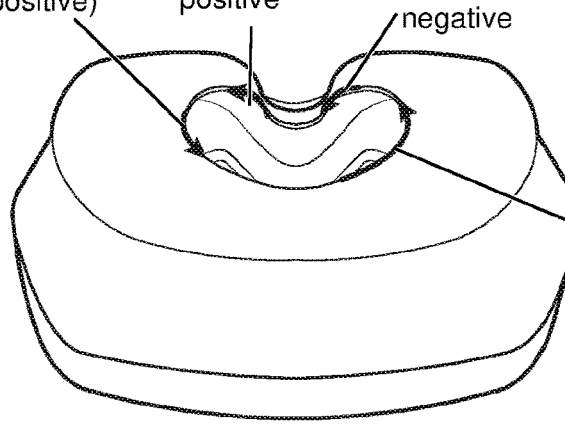

FIG. 3T shows a view of a mask, including the sign of the torsion of the space curve defined by the edge of the sealing membrane in different regions of the mask.

Figure 3U:
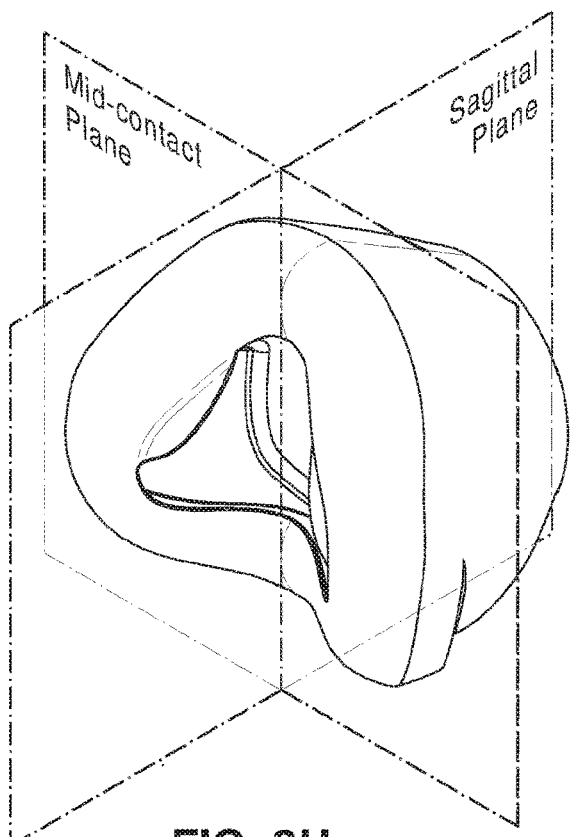

FIG. 3U shows a view of a plenum chamber 3200 showing a sagittal plane and a mid-contact plane.

Figure 3V:
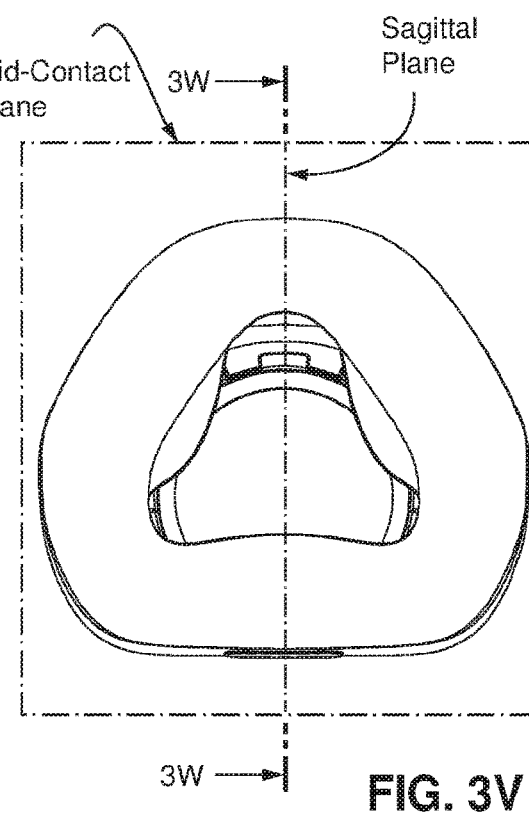

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
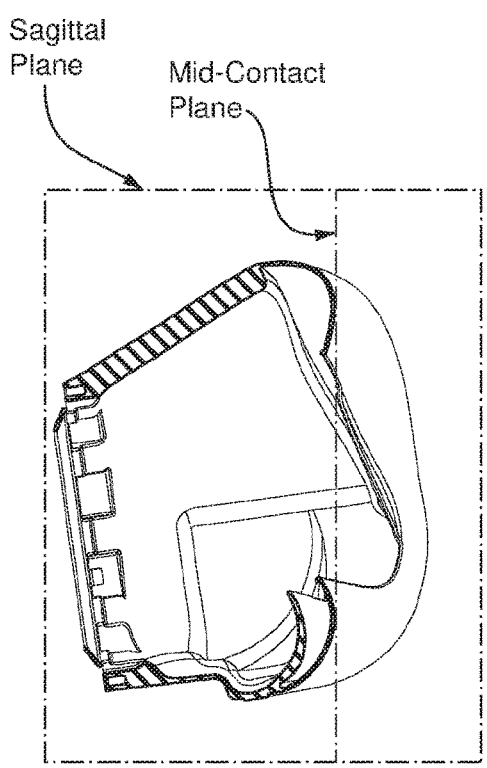

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
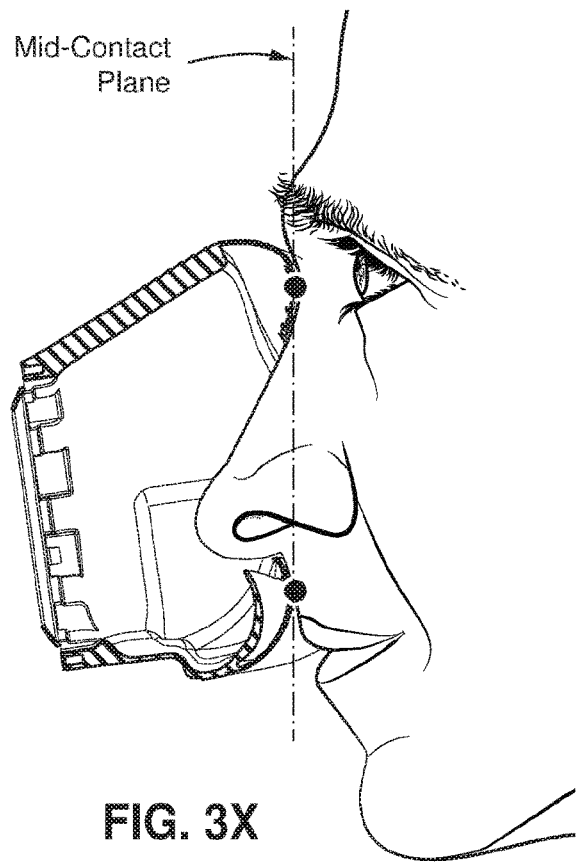

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 Patient Interface According to the Present Technology

Figure 4:
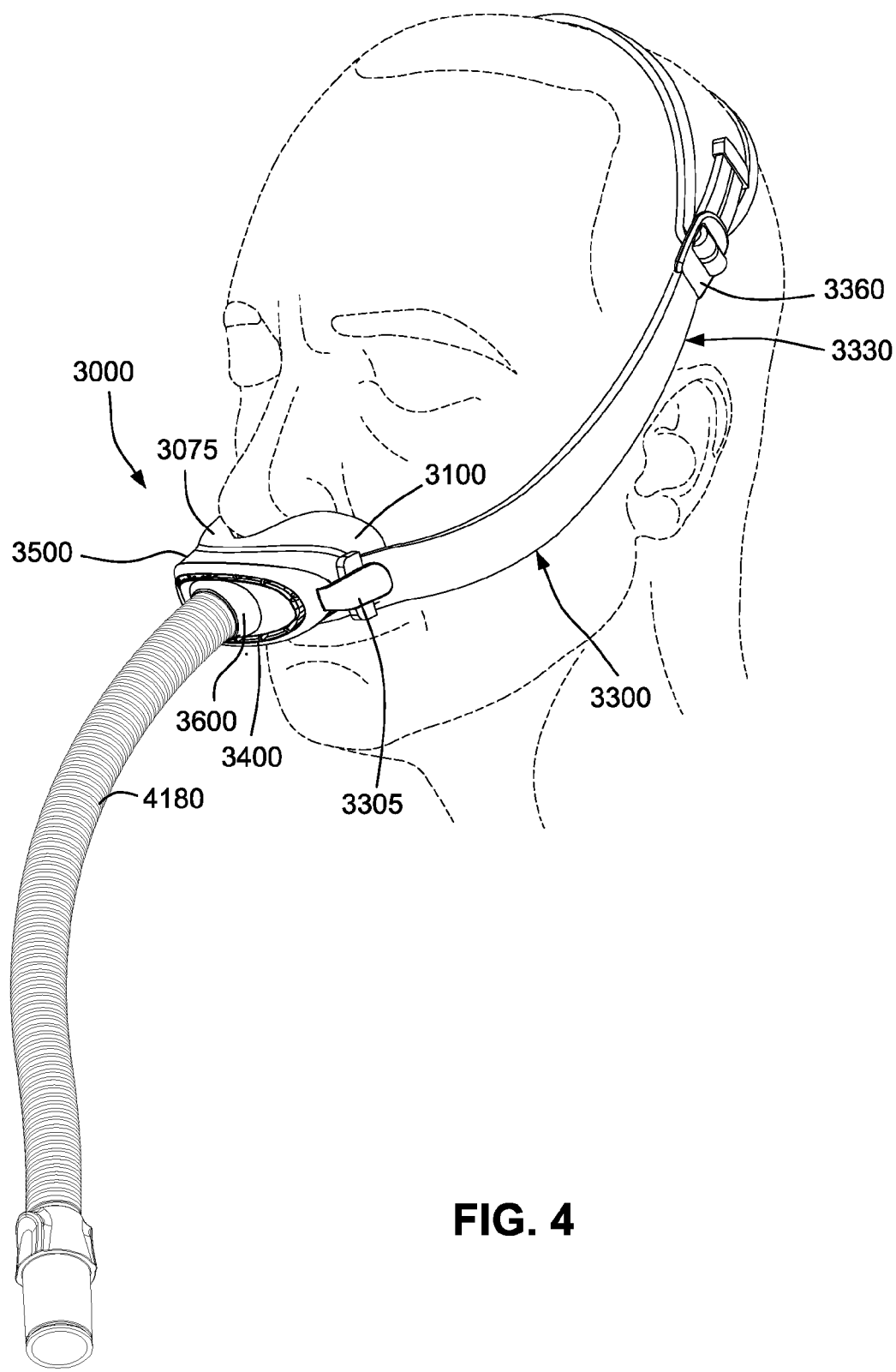

FIG. 4 is a perspective view of a patient interface shown on a patient's head according to an example of the present technology.

Figure 5:
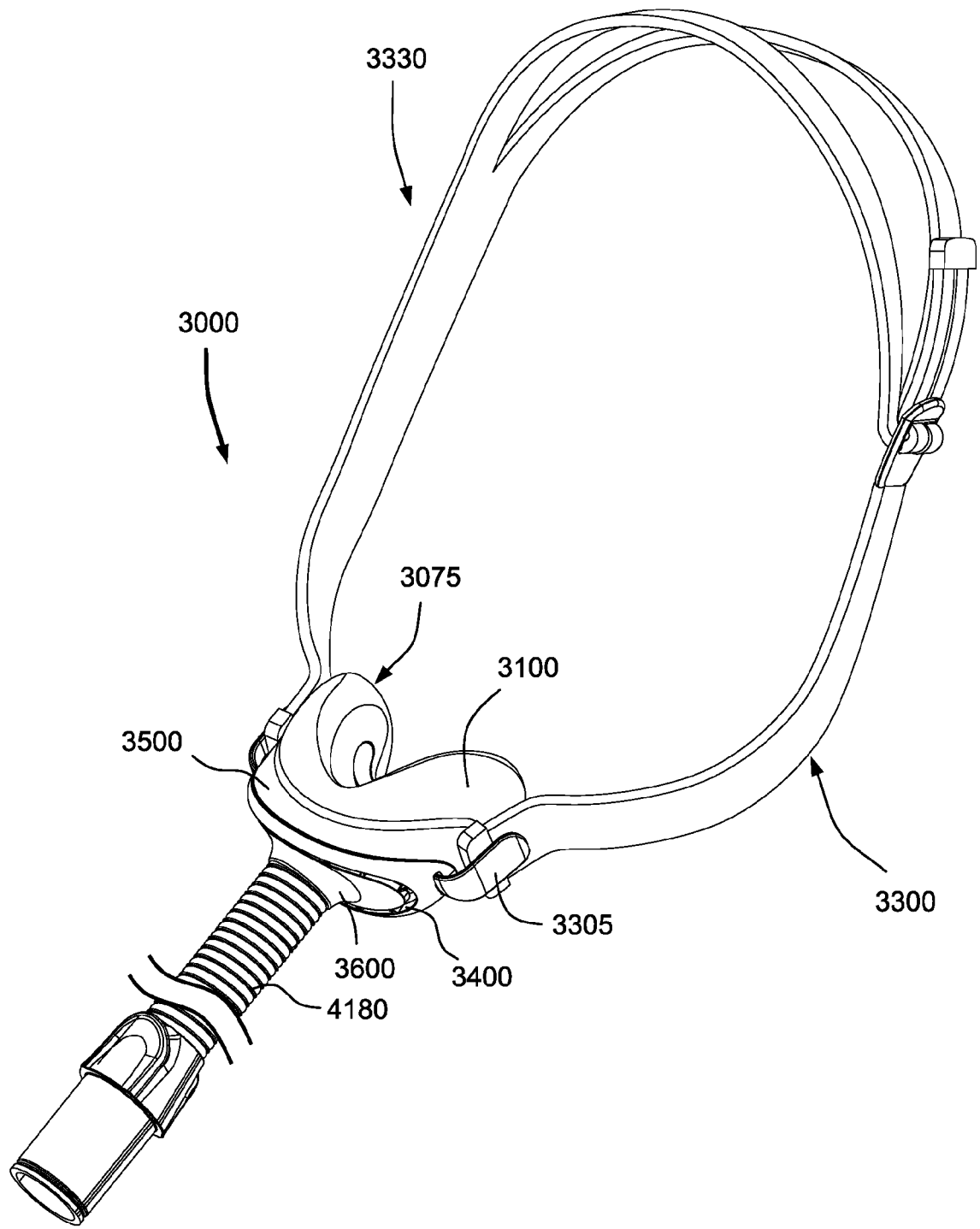

FIG. 5 is a perspective view of the patient interface of FIG. 4 according to an example of the present technology.

Figure 6:
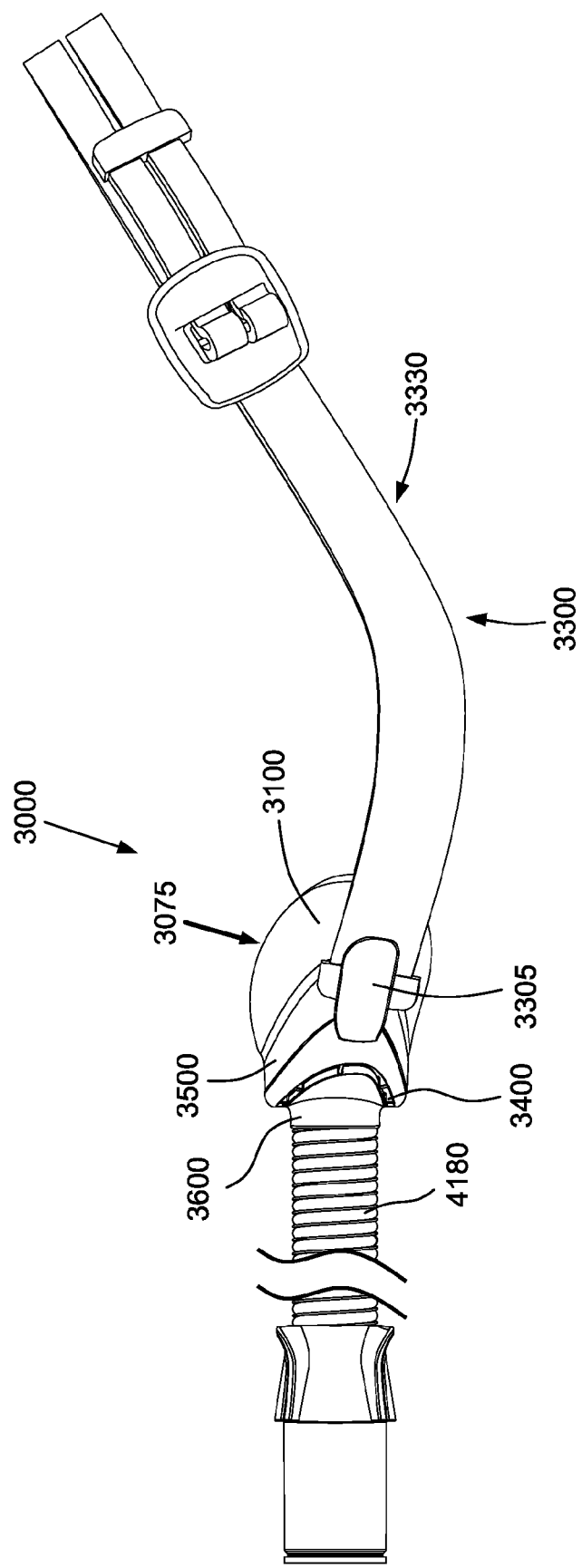

FIG. 6 is a side view of the patient interface shown in FIG. 5.

Figure 7:
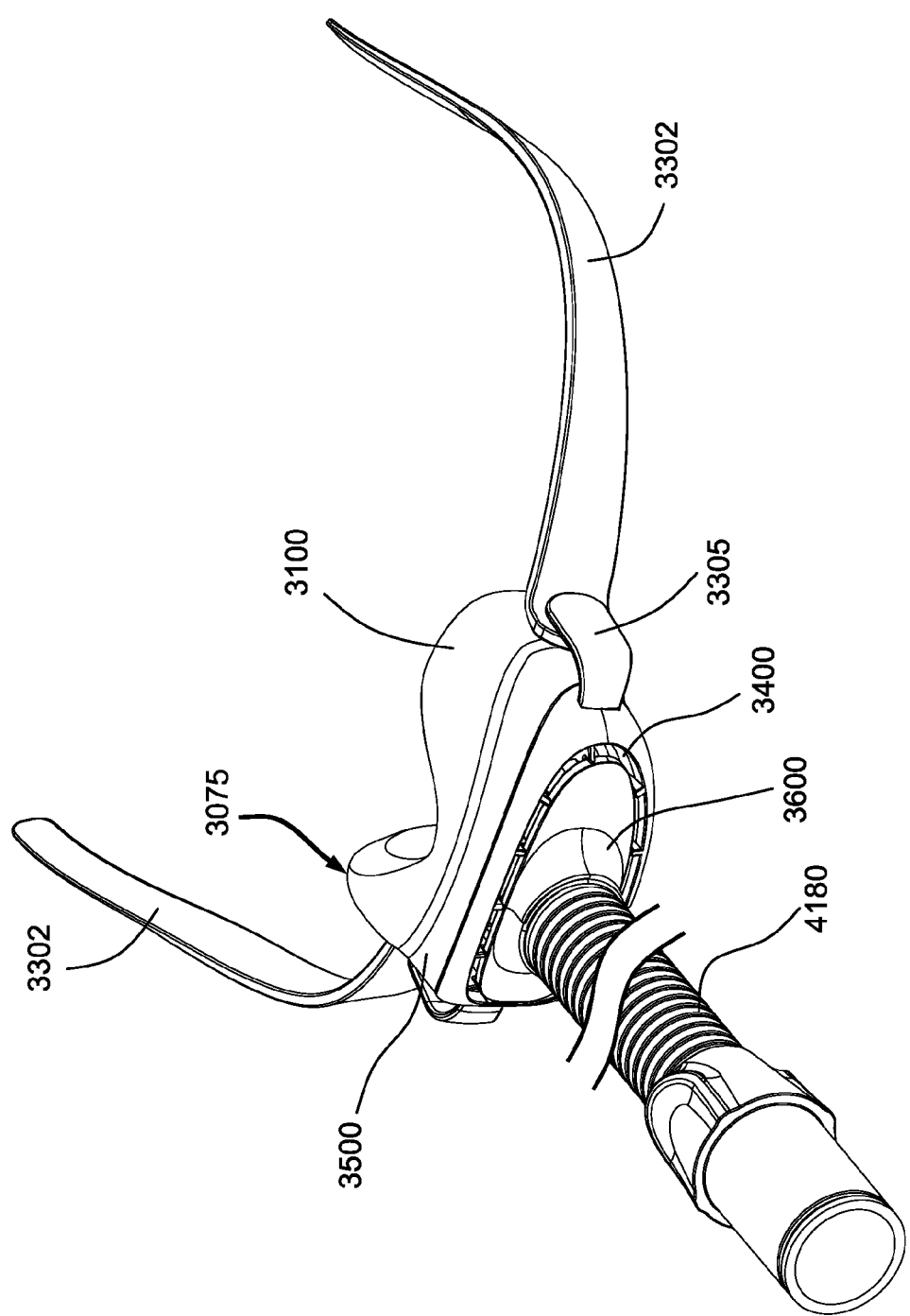

FIG. 7 is a perspective view of the patient interface of FIG. 5 according to an example of the present technology, the patient interface being shown with a headgear strap assembly removed.

Figure 8:
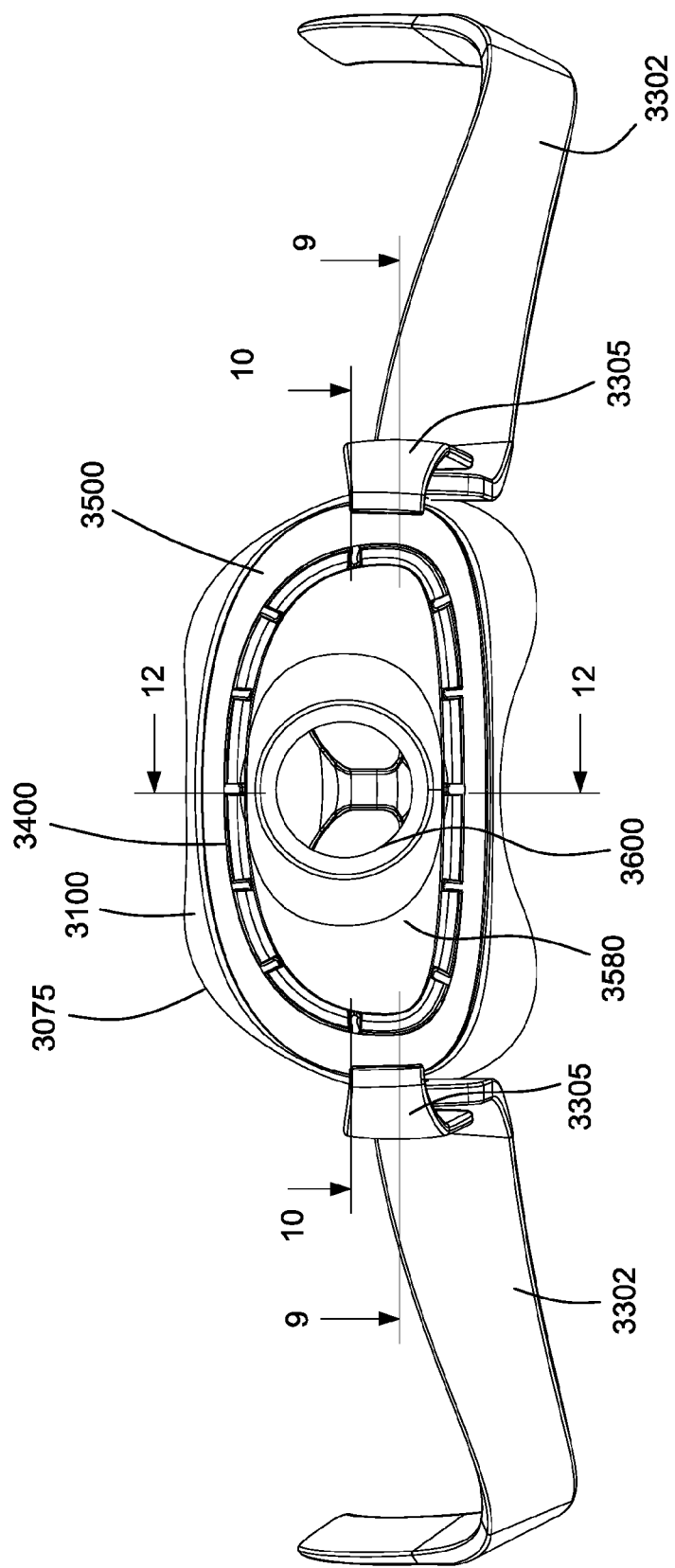

FIG. 8 is a front view of the patient interface shown in FIG. 7.

Figure 9:
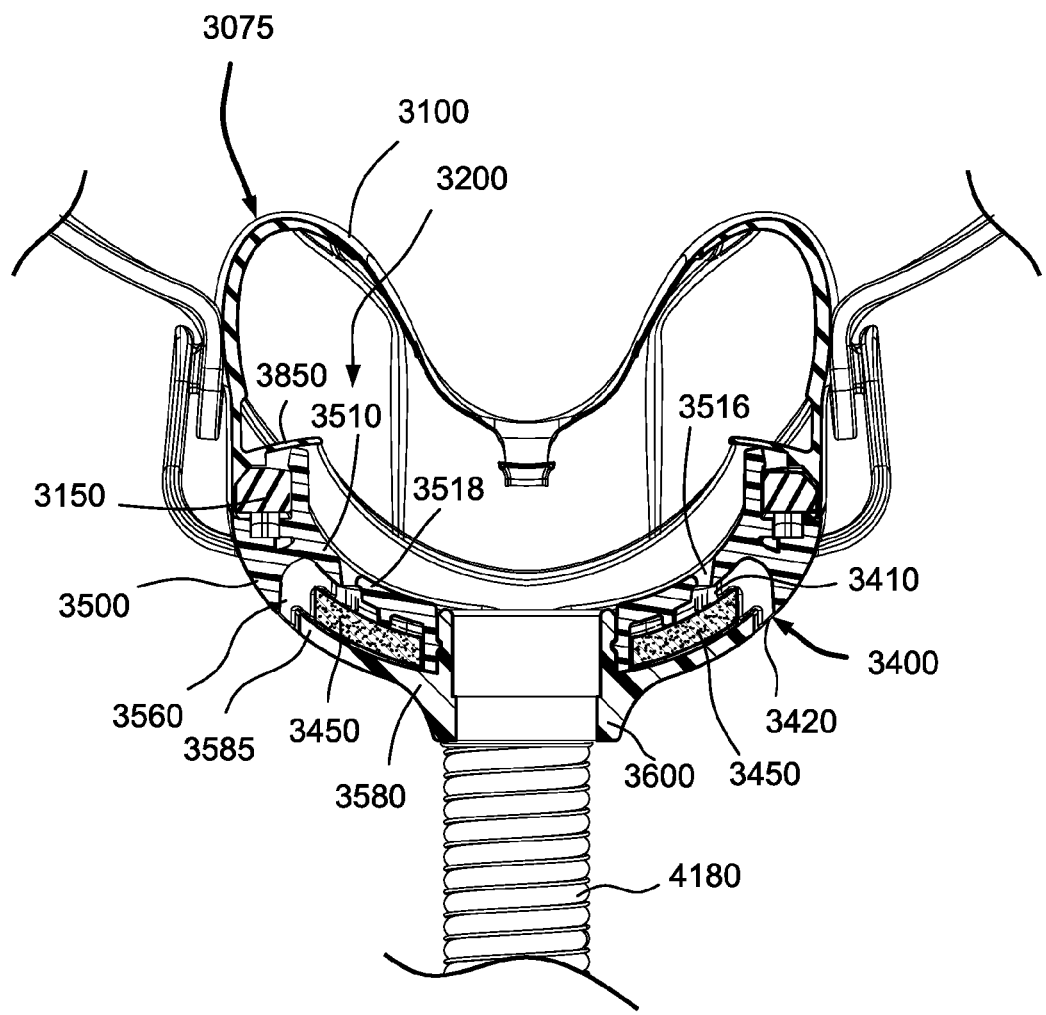

FIG. 9 is a cross-sectional view through line 9-9 of FIG. 8.

Figure 10:
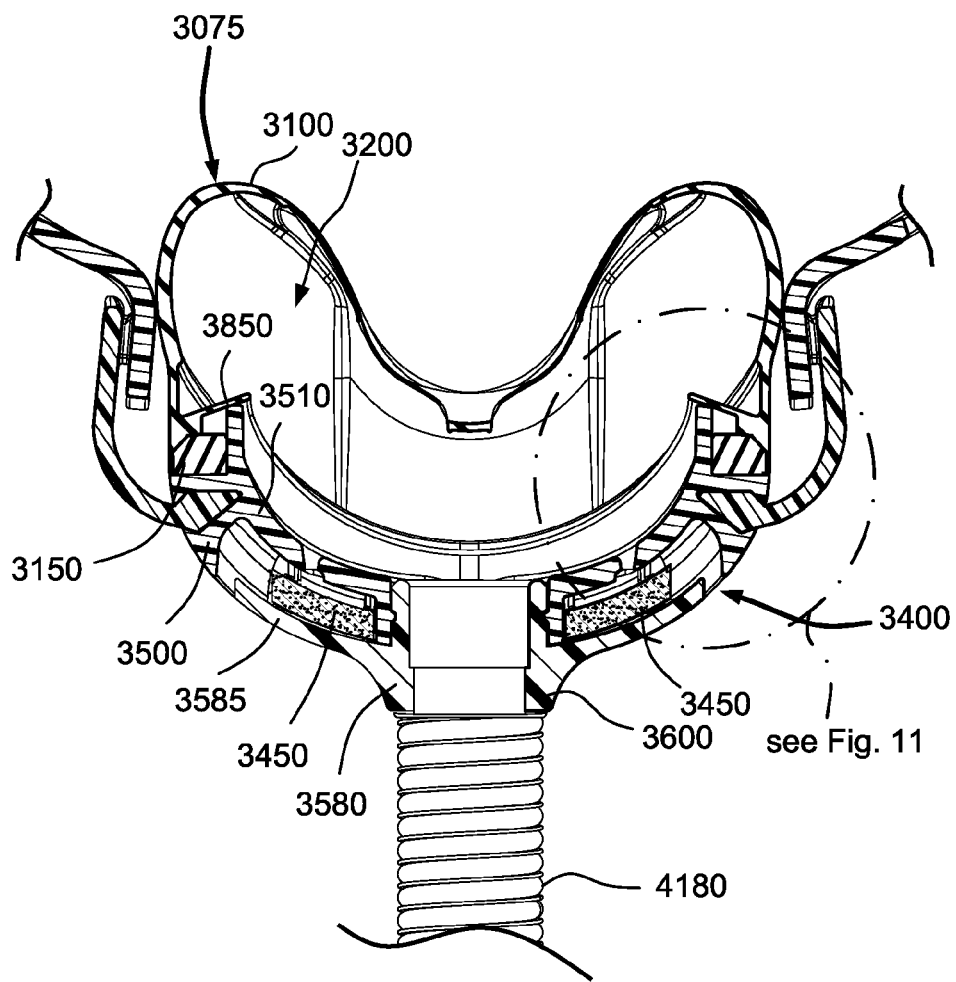

FIG. 10 is a cross-sectional view through line 10-10 of FIG. 8.

Figure 11:
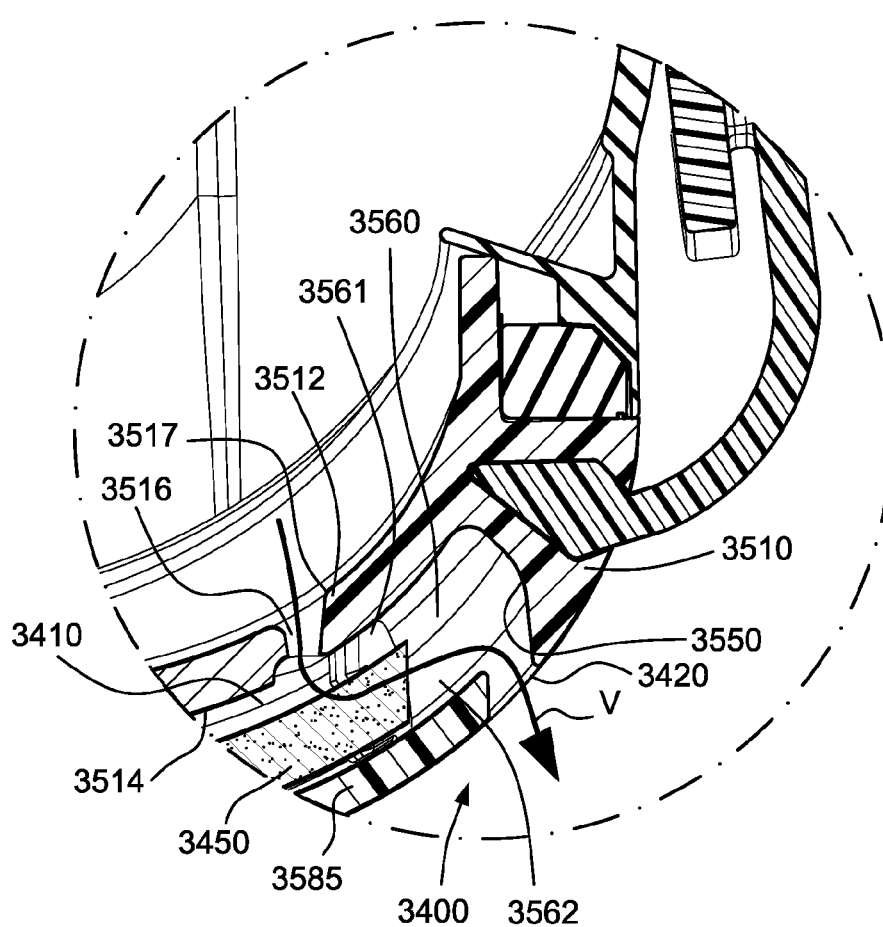

FIG. 11 is an enlarged portion of the cross-section shown in FIG. 10.

Figure 12:
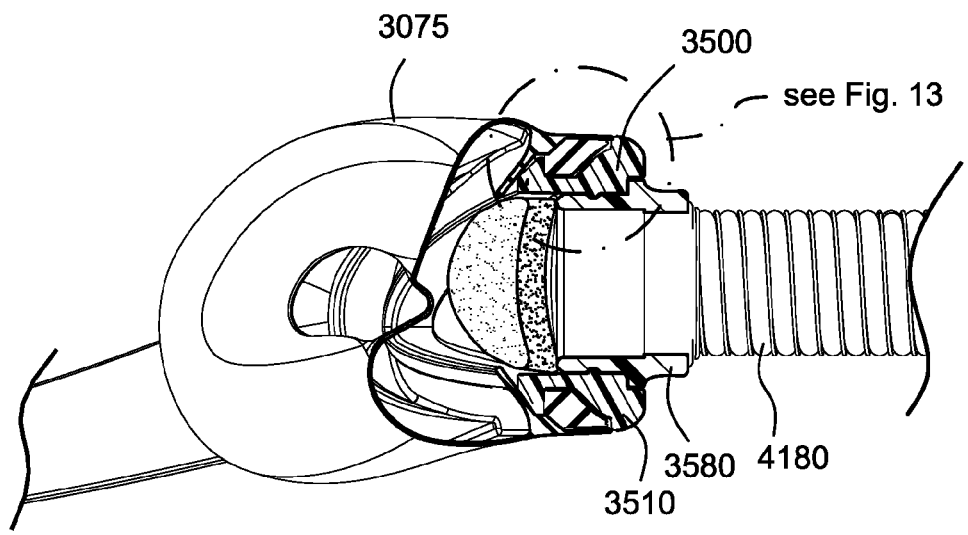

FIG. 12 is a cross-sectional view through line 12-12 of FIG. 8.

Figure 13:
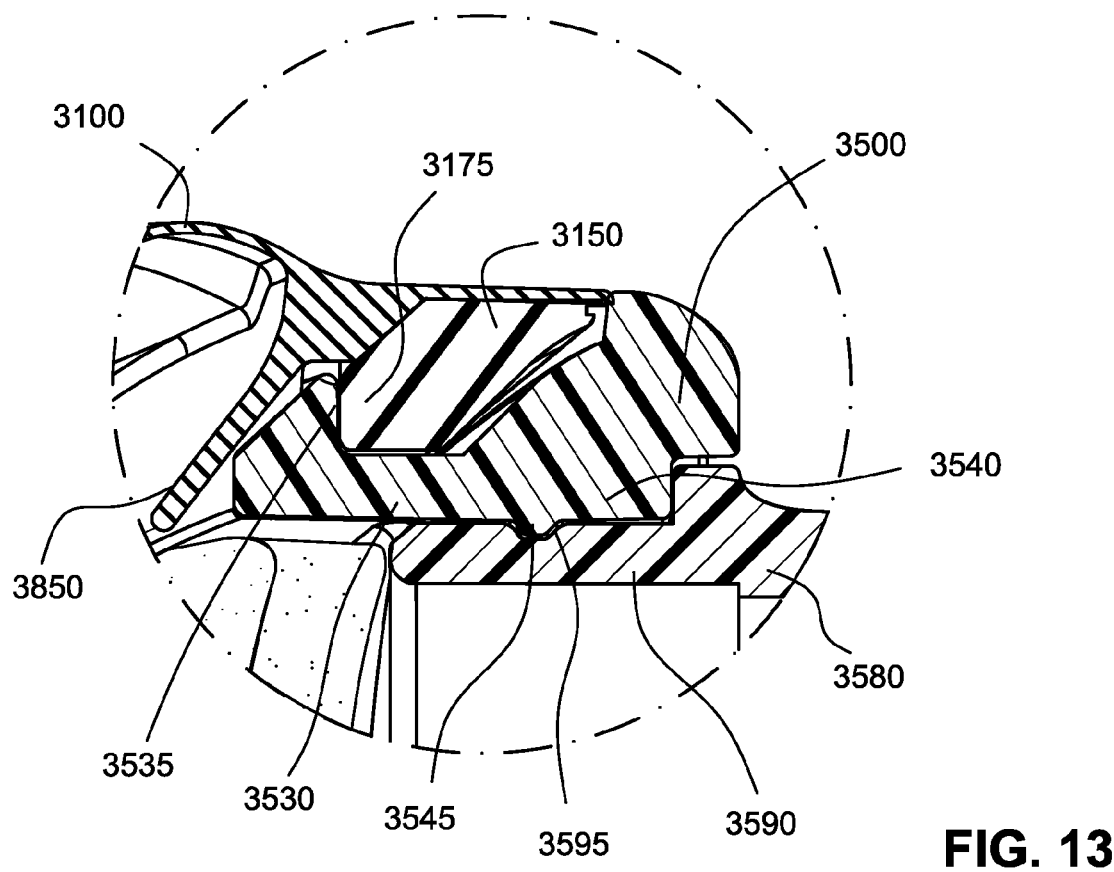

FIG. 13 is an enlarged portion of the cross-section shown in FIG. 12.

Figure 14:
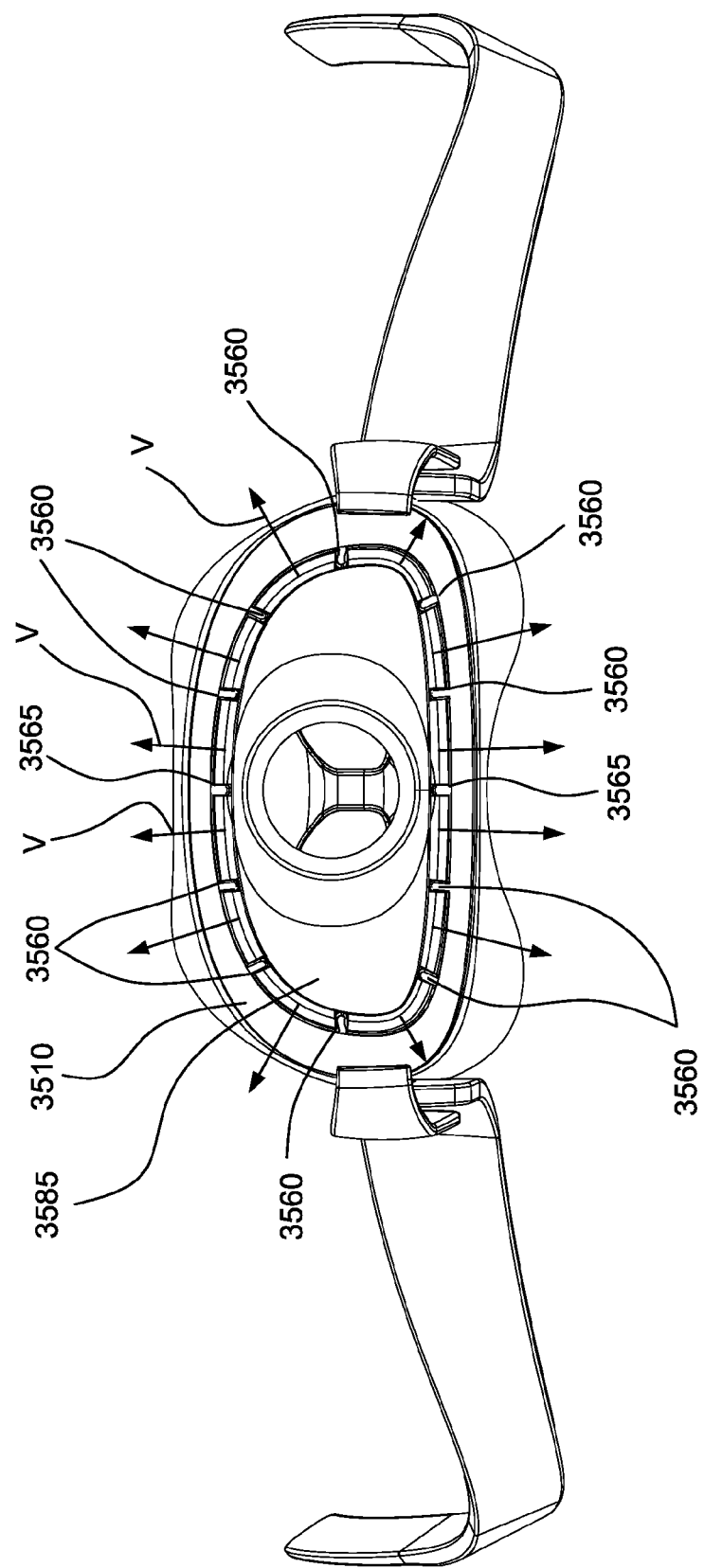

FIG. 14 is a front view of the patient interface shown in FIG. 7 showing vent flow paths of a vent according to an example of the present technology.

Figure 15:
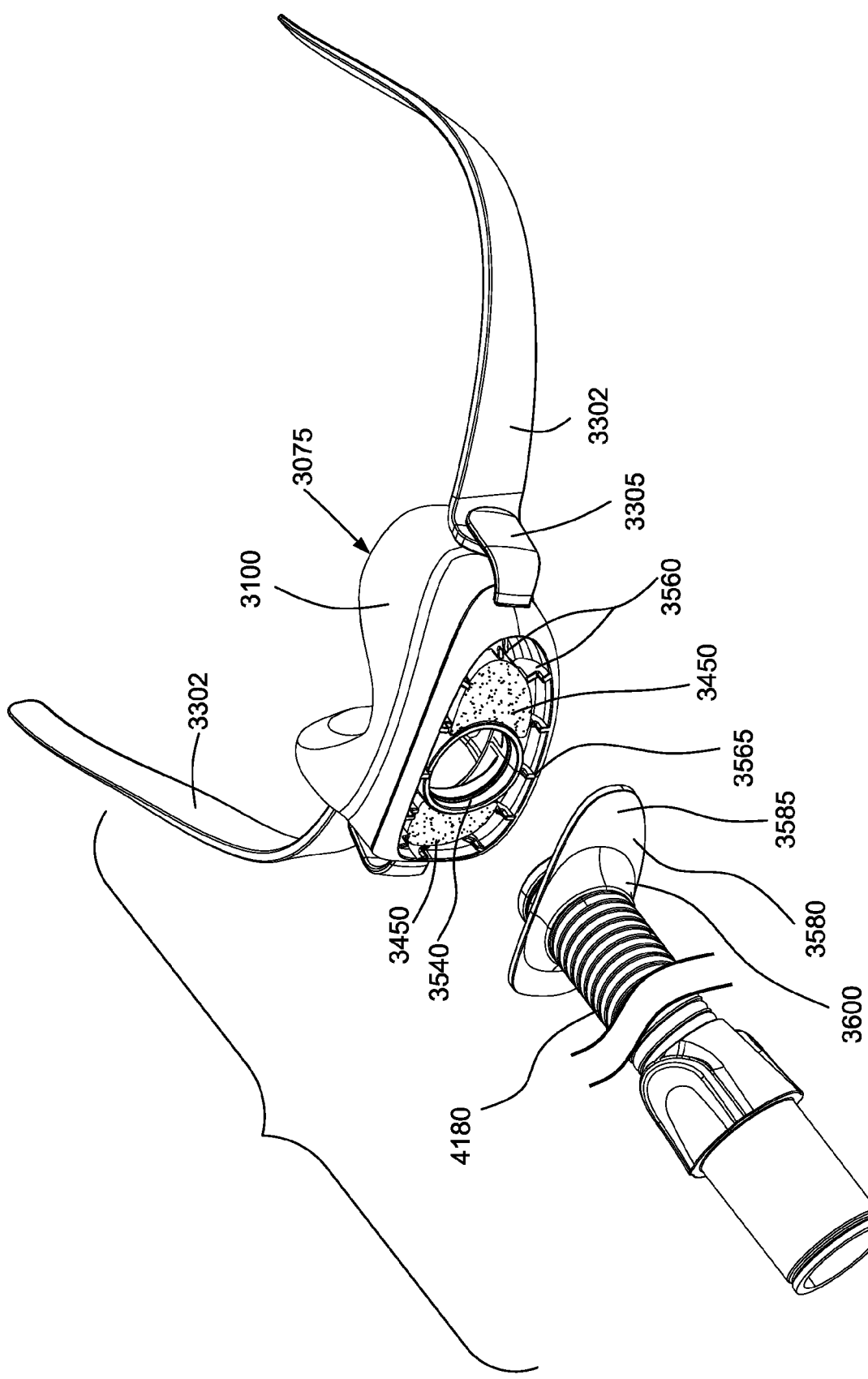

FIG. 15 is an exploded view when viewed from the front of the patient interface shown in FIG. 7.

Figure 16:
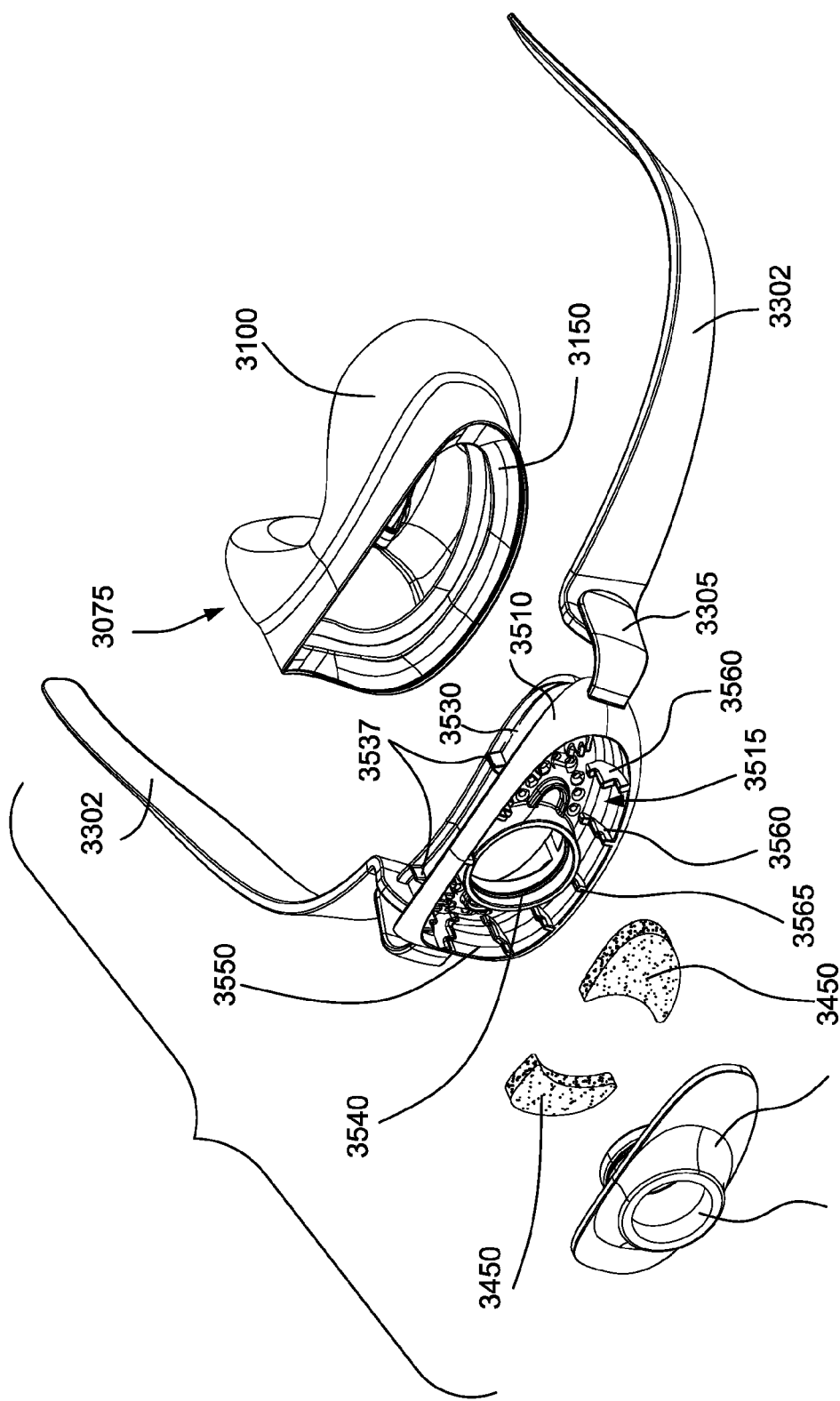

FIG. 16 is another exploded view when viewed from the front of the patient interface shown in FIG. 7.

Figure 17:
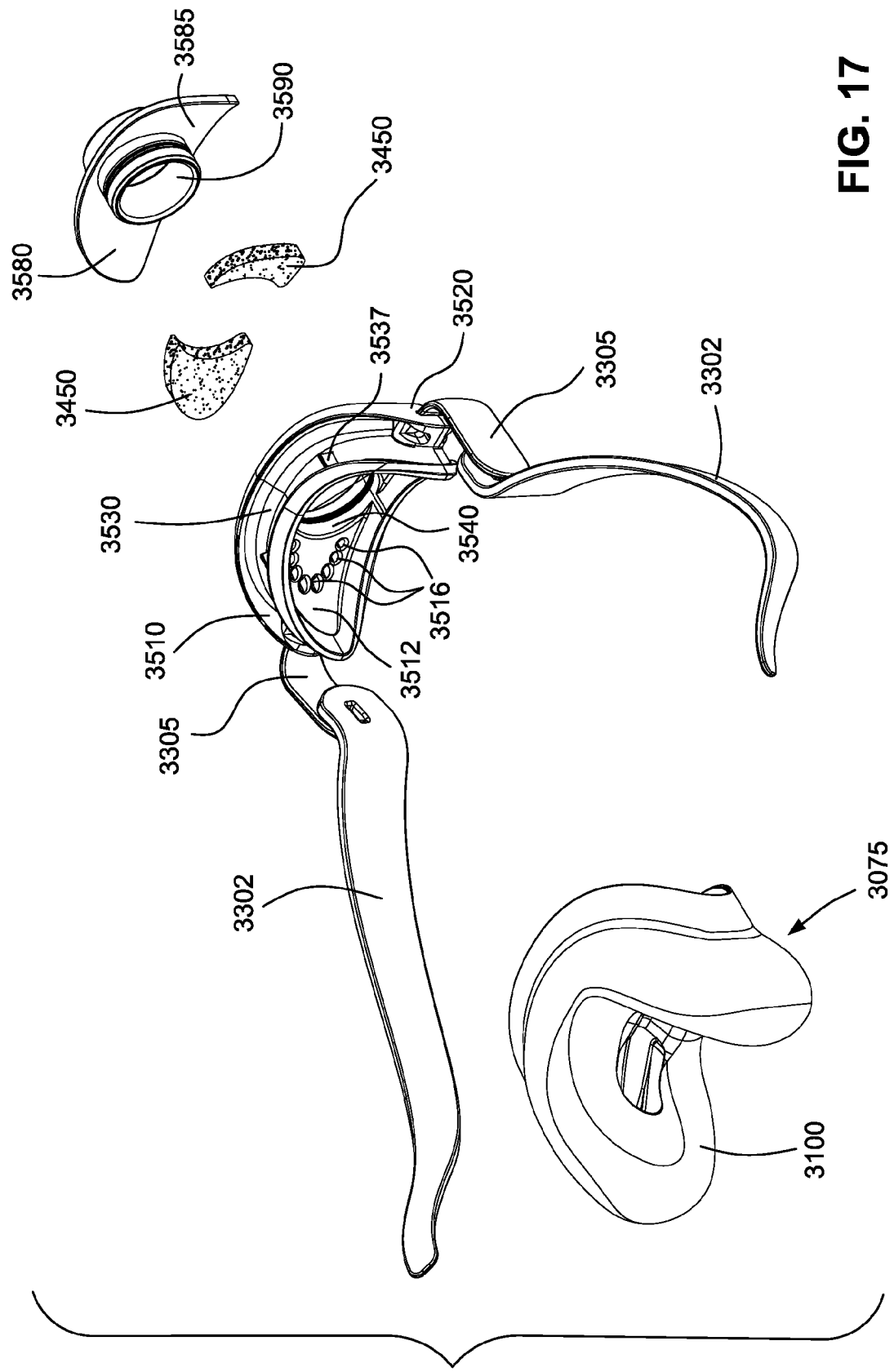

FIG. 17 is an exploded view when viewed from the rear of the patient interface shown in FIG. 7.

Figure 18:
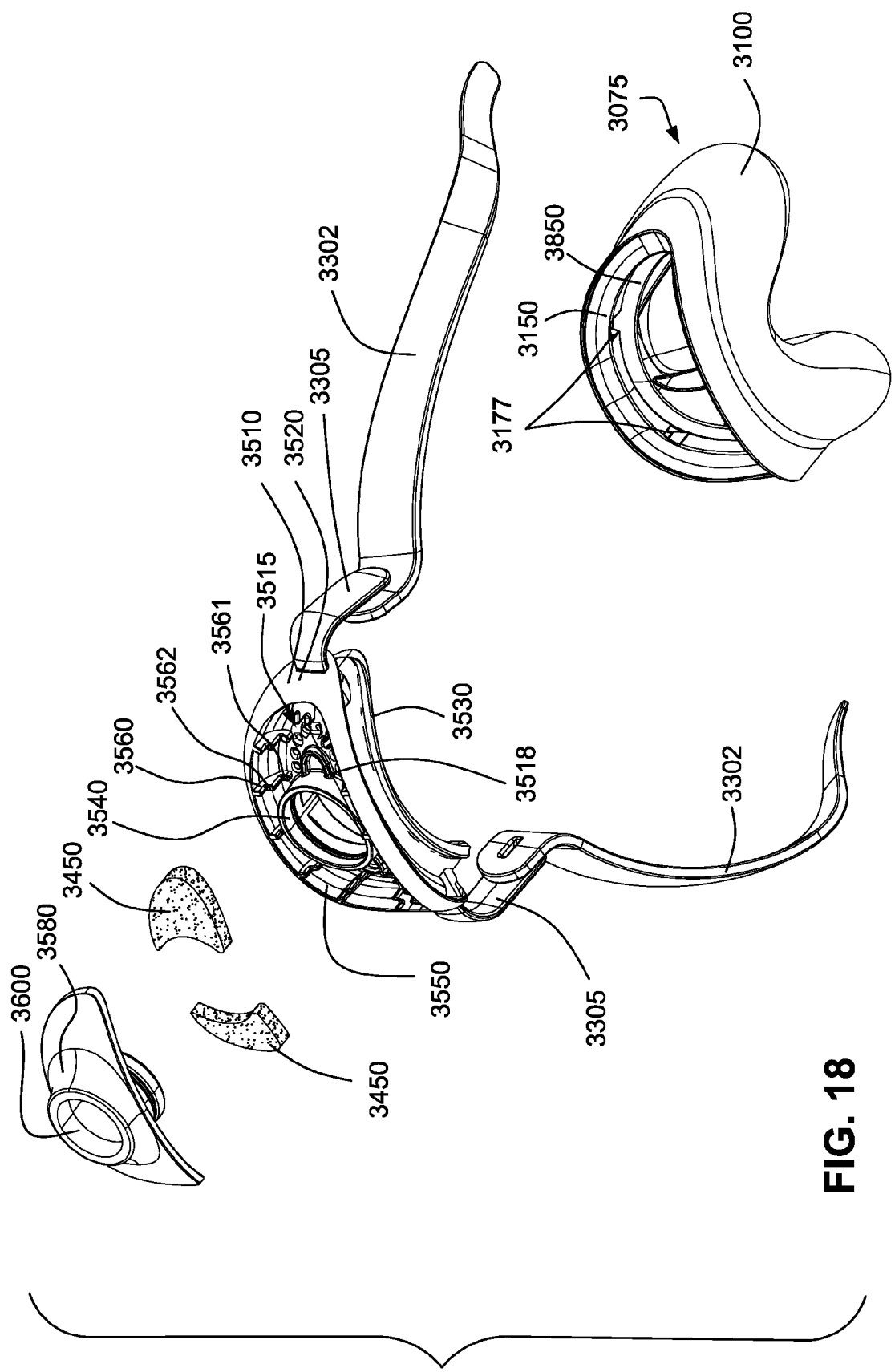

FIG. 18 is an exploded view when viewed from the bottom of the patient interface shown in FIG. 7.

Figure 19:
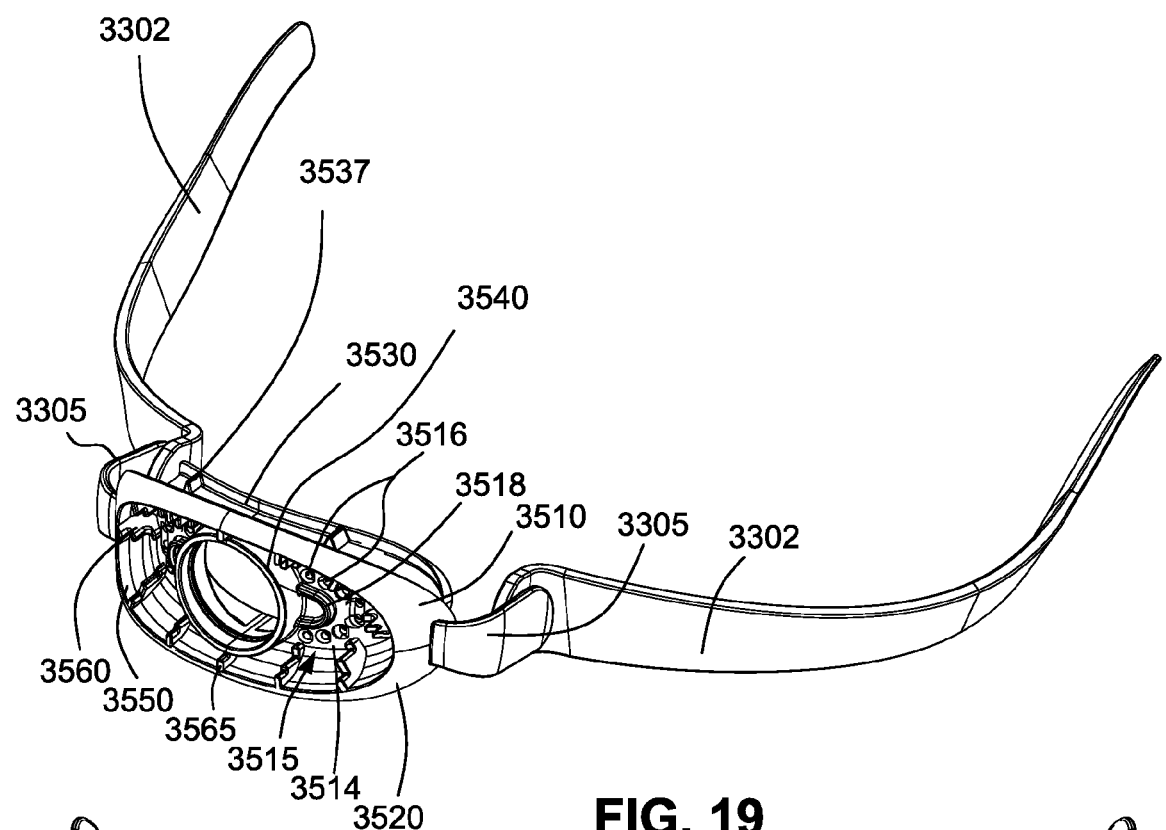

FIG. 19 is a perspective view of a main body of a frame assembly of the patient interface shown in FIG. 7.

Figure 20:
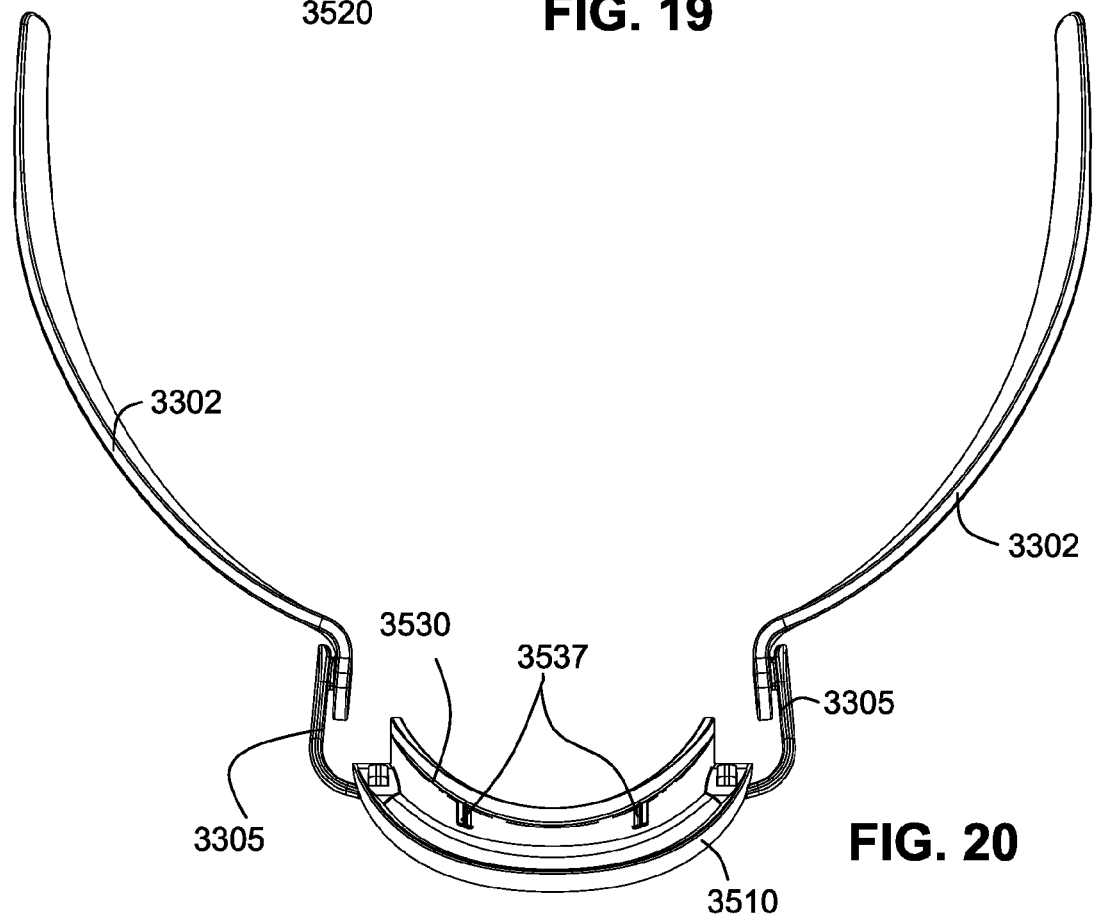

FIG. 20 is a top view of the main body of the frame assembly shown in FIG. 19.

Figure 21:
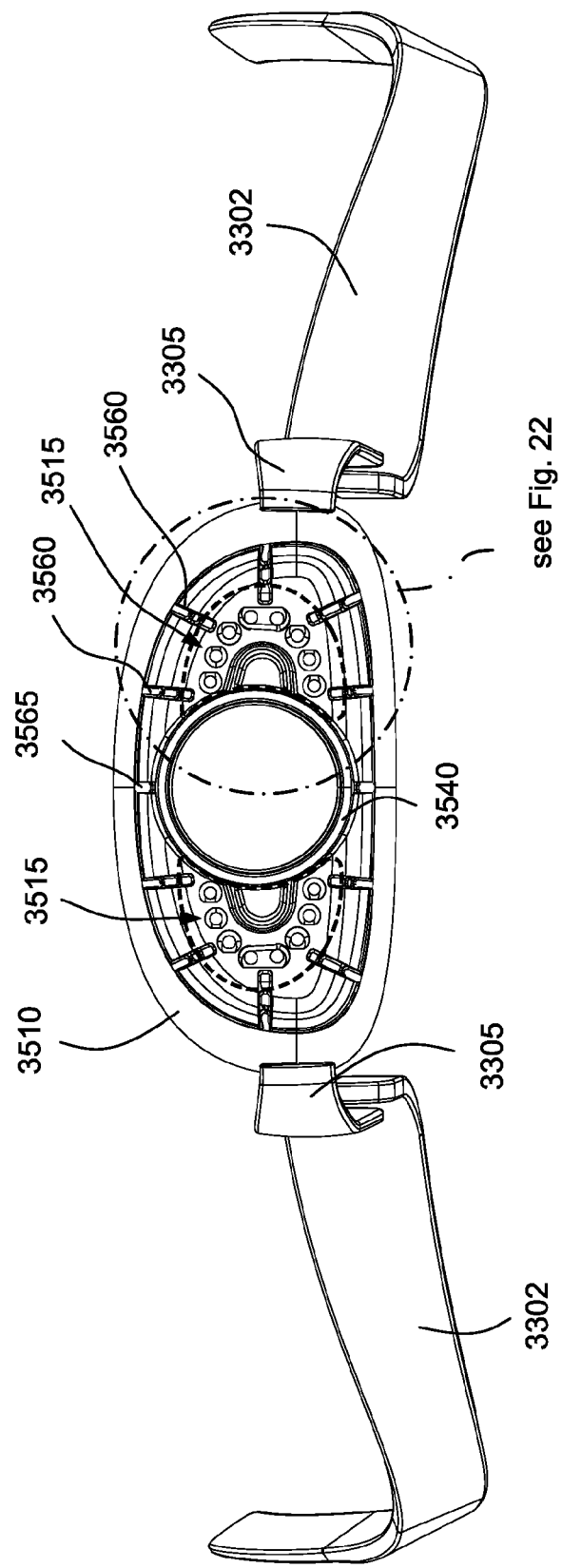

FIG. 21 is a front view of the main body of the frame assembly shown in FIG. 19.

Figure 22:
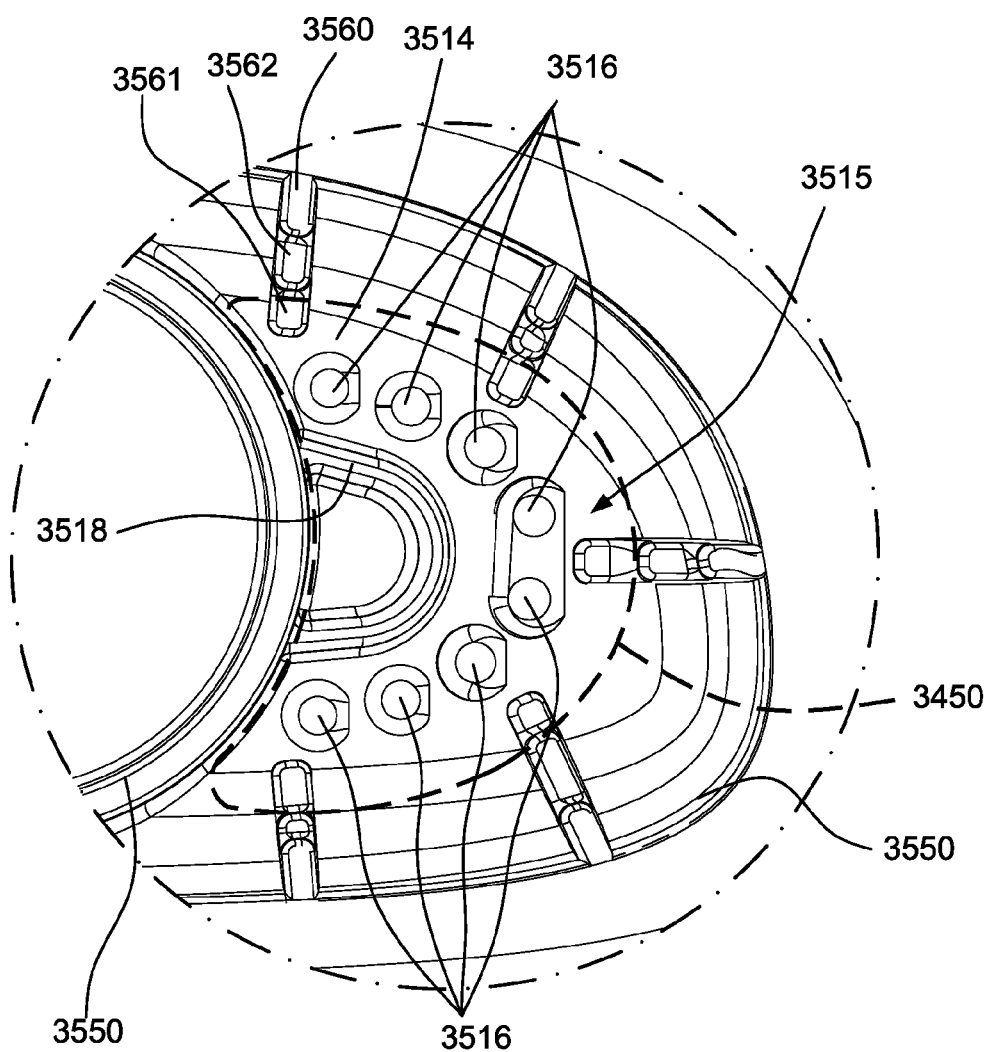

FIG. 22 is an enlarged portion of the main body of the frame assembly shown in FIG. 21.

Figure 23:
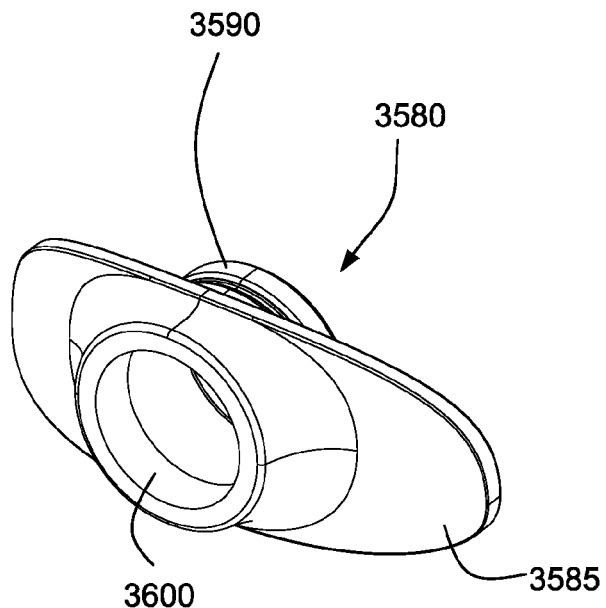

FIG. 23 is a perspective view of a cover of a frame assembly of the patient interface shown in FIG. 7.

Figure 24:
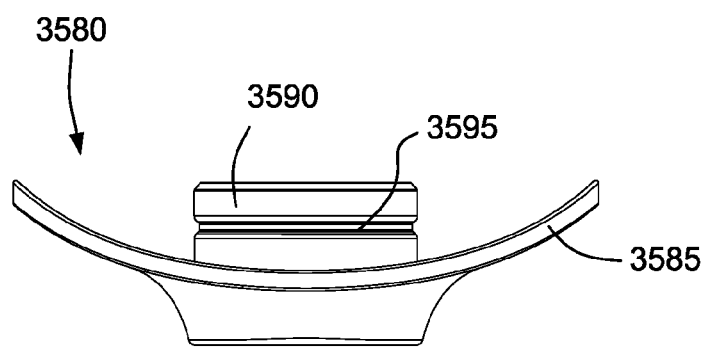

FIG. 24 is a top view of the cover of the frame assembly shown in FIG. 23.

Figure 25:
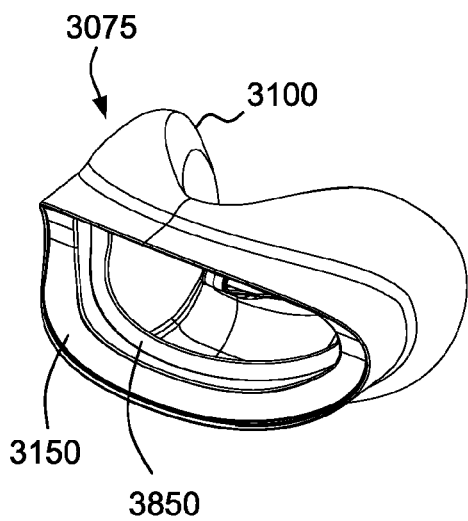

FIG. 25 is a perspective view of a cushion assembly of the patient interface shown in FIG. 7.

Figure 26:
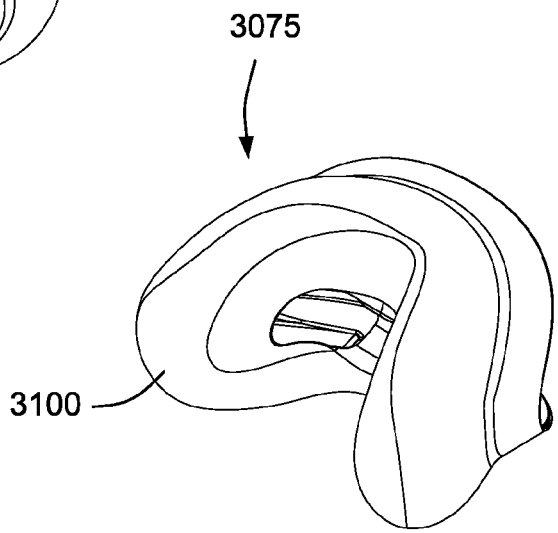

FIG. 26 is another perspective view of the cushion assembly shown in FIG. 25.

Figure 27:
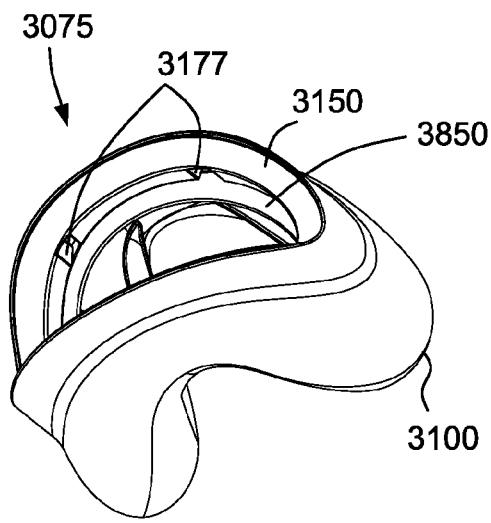

FIG. 27 is another perspective view of the cushion assembly shown in FIG. 25.

Figure 28:
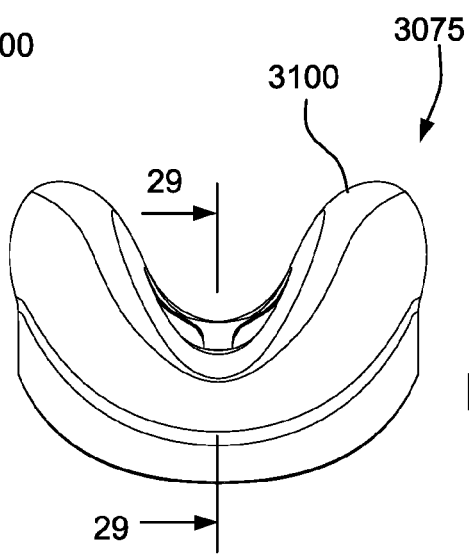

FIG. 28 is a top view of the cushion assembly shown in FIG. 25.

Figure 29:
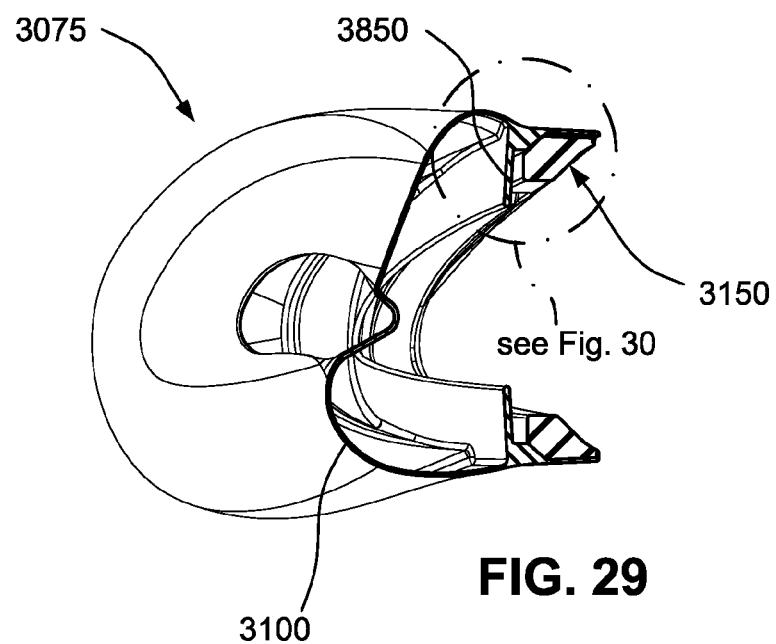

FIG. 29 is a cross-sectional view through line 29-29 of FIG. 28.

Figure 30:
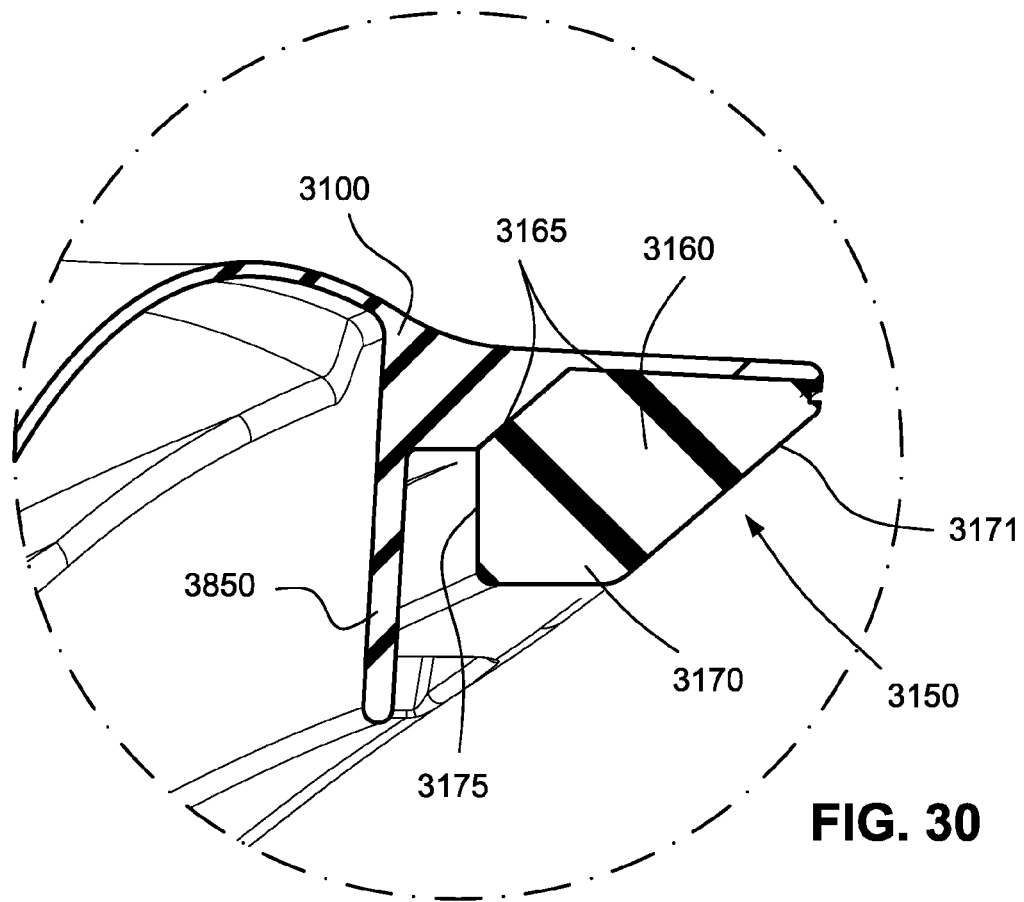

FIG. 30 is an enlarged portion of the cross-section shown in FIG. 29.

Figure 31:
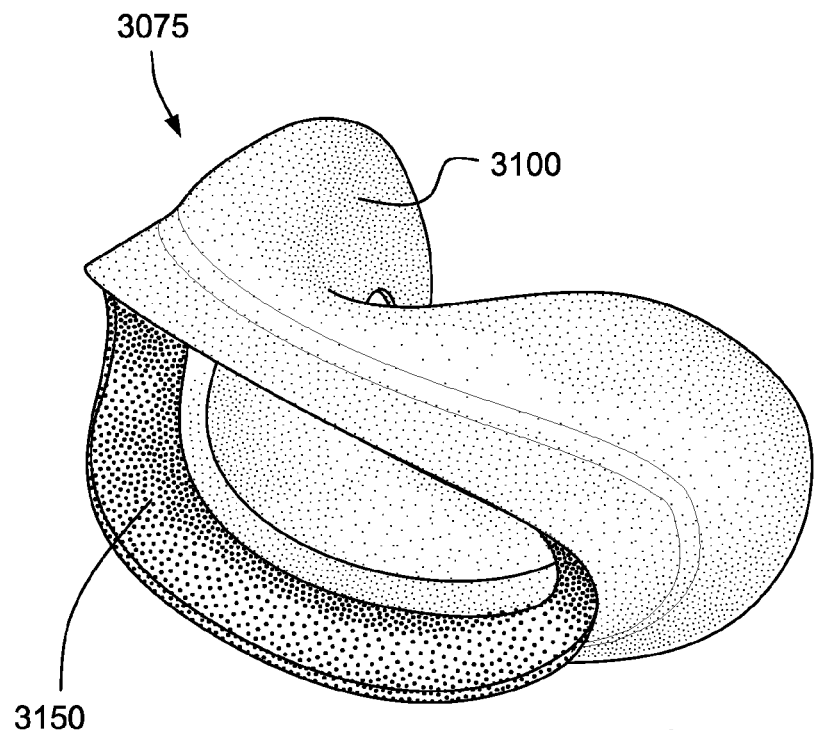

FIG. 31 is a perspective view of a cushion assembly of the patient interface shown in FIG. 7.

Figure 32:
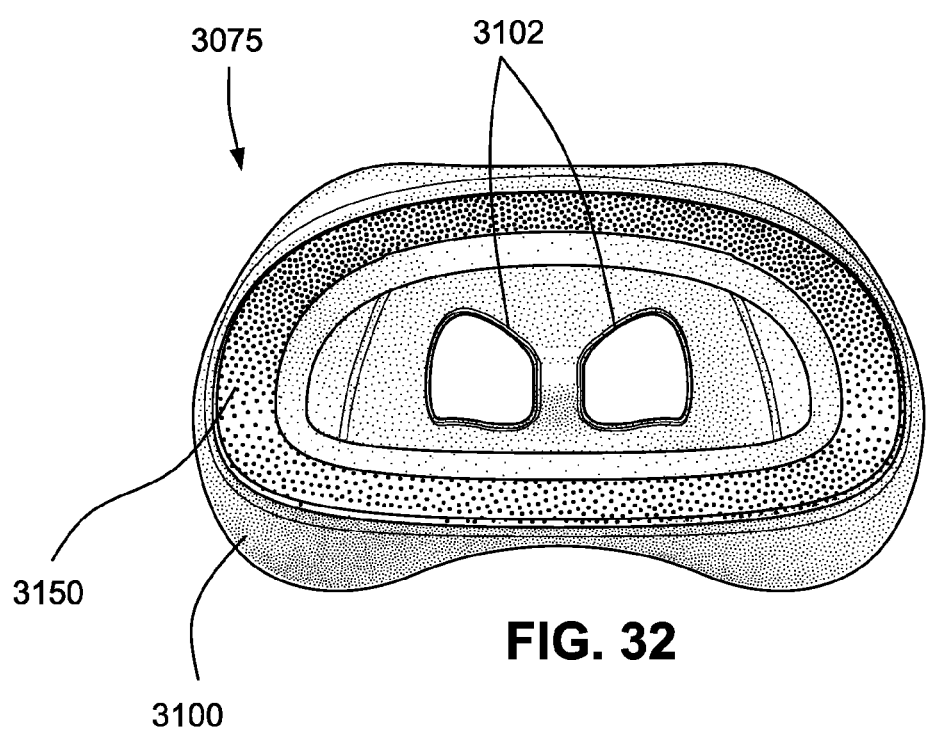

FIG. 32 is a front view of the cushion assembly shown in FIG. 31.

Figure 33:
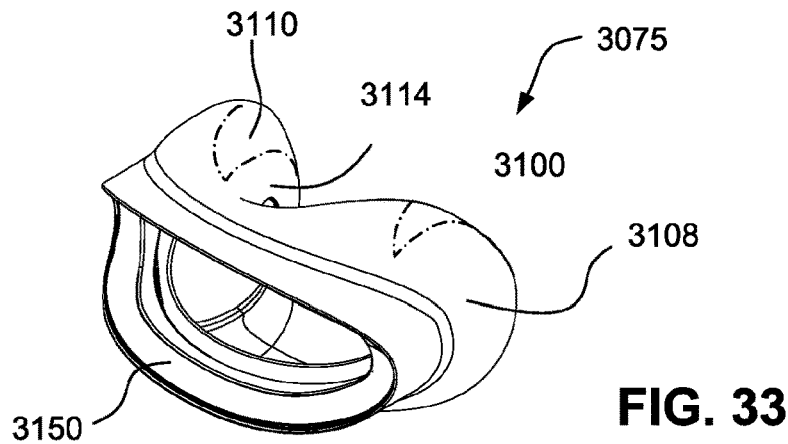

FIG. 33 is a perspective view of a cushion assembly of the patient interface shown in FIG. 7.

Figure 34:
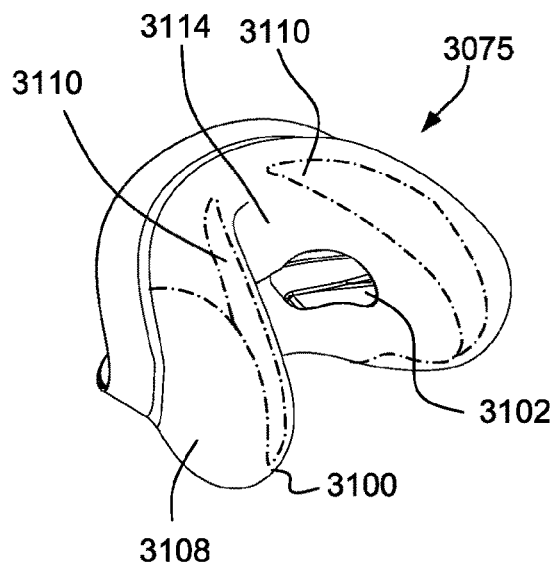

FIG. 34 is another perspective view of the cushion assembly shown in FIG. 33.

Figure 35:
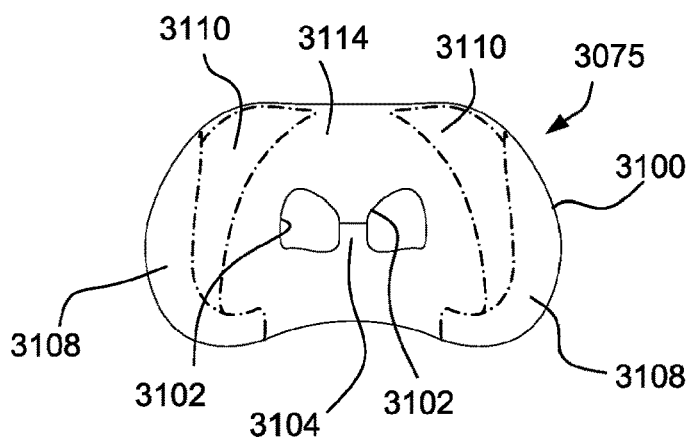

FIG. 35 is a rear view of the cushion assembly shown in FIG. 33.

Figure 36:
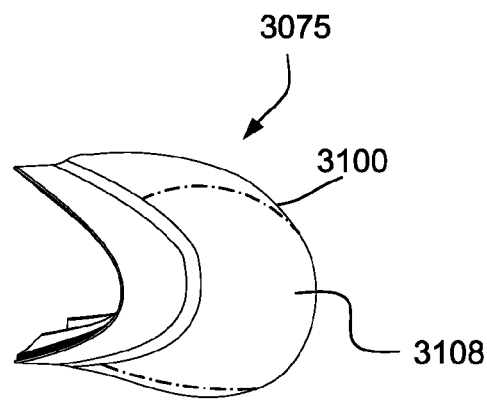

FIG. 36 is a side view of the cushion assembly shown in FIG. 33.

Figure 37:
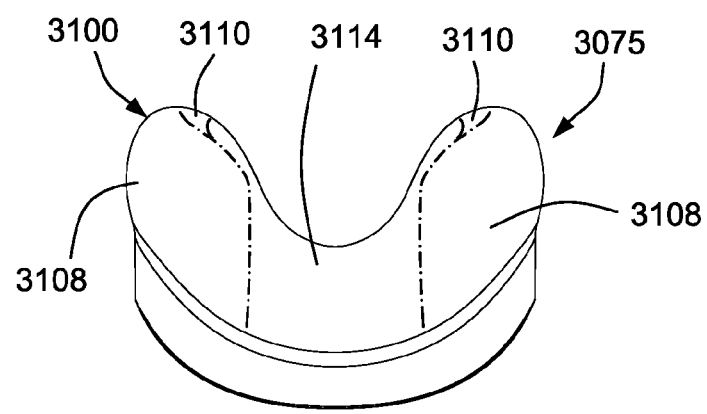

FIG. 37 is a bottom view of the cushion assembly shown in FIG. 33.

Figure 38:
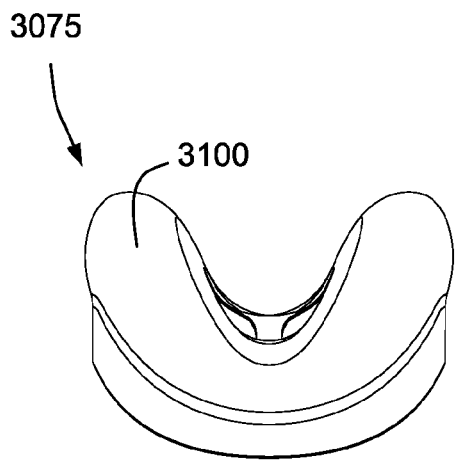

FIG. 38 is a top view of a cushion assembly for a patient interface according to an example of the present technology.

Figure 39:
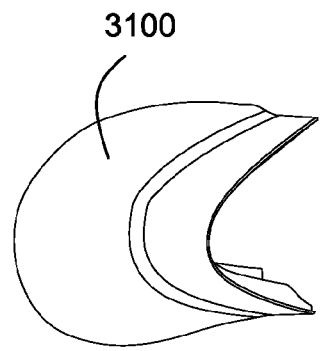

FIG. 39 is a side view of the cushion assembly of FIG. 38.

Figure 40:
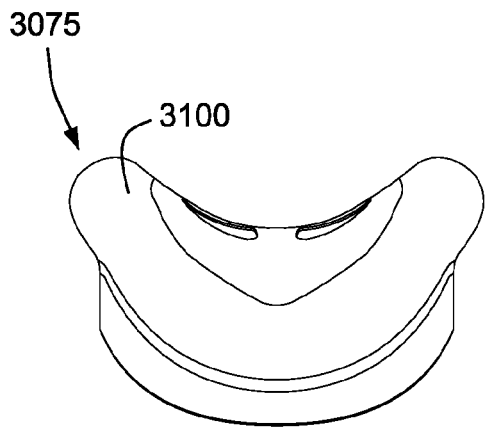

FIG. 40 is a top view of a cushion assembly for a patient interface according to an example of the present technology.

Figure 41:
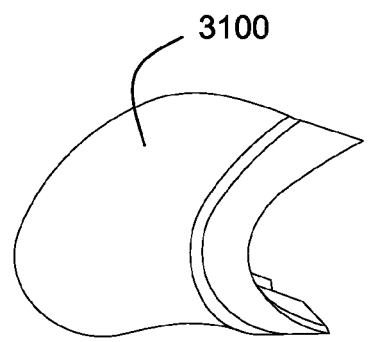

FIG. 41 is a side view of the cushion assembly of FIG. 40.

Figure 42:
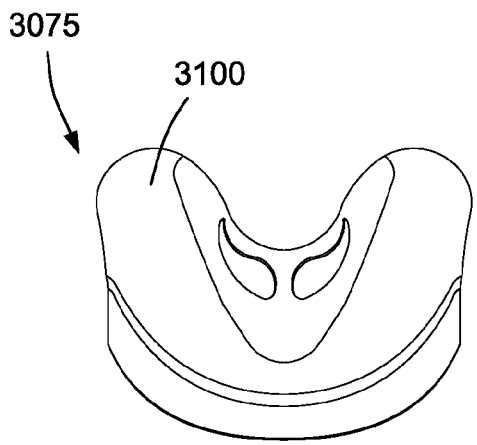

FIG. 42 is a top view of a cushion assembly for a patient interface according to an example of the present technology.

Figure 43:
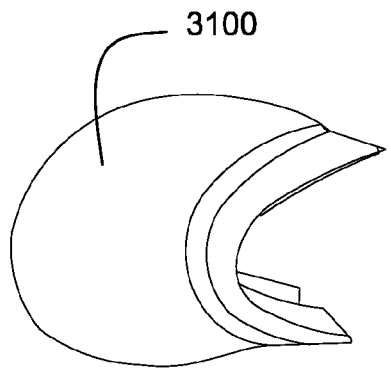

FIG. 43 is a side view of the cushion assembly of FIG. 42.

Figure 44A:
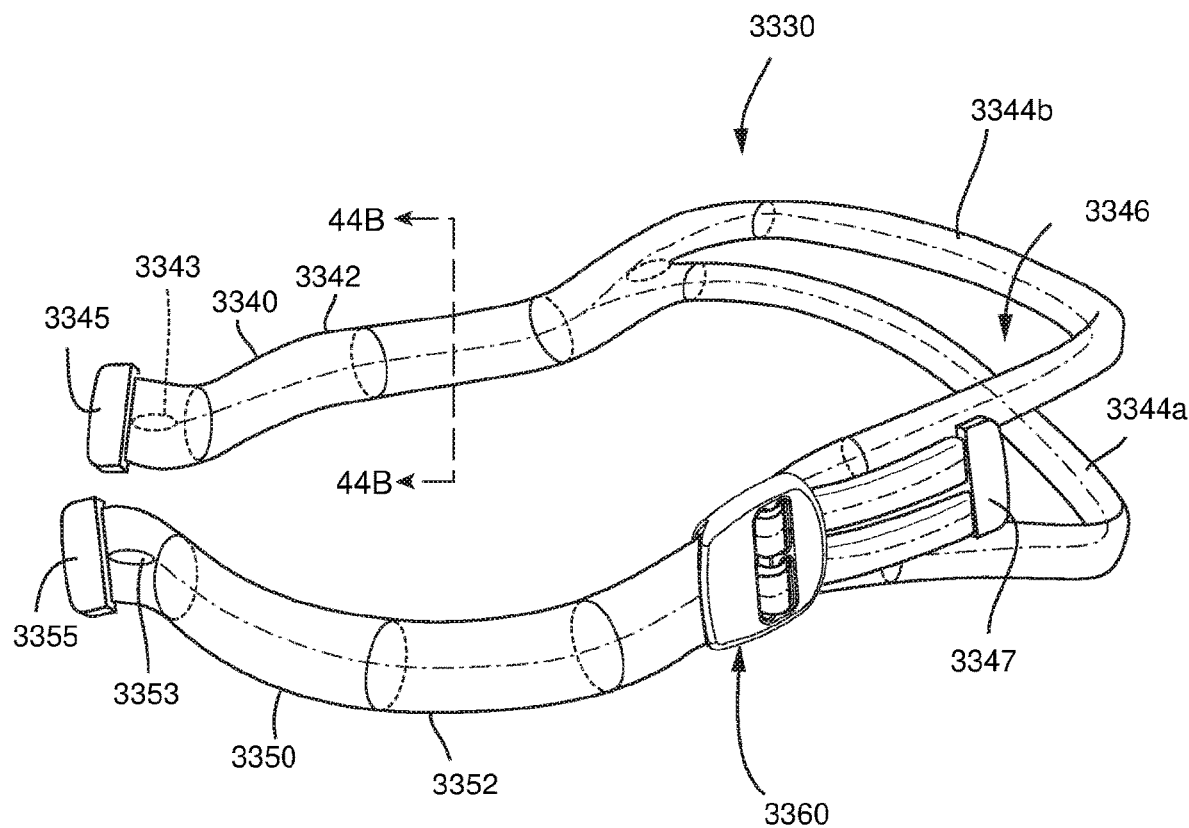

FIG. 44A is a schematic perspective view showing a headgear strap assembly of the patient interface of FIG. 4 according to an example of the present technology.

Figure 44B:
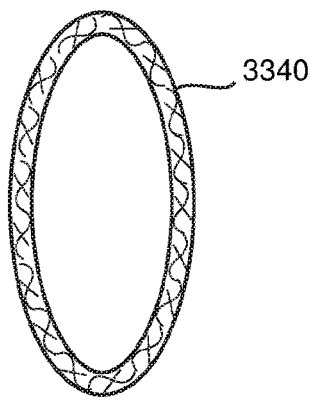

FIG. 44B shows a cross-section through line 44B-44B of FIG. 44A.

Figure 45:
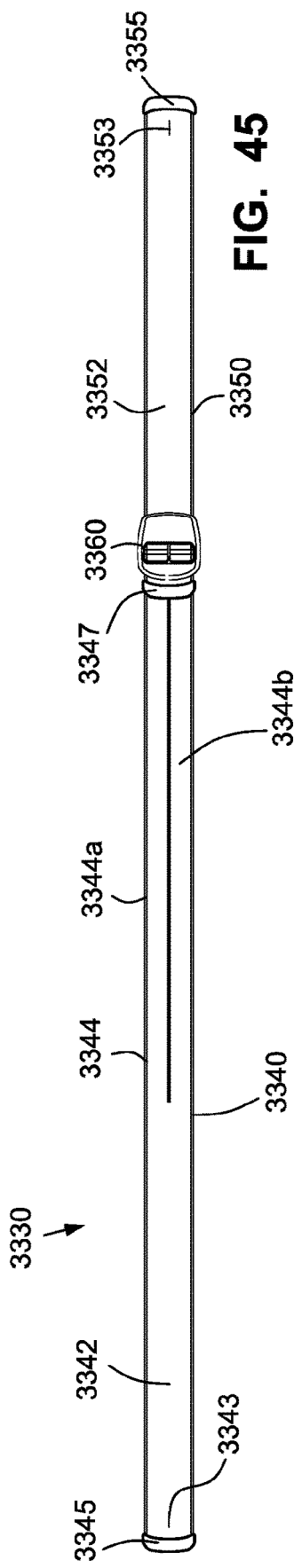

FIG. 45 is a top view of headgear strap assembly of the patient interface of FIG. 4 according to an example of the present technology.

Figure 46:
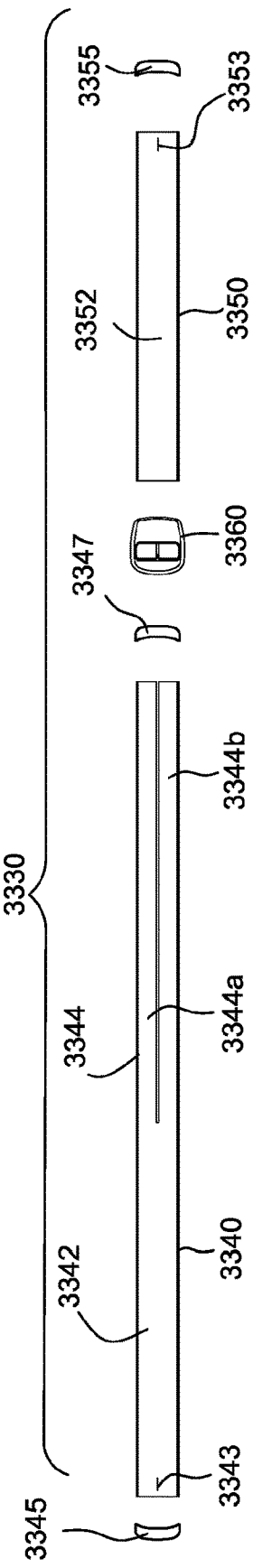

FIG. 46 is an exploded view of the headgear strap assembly of FIG. 45.

Figure 47:
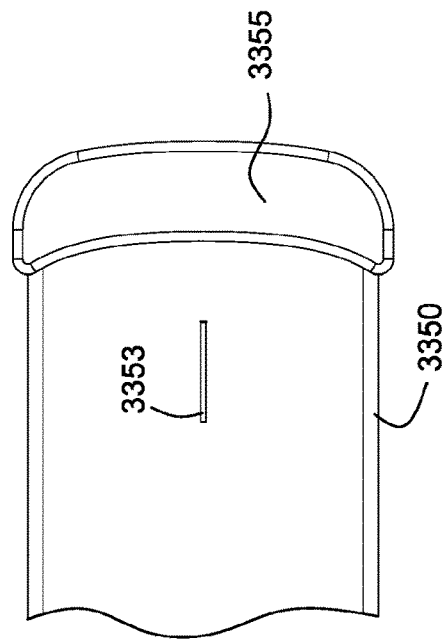

FIG. 47 is an enlarged view of an end of a strap portion of the headgear strap assembly of FIG. 45.

FIG. 48 is a perspective view of a buckle of the headgear strap assembly of FIG. 45.

FIG. 49 is a front view of the buckle of FIG. 48.

FIG. 50 is a top view of the buckle of FIG. 48.

Figure 51:
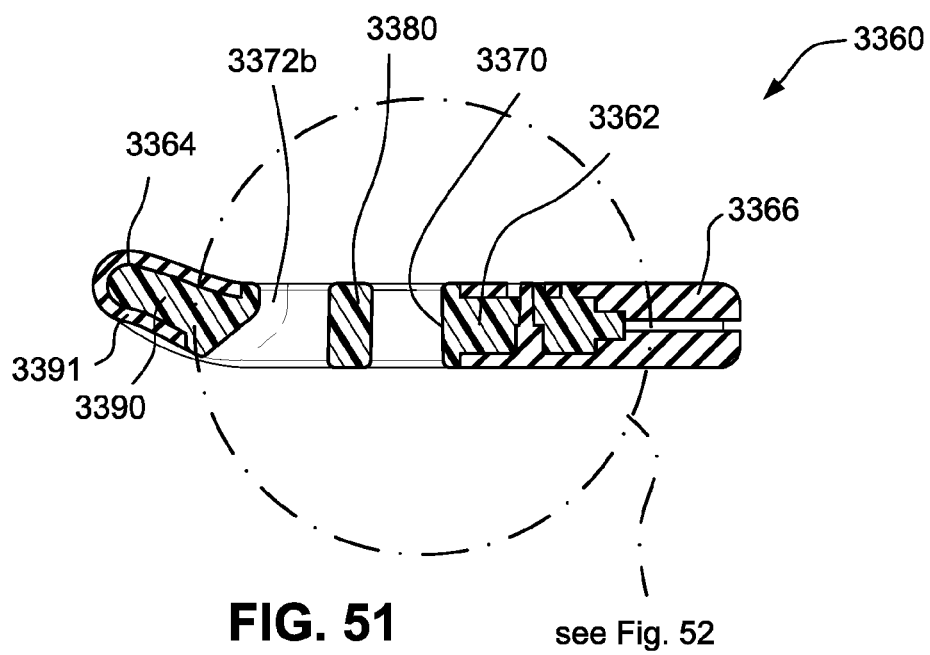

FIG. 51 is a cross-sectional view of the buckle of FIG. 48.

Figure 52:
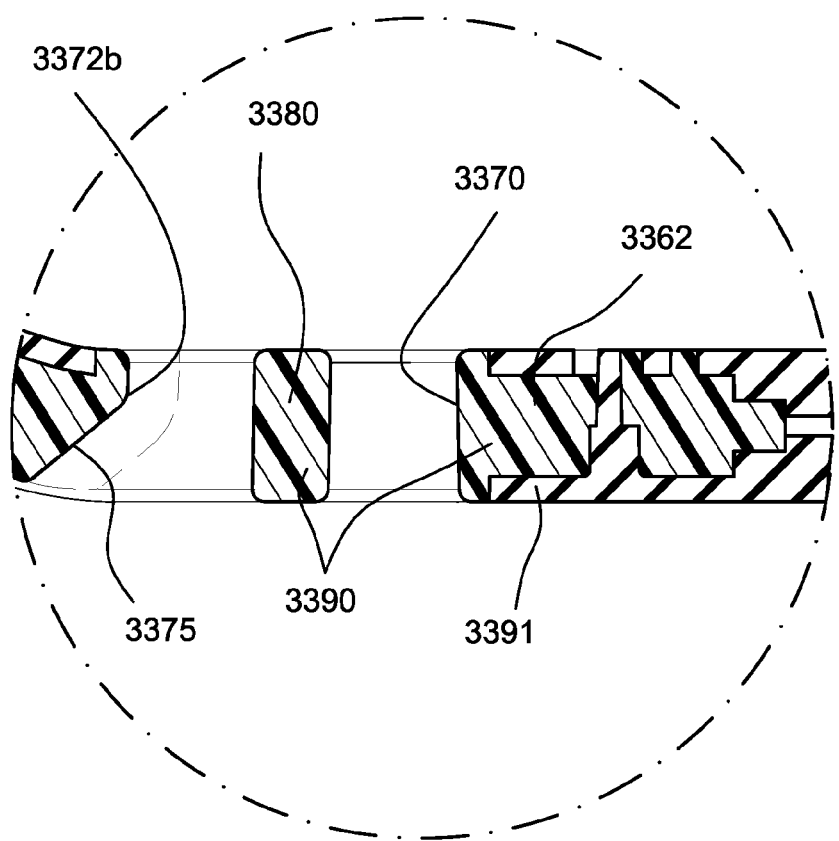

FIG. 52 is an enlarged portion of the cross-section shown in FIG. 51.

Figure 53:
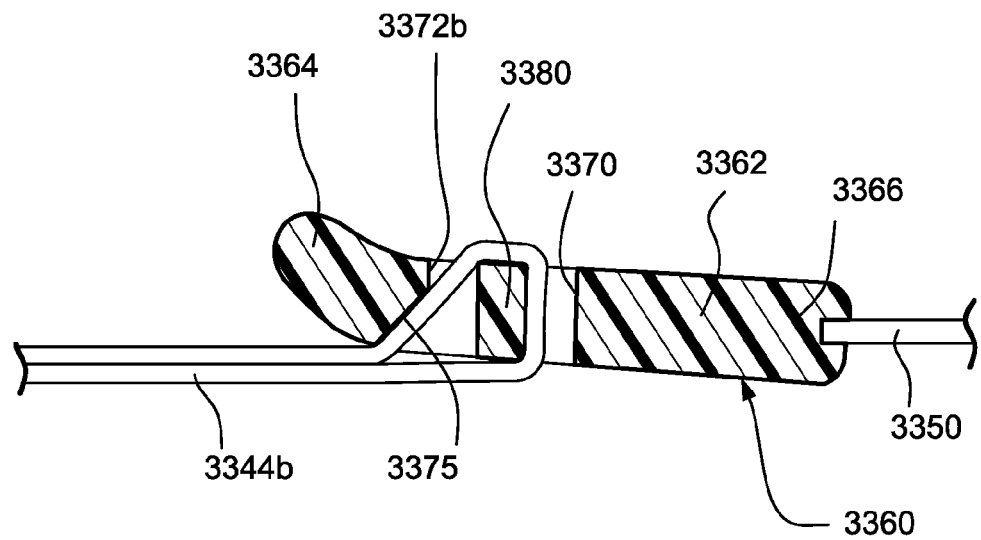
Figure 54:
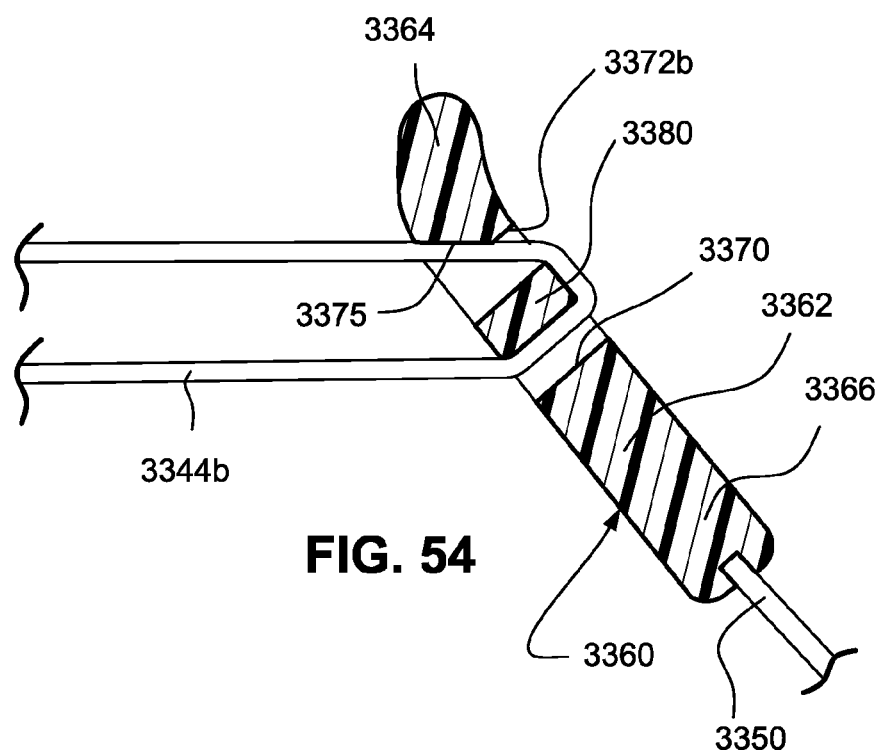

FIGS. 53 and 54 are cross-sectional views showing strap adjustment of the headgear strap assembly according to an example of the present technology.

Figure 55:
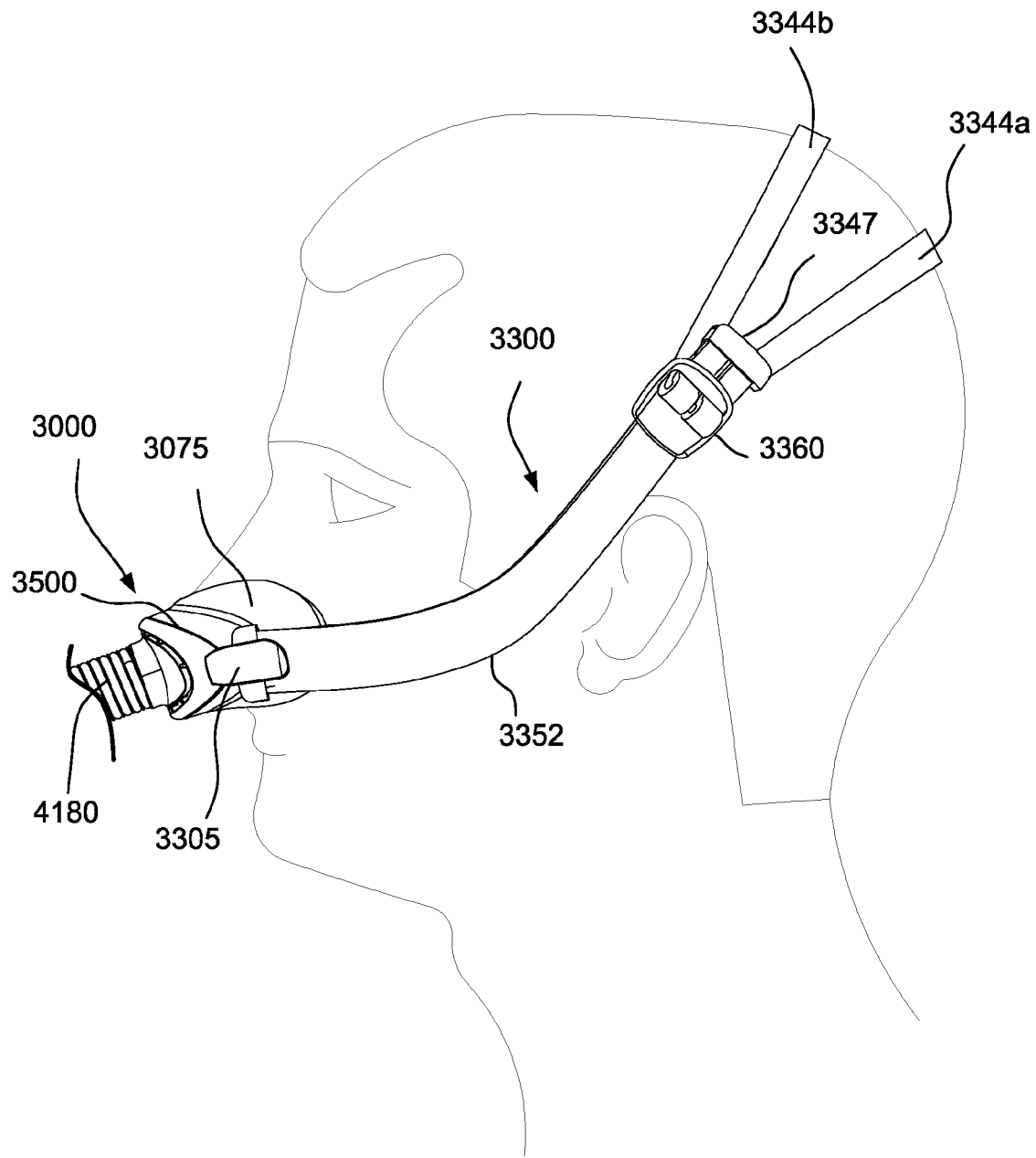

FIG. 55 is a side view of a patient interface shown on a patient's head according to an example of the present technology, the patient interface being shown with the headgear strap assembly in a first adjusted position.

Figure 56:
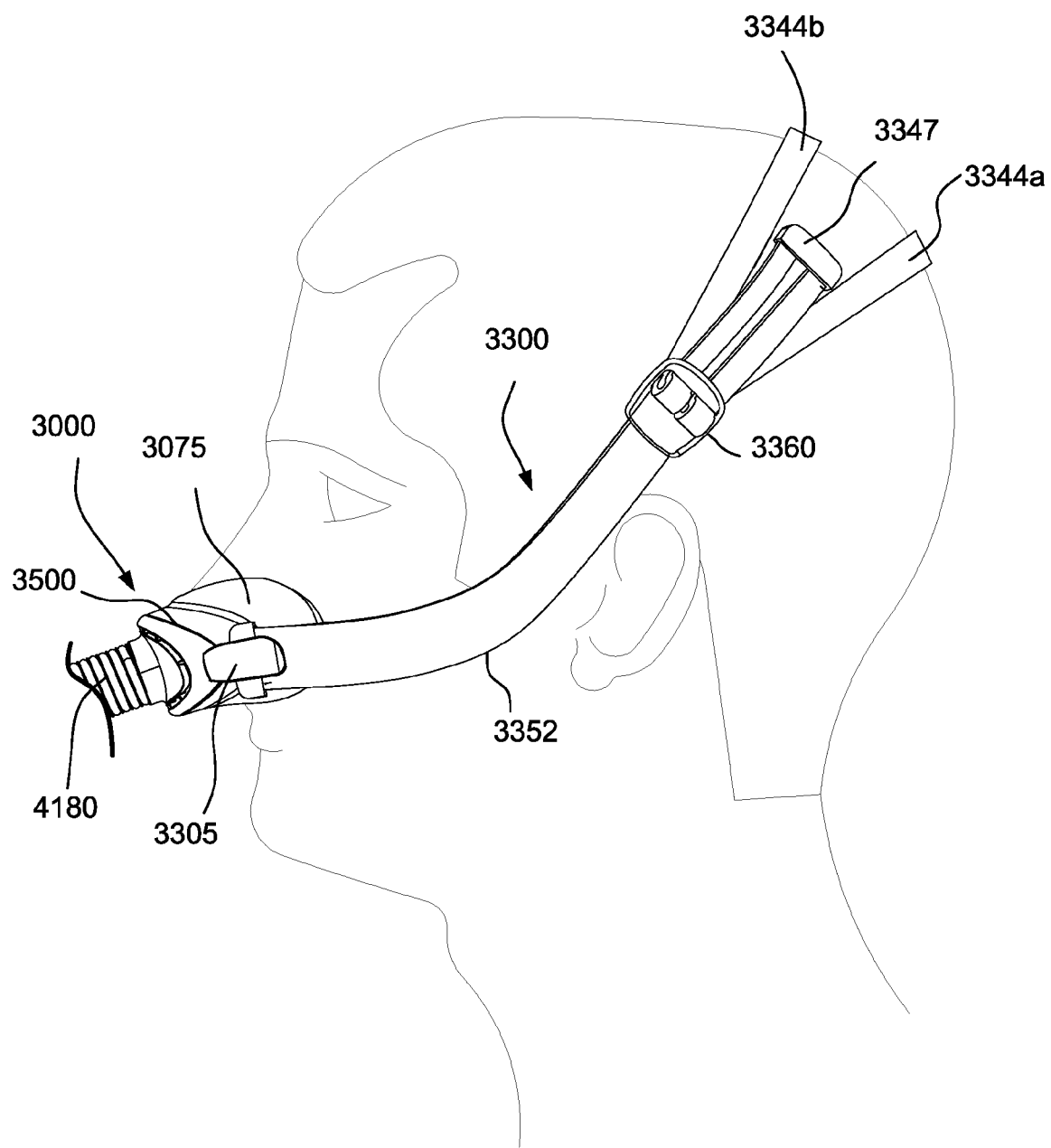

FIG. 56 is a side view of a patient interface shown on a patient's head according to an example of the present technology, the patient interface being shown with the headgear strap assembly in a second adjusted position.

Figure 57:
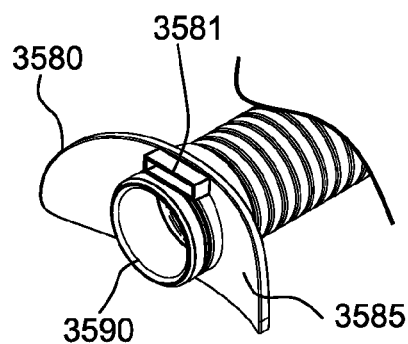

FIG. 57 is a perspective view showing a cover of a frame assembly of the patient interface according to an example of the present technology.

Figure 58:
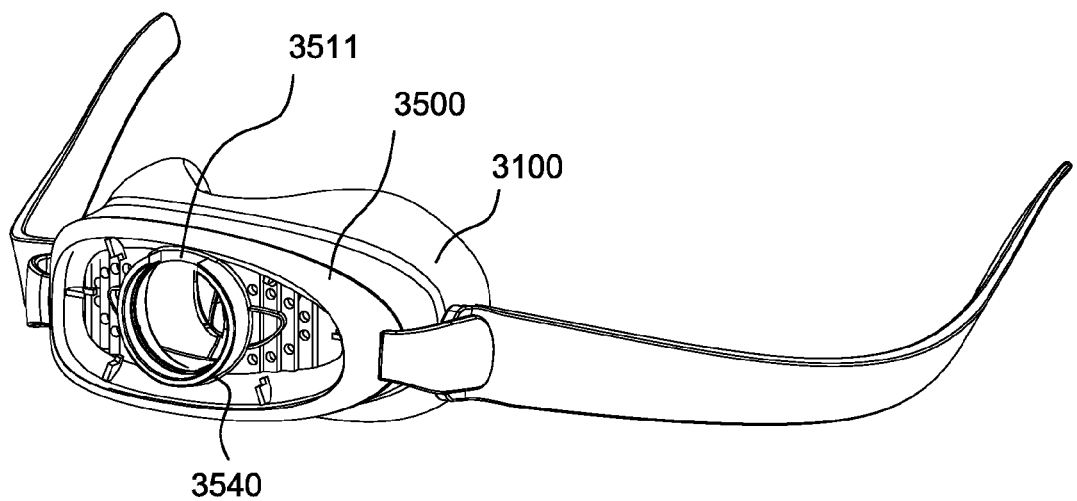

FIG. 58 is a perspective view showing a main body of a frame assembly of the patient interface according to an example of the present technology.

Figure 59:
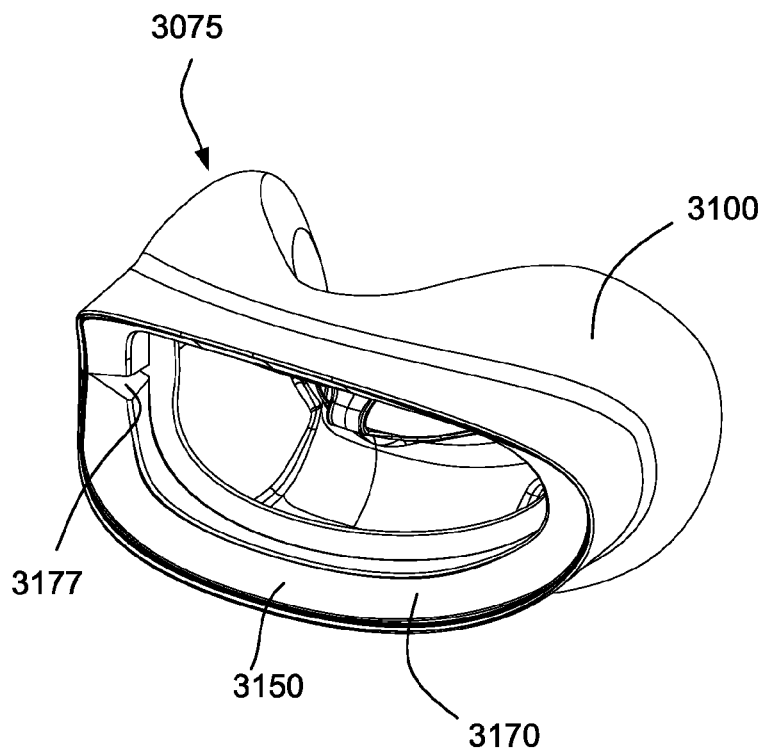

FIG. 59 is a perspective view of a cushion assembly for a patient interface according to an example of the present technology.

Figure 60:
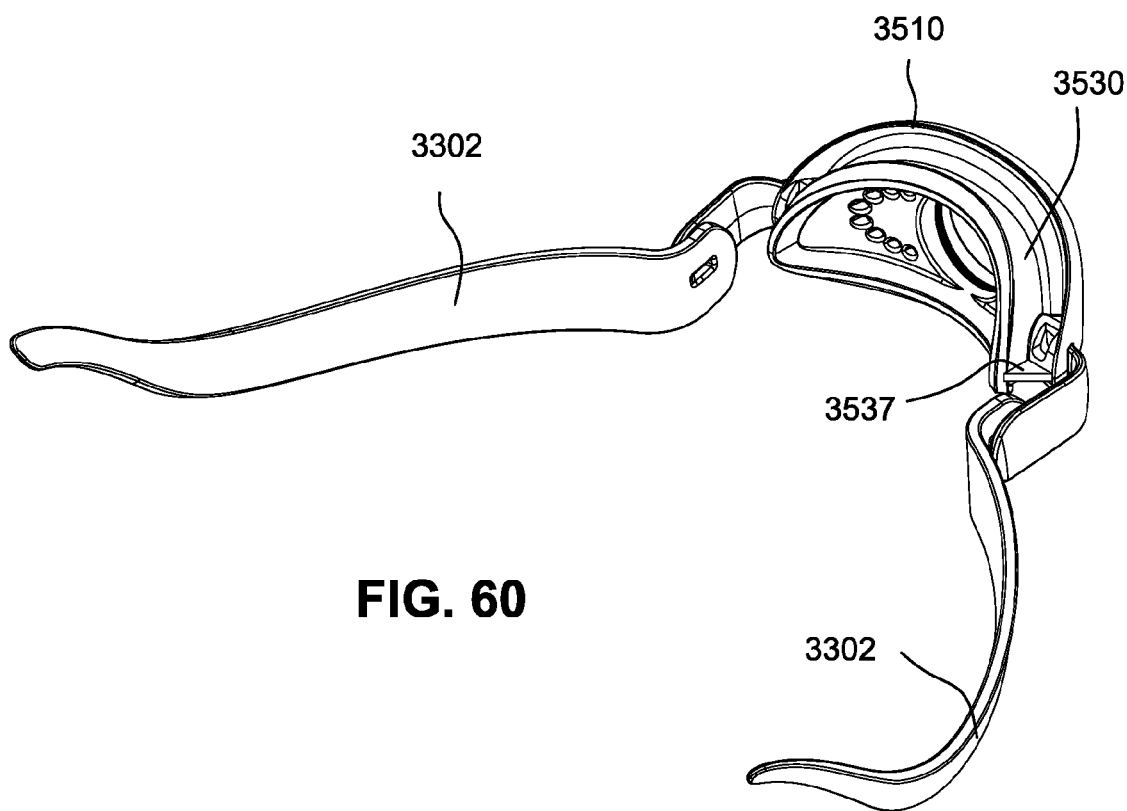

FIG. 60 is a perspective view showing a main body of a frame assembly of the patient interface according to an example of the present technology.

Figure 61:
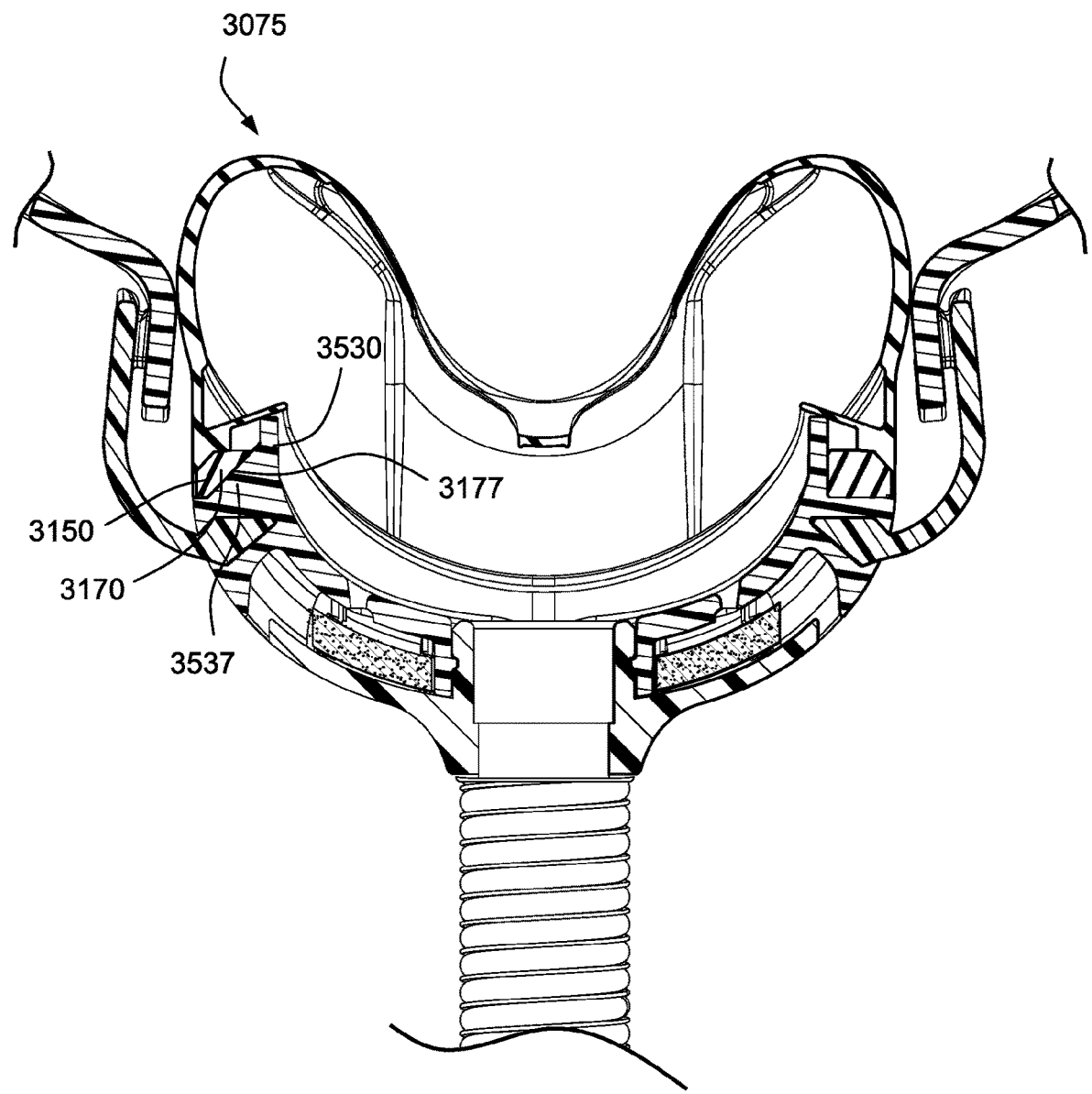

FIG. 61 is a cross-sectional view showing alignment features of the cushion assembly and the main body of the frame assembly of the patient interface according to an example of the present technology.

FIG. 62 is a top view of a cushion assembly for a patient interface according to an example of the present technology.

FIG. 63 is a bottom view of the cushion assembly of FIG. 62.

FIG. 64 is a perspective view of the cushion assembly of FIG. 62.

FIG. 65 is another perspective view of the cushion assembly of FIG. 62.

Figure 66:
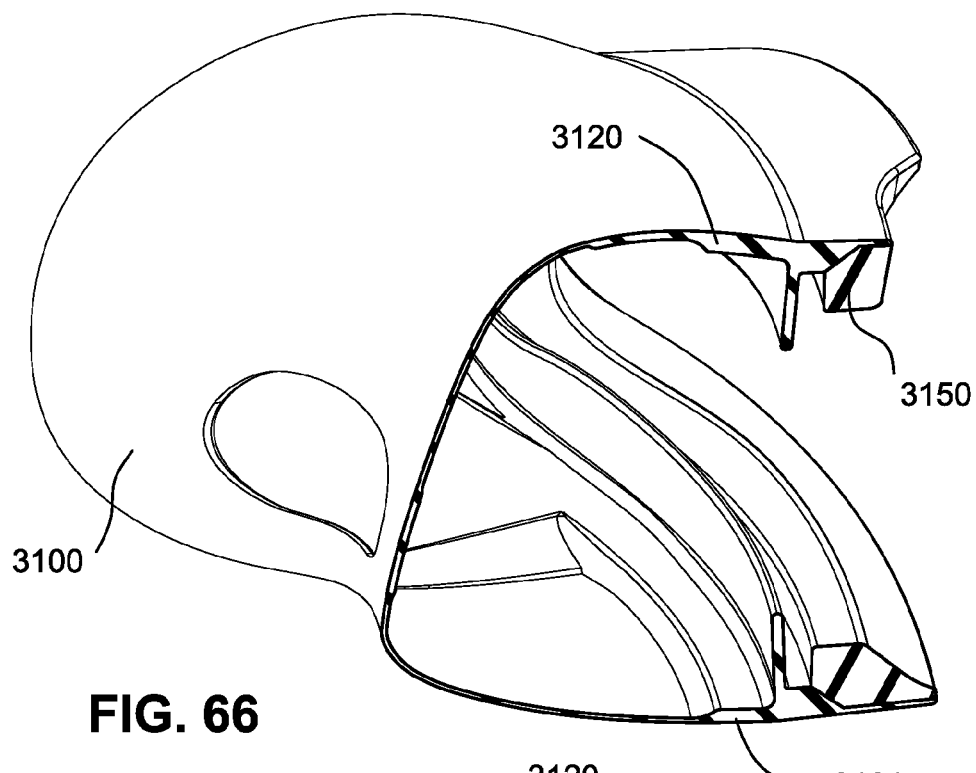

FIG. 66 is a cross-sectional view of the cushion assembly of FIG. 62.

Figure 67:
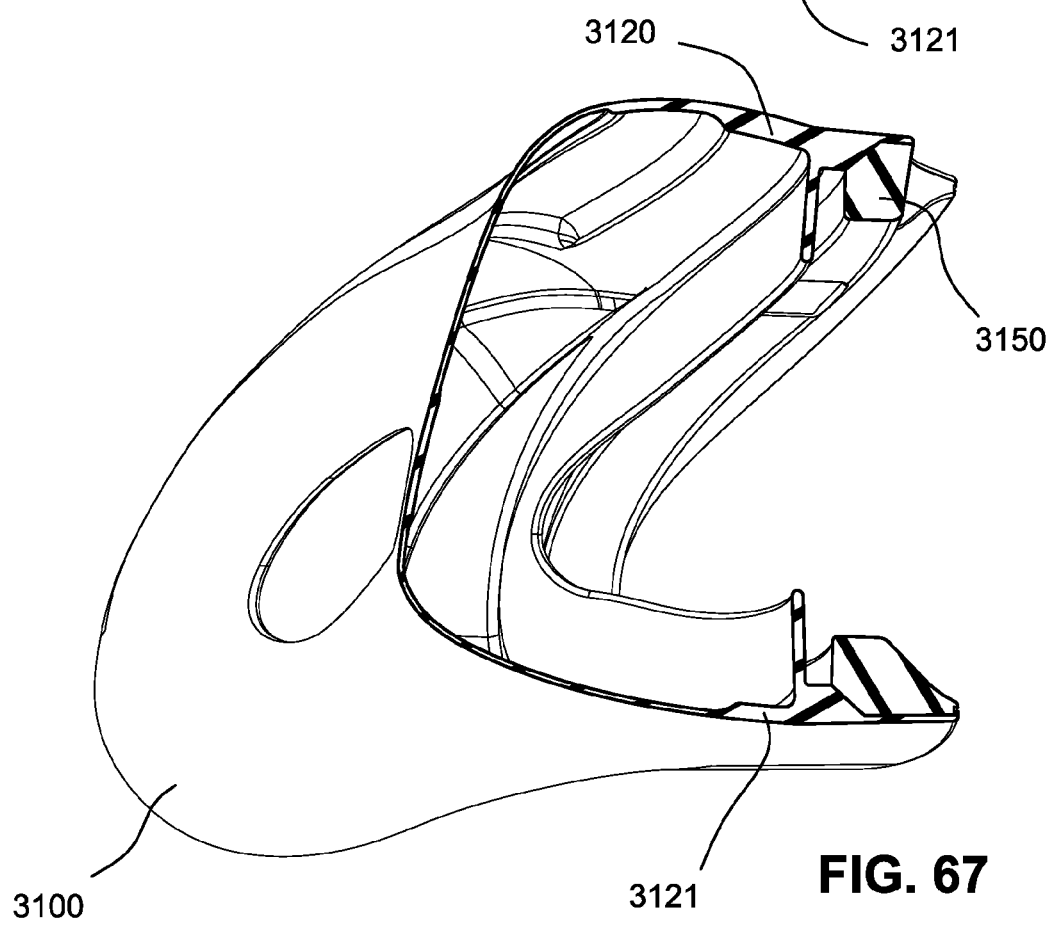

FIG. 67 is another cross-sectional view of the cushion assembly of FIG. 62.

FIG. 68 is a top view of a cushion assembly for a patient interface according to an example of the present technology.

FIG. 69 is a bottom view of the cushion assembly of FIG. 68.

FIG. 70 is a perspective view of the cushion assembly of FIG. 68.

FIG. 71 is another perspective view of the cushion assembly of FIG. 68.

Figure 72:
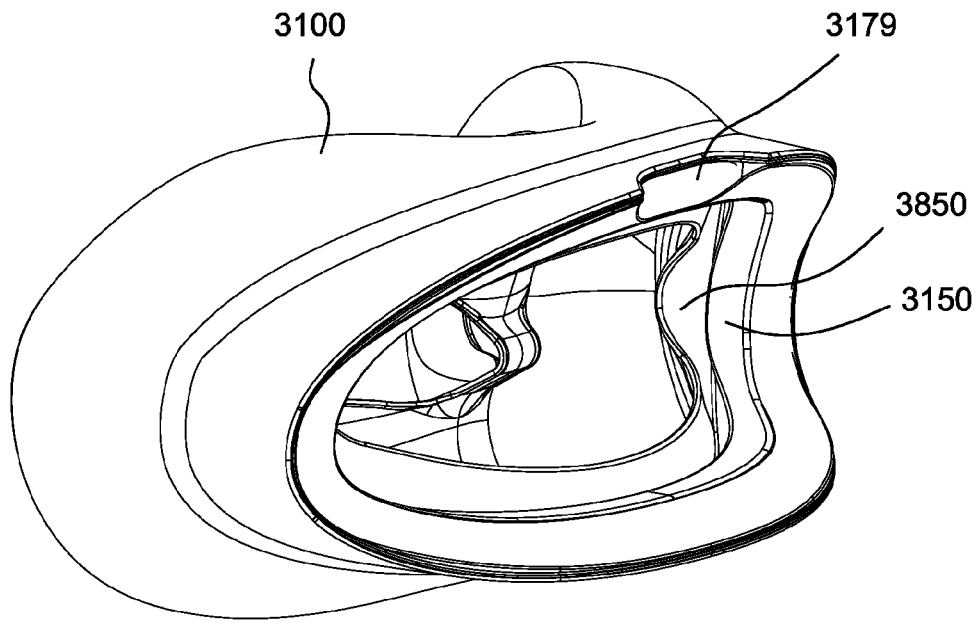

FIG. 72 is a perspective view of a cushion assembly for a patient interface according to an example of the present technology.

Figure 73:
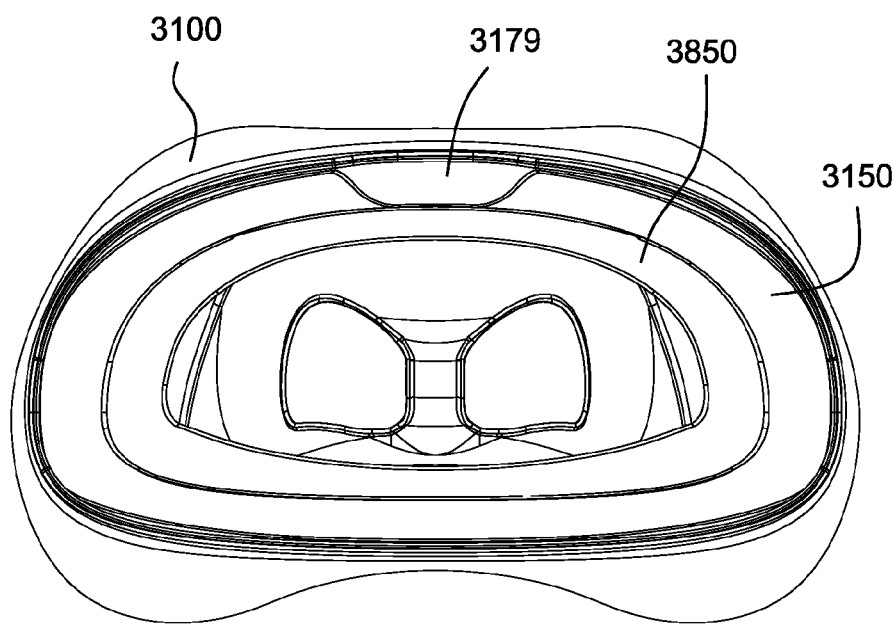

FIG. 73 is a front view of the cushion assembly shown in FIG. 72.

Figure 74:
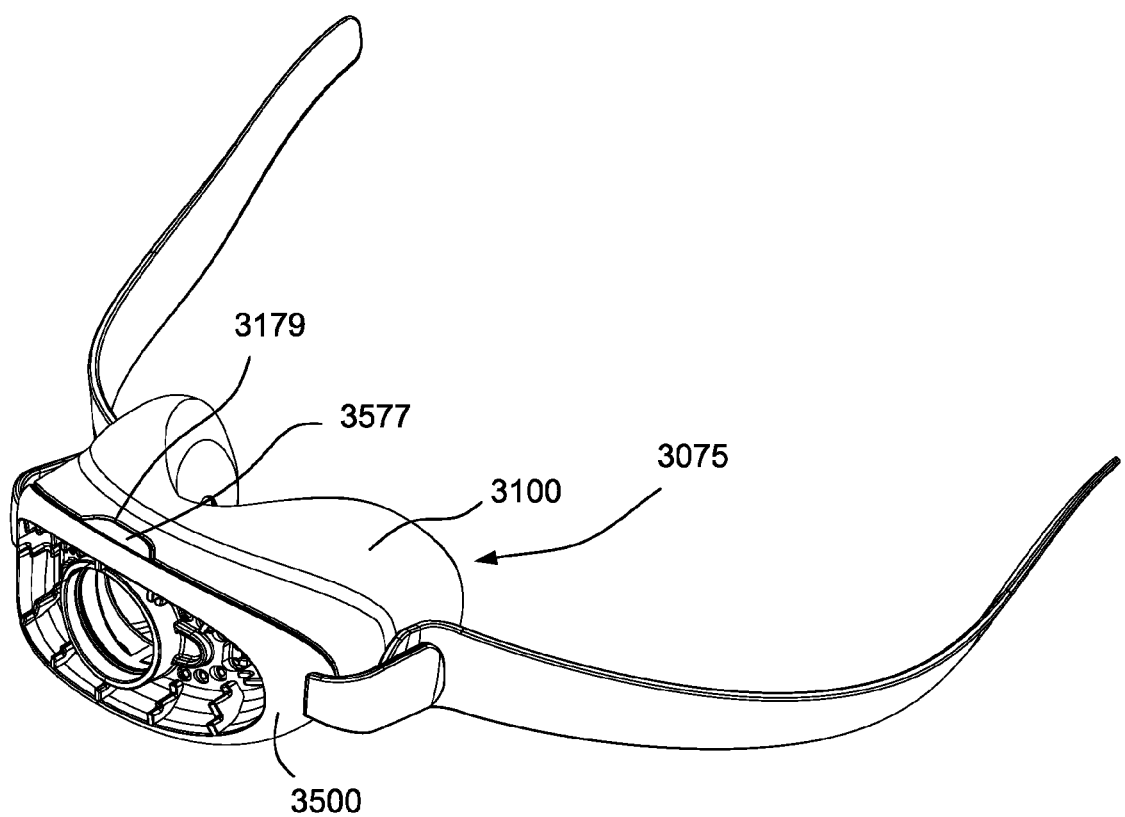

FIG. 74 is a perspective view of the cushion assembly shown in FIG. 72 connected to the main body of a frame assembly according to an example of the present technology.

Figure 75:
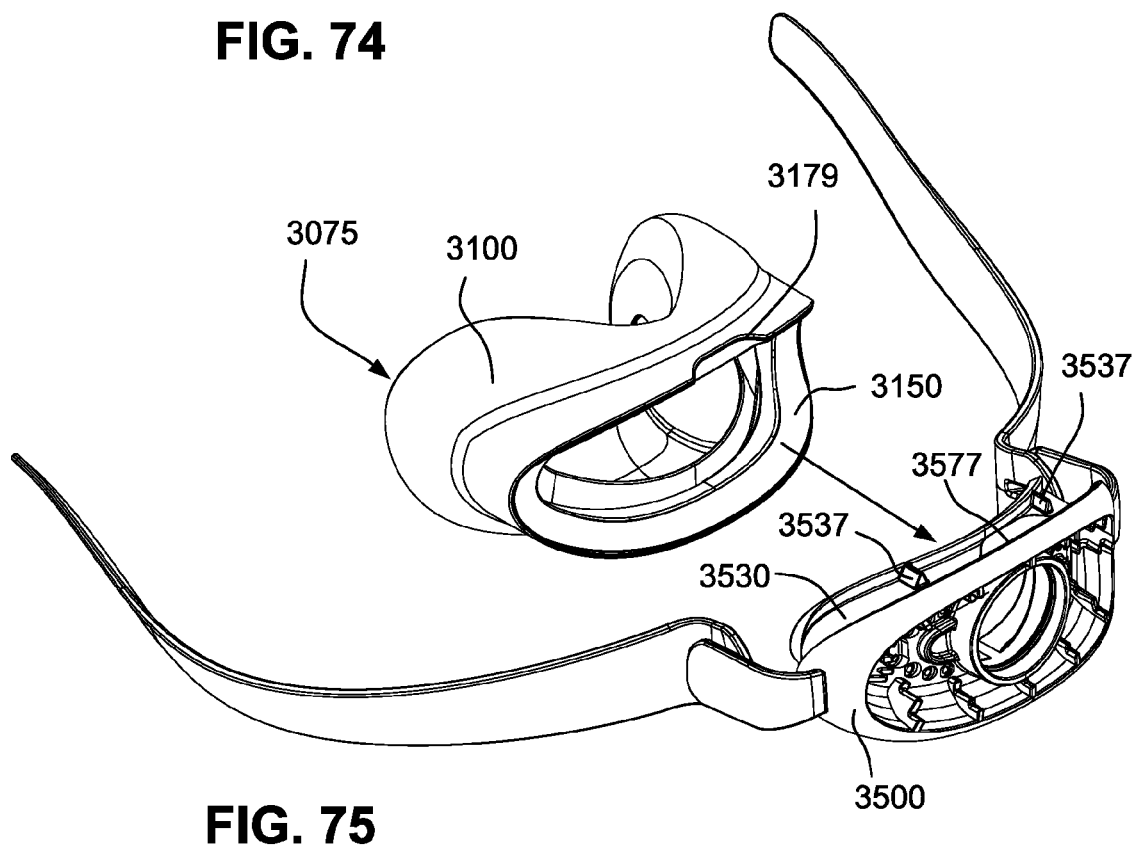

FIG. 75 is an exploded view of the cushion assembly and the main body of the frame assembly shown in FIG. 74.

Figure 76:
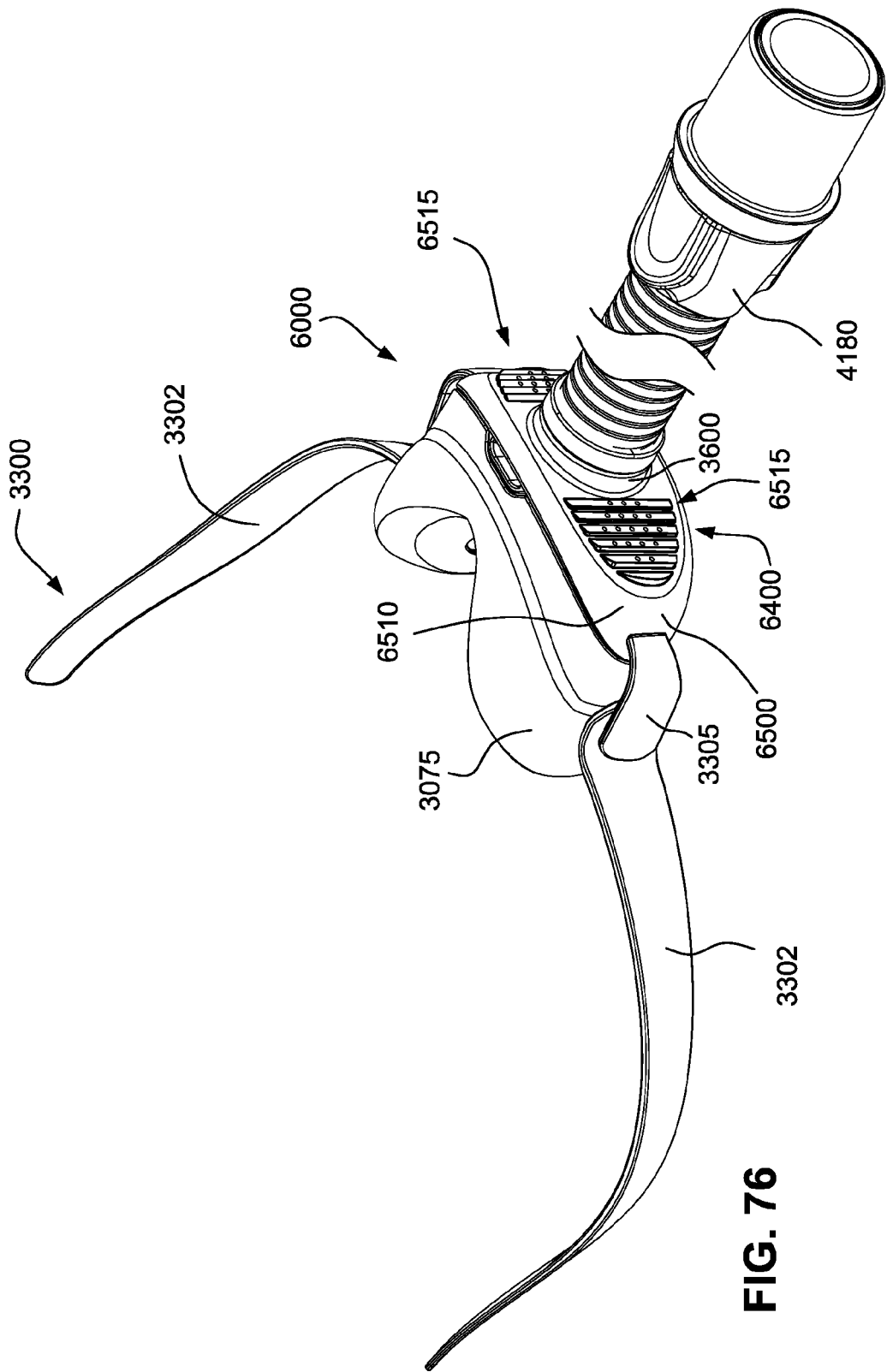

FIG. 76 is a perspective view of a patient interface according to another example of the present technology, the patient interface being shown with a headgear strap assembly removed.

Figure 77:
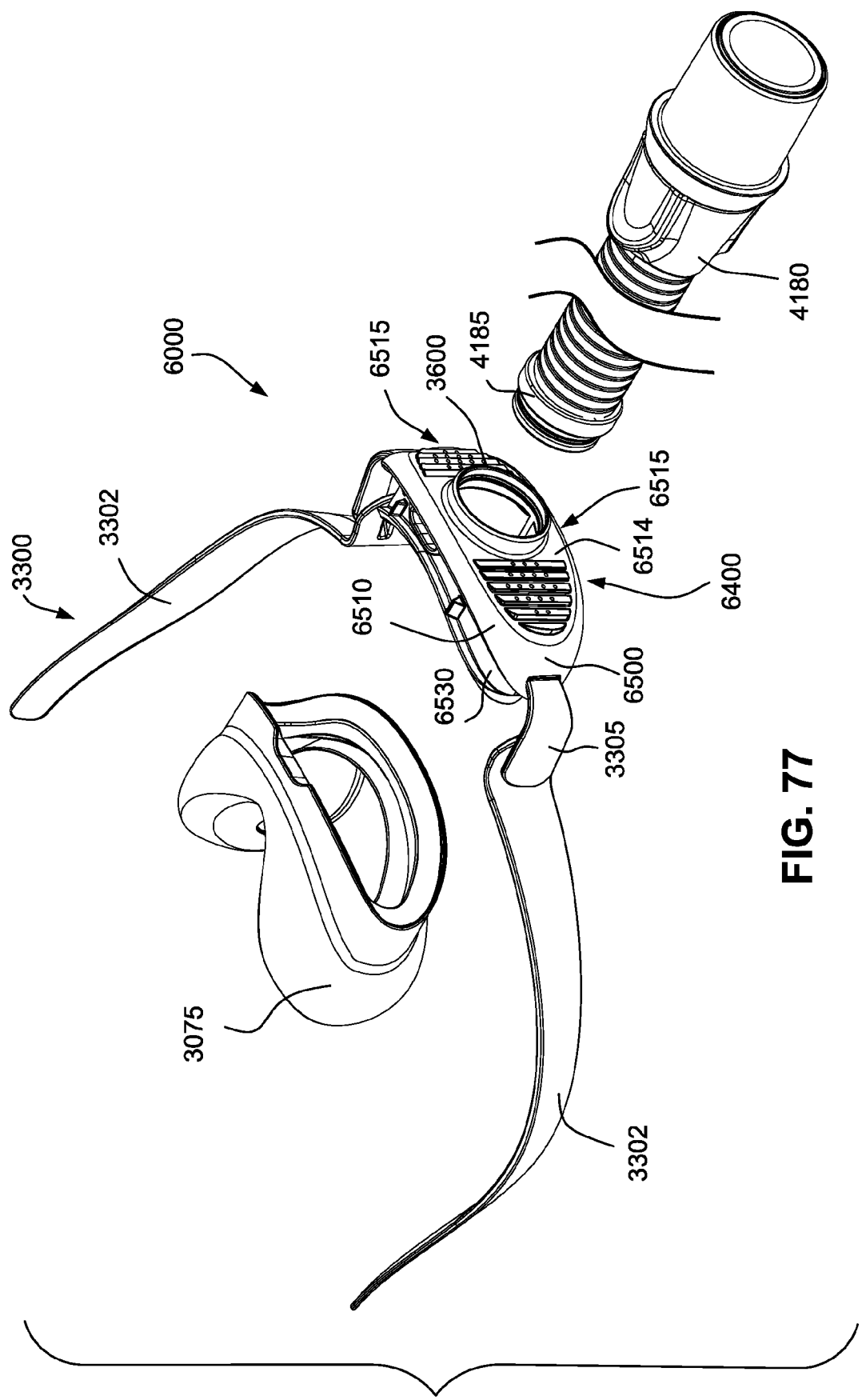

FIG. 77 is an exploded view when viewed from the front of the patient interface shown in FIG. 76.

Figure 78:
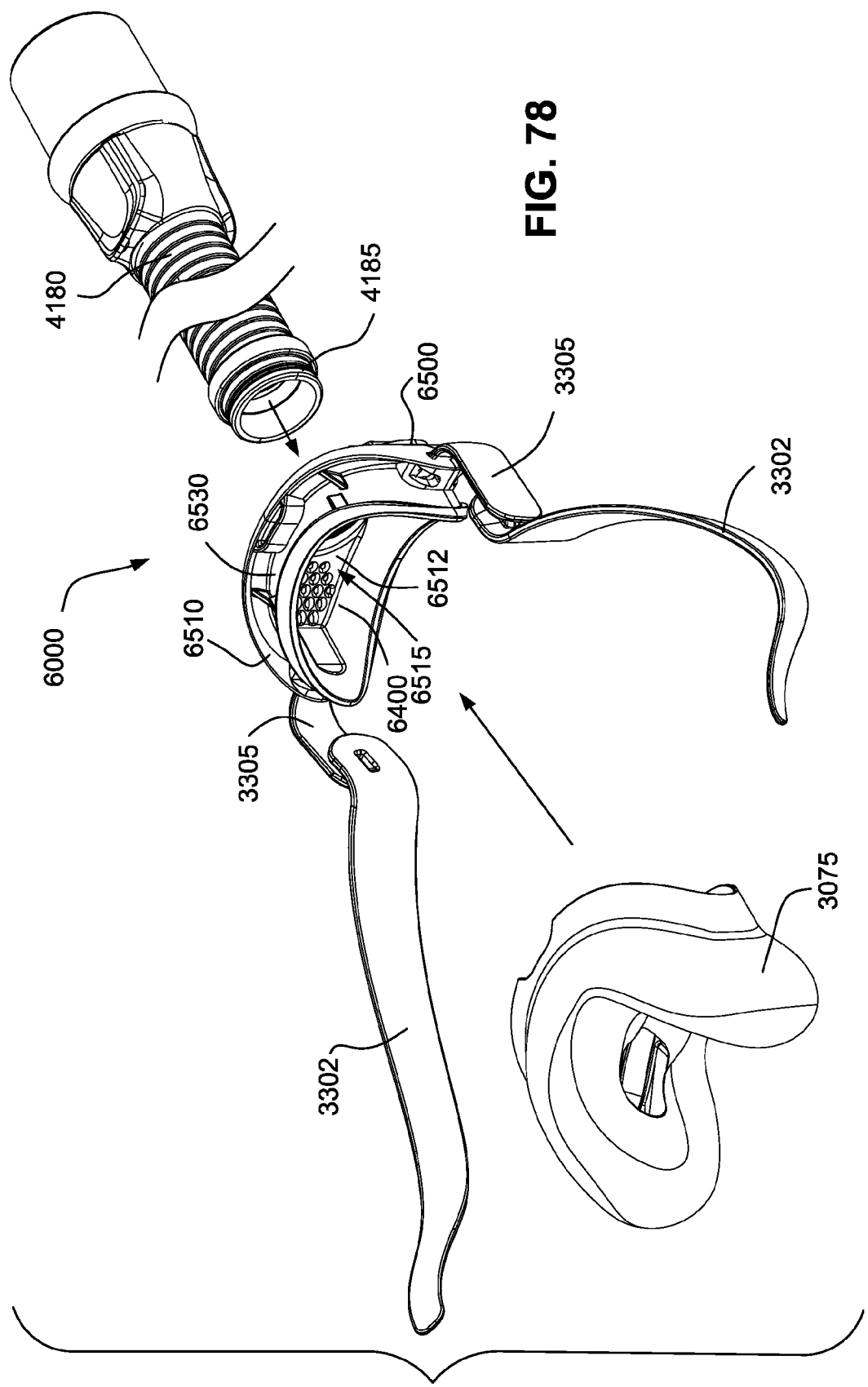

FIG. 78 is an exploded view when viewed from the rear of the patient interface shown in FIG. 76.

Figure 79:
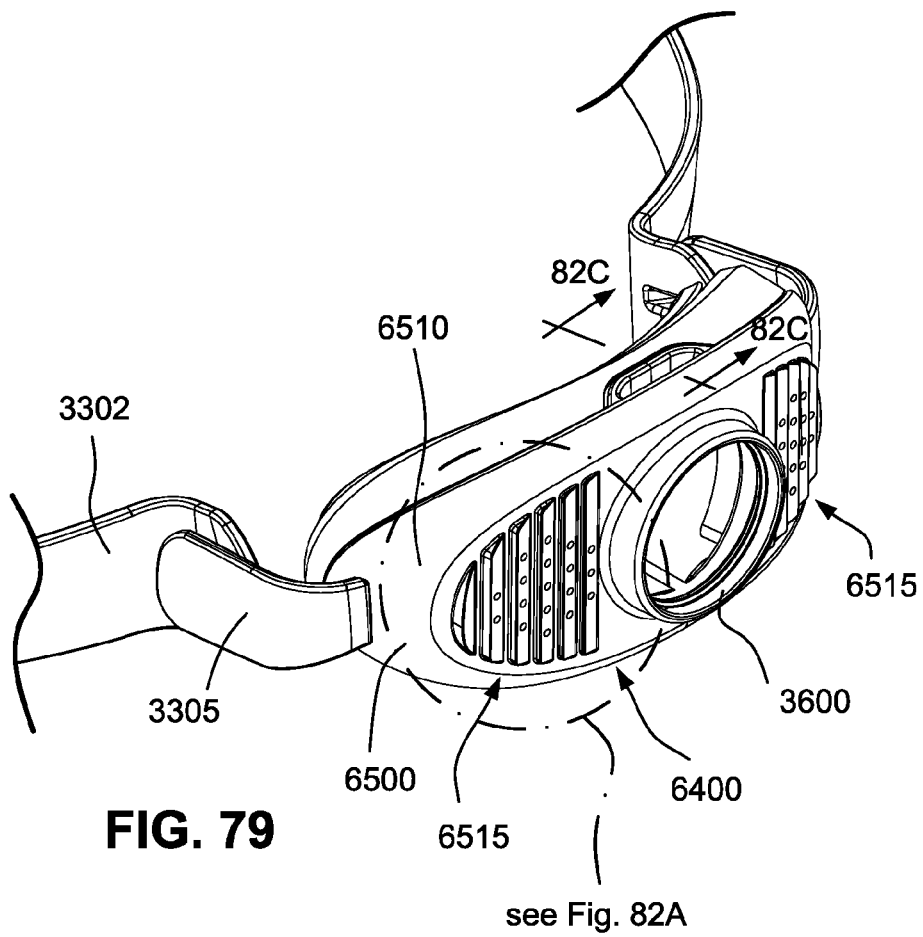

FIG. 79 is a perspective view showing the frame assembly of the patient interface shown in FIG. 76 according to an example of the present technology.

Figure 80:
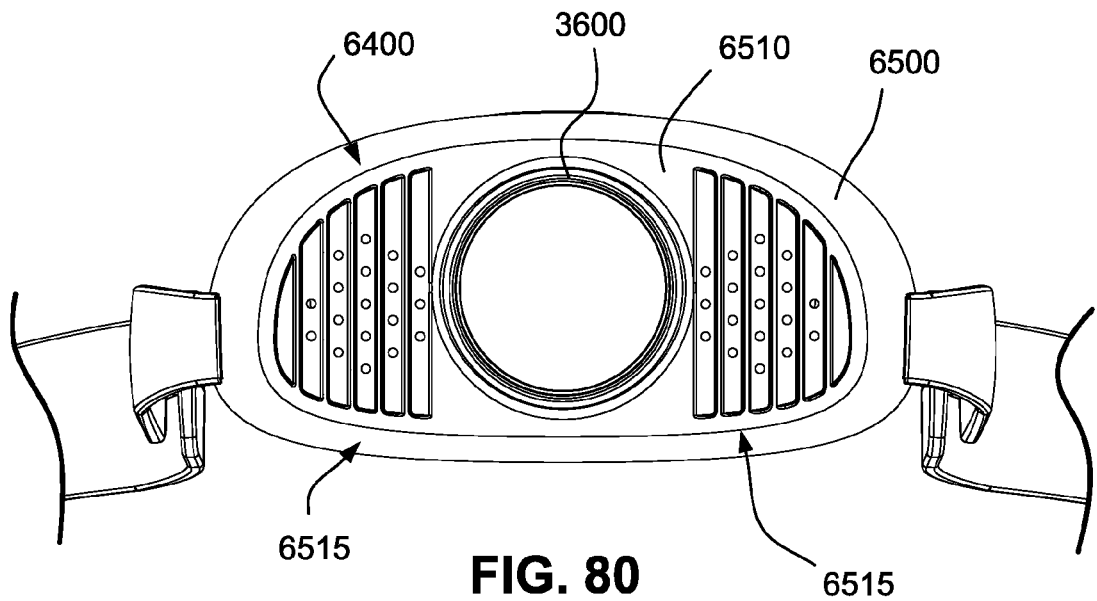

FIG. 80 is a front view of the frame assembly shown in FIG. 79.

Figure 81:
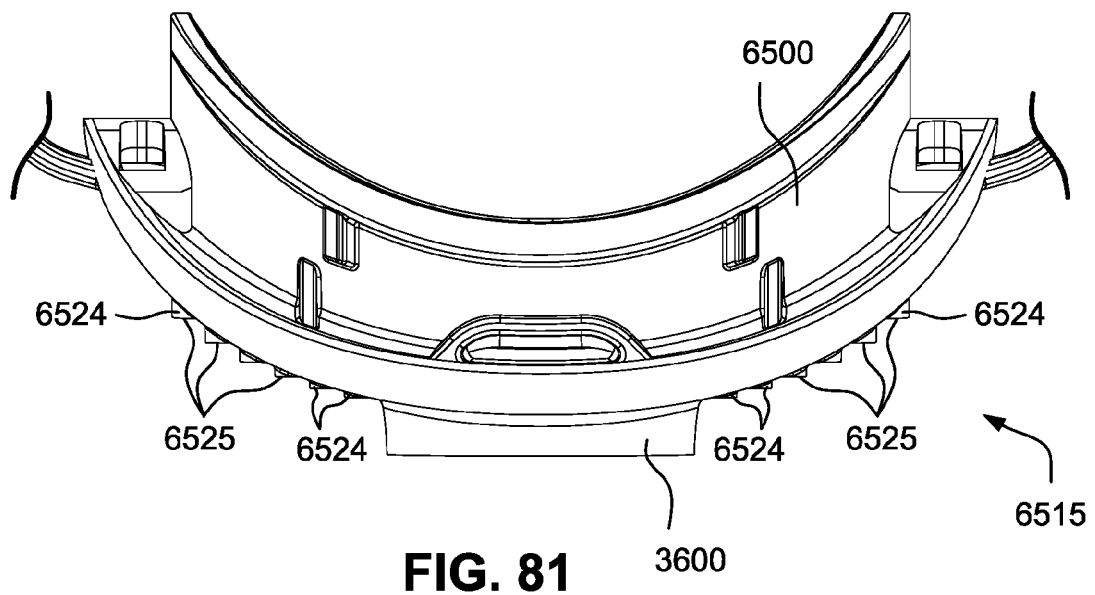

FIG. 81 is a top view of the frame assembly shown in FIG. 79.

Figure 82A:
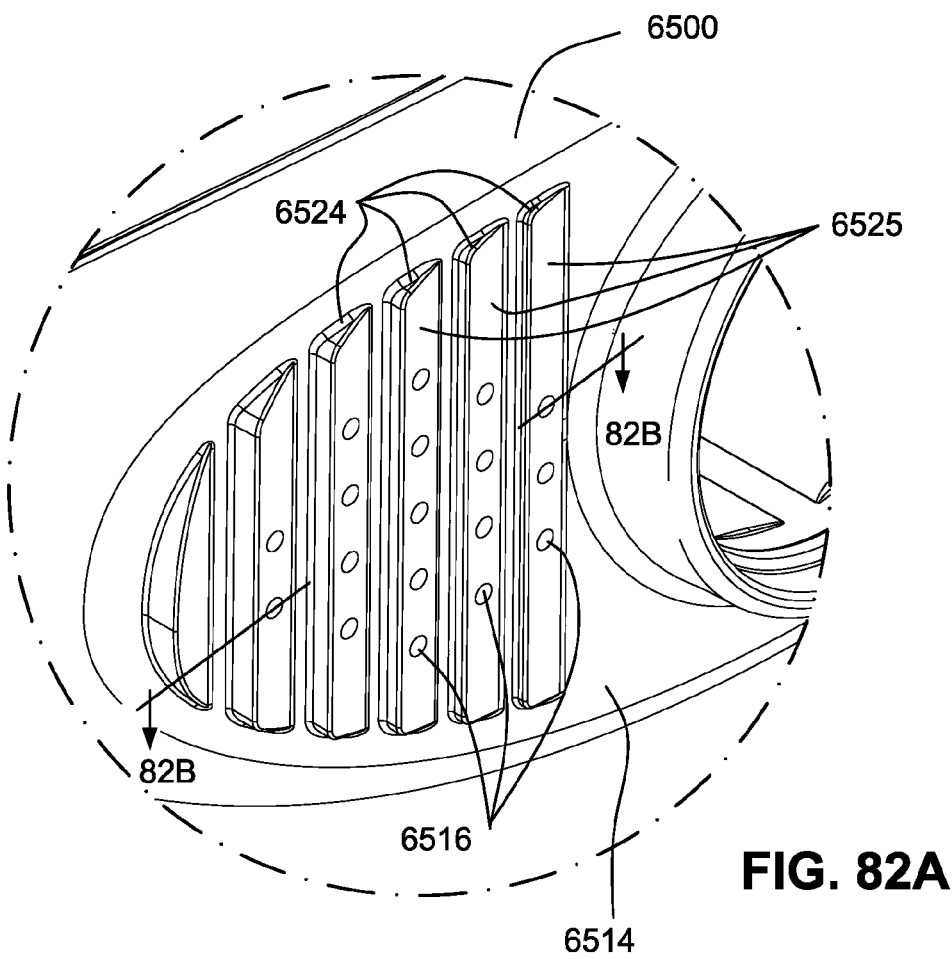

FIG. 82A is an enlarged portion of the frame assembly shown in FIG. 79.

Figure 82B:
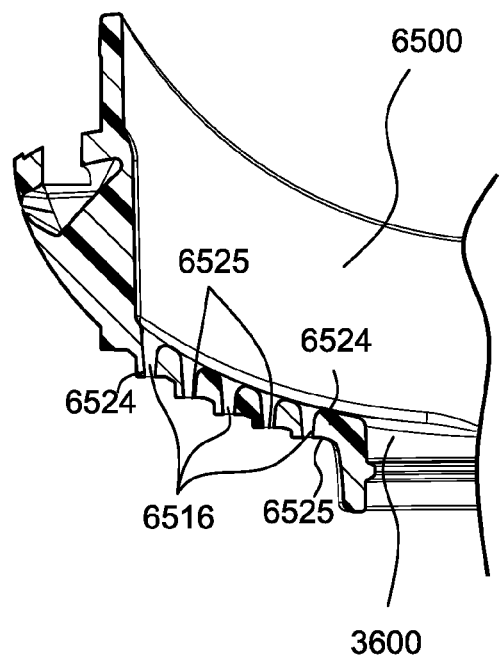

FIG. 82B is a cross-sectional view of the frame assembly shown in FIG. 82A.

Figure 82C:
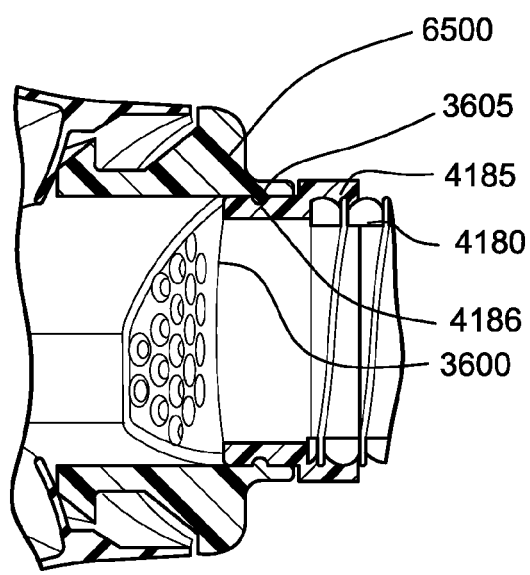

FIG. 82C is a cross-sectional view of the patient interface shown in FIG. 79.

FIG. 83A to 83D are various views showing fitting of the patient interface according to an example of the present technology.

Figure 84A:
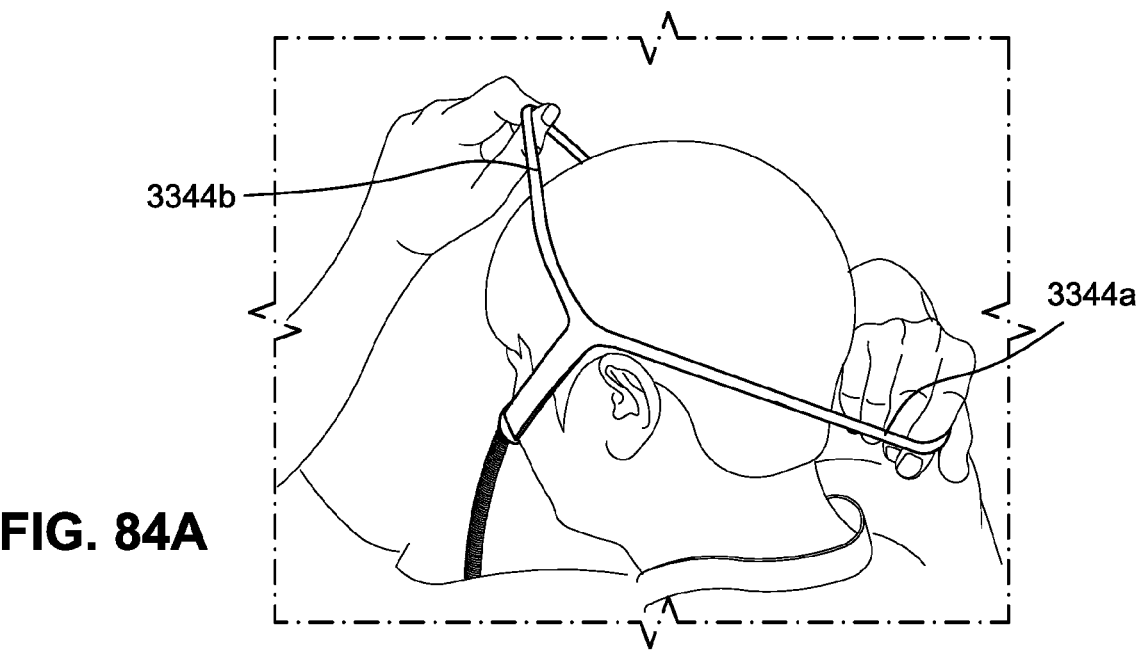
Figure 84B:
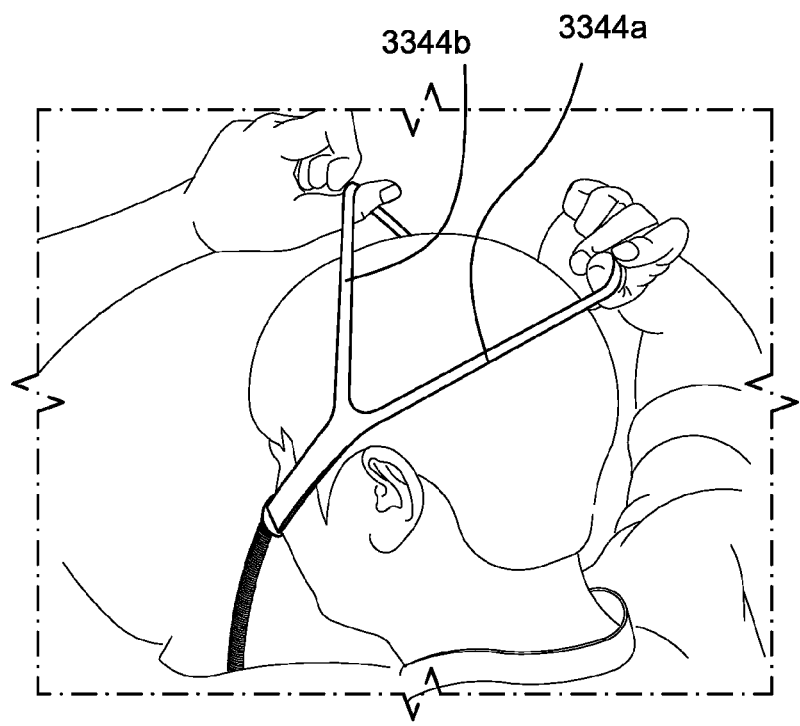

FIGS. 84A and 84B are various views showing adjusting of the headgear strap assembly of the patient interface according to an example of the present technology.

Figure 85:
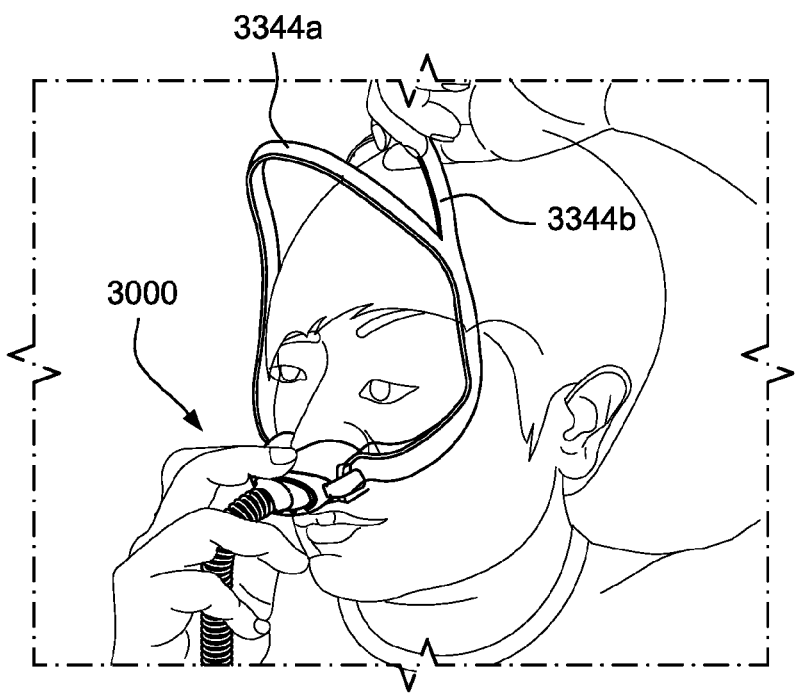

FIG. 85 is a view showing removing of the patient interface according to an example of the present technology.

Figure 86A:
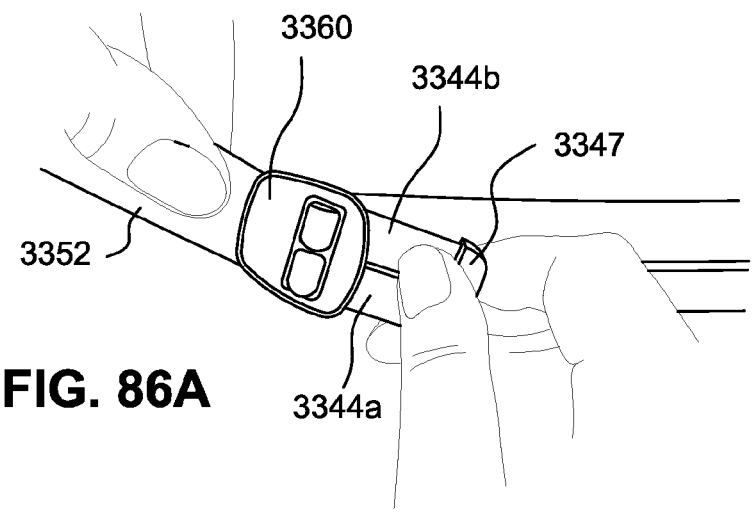
Figure 86B:
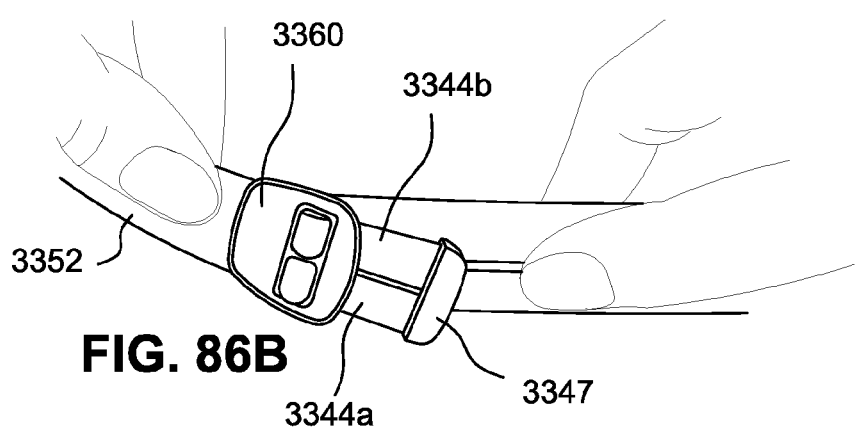

FIGS. 86A and 86B are various views showing adjusting of the buckle of the patient interface according to an example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
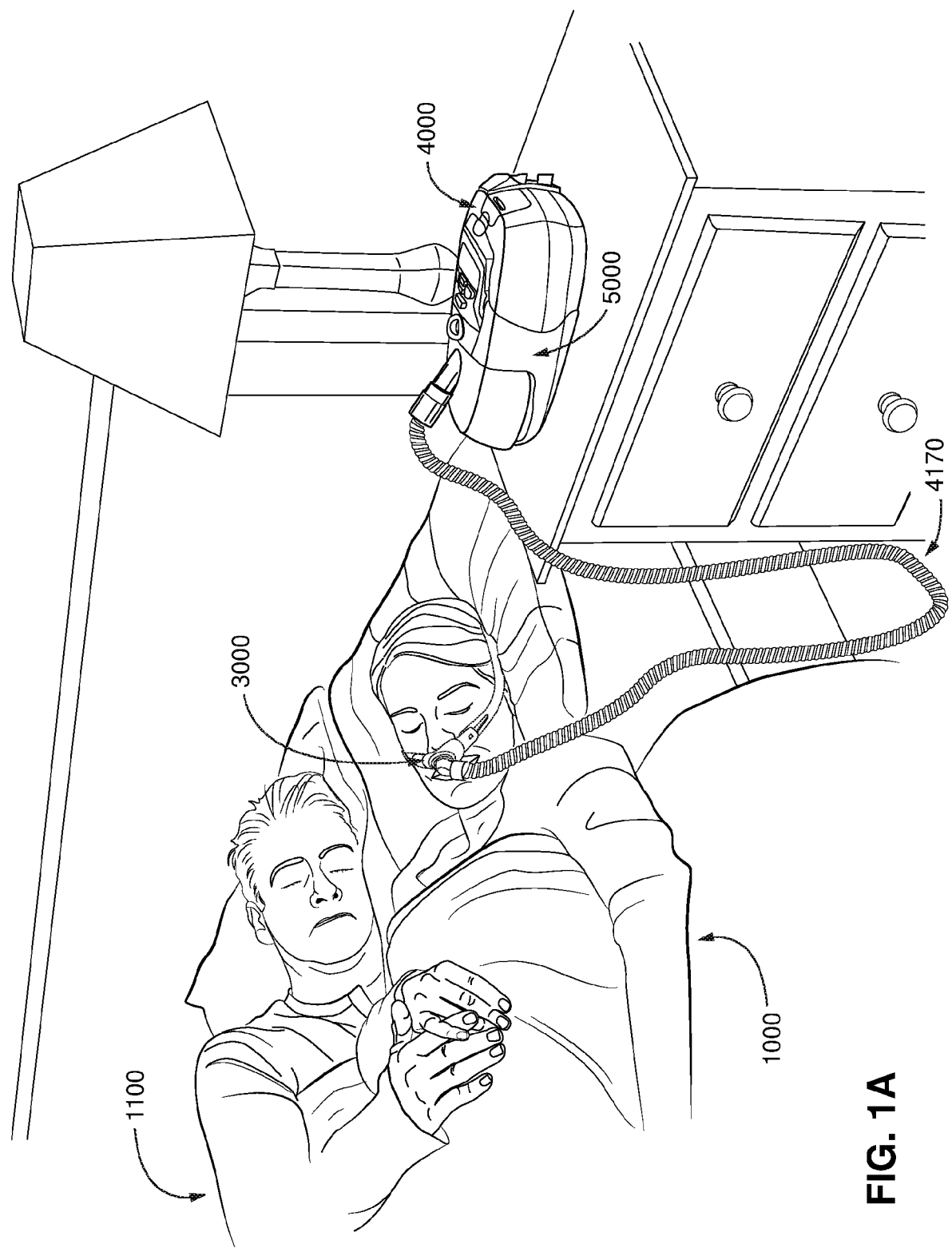
Figure 1B:
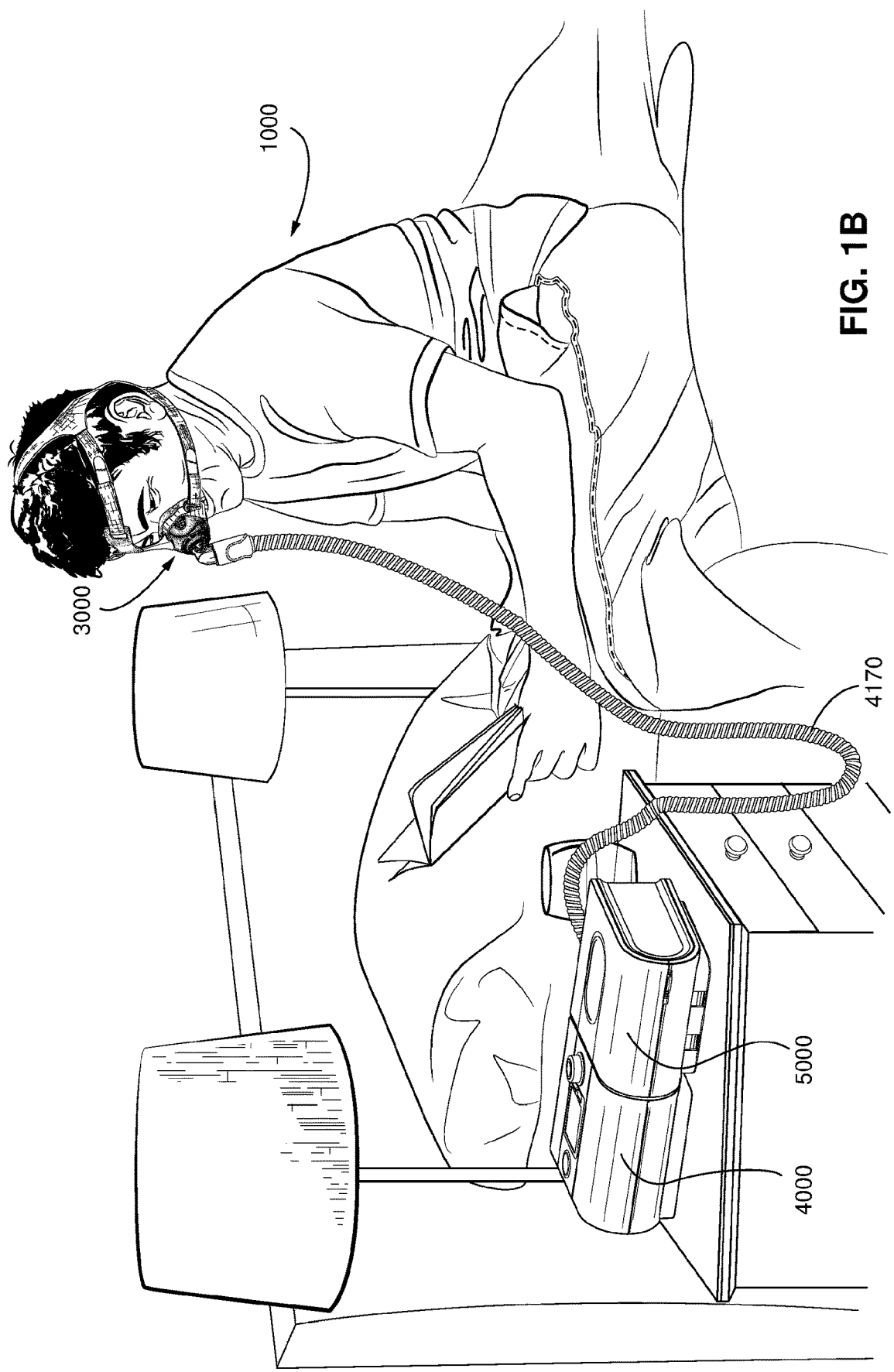
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

Referring to FIGS. 4 to 18, a non-invasive patient interface 3000 in accordance with one aspect of the present technology comprises a frame assembly 3500, a cushion assembly 3075 including a seal-forming structure 3100 and a frame connection structure 3150, and a positioning and stabilizing structure 3300. In some forms, a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

In the illustrated example, the frame assembly 3500 includes a vent 3400 and a connection port 3600 for connection to a short tube 4180 of the air circuit 4170. The frame assembly 3500 also functions as a central hub to which the cushion assembly 3075, the positioning and stabilizing structure 3300, and the short tube 4180 are connected, e.g., either in a removable fashion or a more permanent fashion. The frame assembly 3500 is structured to allow sealing forces to be transferred to the cushion assembly 3075 from the positioning and stabilizing structure 3300.

In one form of the present technology, the frame assembly 3500 and the cushion assembly 3075 are repeatedly and removably engageable with one another, e.g., to allow cleaning and/or replacement of the cushion assembly 3075. The frame assembly 3500 and the cushion assembly 3075 form a plenum chamber 3200 when the frame assembly 3500 and the cushion assembly 3075 are engaged. The plenum chamber 3200 may receive a flow of pressurised gas from the short tube 4180 of the air circuit 4170, which may pass through the seal-forming structure 3100 and into the patient's airways for inhalation.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Nasal Cradle

FIGS. 25 to 37 show the seal-forming structure 3100 of the according to an example of the present technology. In the illustrated example, the seal-forming structure 3100 may be considered a nasal cradle cushion and intended to provide a flow of pressurised gas to the patient's nares by sealing against at least the underside of the patient's nose, e.g., see FIGS. 4, 55, and 56. The exemplary seal-forming structures 3100 will engage the patient's face below the bridge of the nose and some examples, depending on the size and shape of the patient's nose, may engage the patient's nose below the pronasale. The exemplary seal-forming structures 3100 will also engage the patient's face at least above the upper vermillion Thus, the exemplary seal-forming structures 3100 may seal against the patient's lip superior in use. Furthermore, the patient's mouth may remain uncovered by the seal-forming structure 3100 of the depicted examples such that the patient may breathe freely, i.e., directly to atmosphere, without interference from the seal-forming structure 3100.

The exemplary nasal cradle cushion may include a superior saddle or concave region that has positive curvature across the cushion. Also, the nasal cradle cushion may be understood to have a single target seal forming region or surface, in contrast to a pillows cushion may have two target seal forming regions (one for each naris). Cradle cushions may also have a posterior wall that contacts the patient's lip superior and an upper, central, surface contacts the underside of the patient's nose. These two surfaces on the patient's face may form a nasolabial angle between them (see FIG. 2E). A cradle cushion may be shaped to have a nasolabial angle within the range of 90 degrees to 120 degrees.

Furthermore, the exemplary seal-forming structure 3100 may also be shaped and dimensioned such that no portion of the seal-forming structure 3100 enters into the patient's nares during use.

As best shown in FIGS. 33 to 37, the exemplary seal-forming structure 3100 may include at least two regions of different thickness: lateral support regions 3108 and a medial region 3114. In further examples, there may also be a third region (in addition to the lateral support regions 3108 and the medial region 3114) of another different thickness, a mid-lateral region 3110. In still further examples, there may one or more additional regions (in addition to the lateral support regions 3108, the mid-lateral regions 3110, and the medial region 3114) of different thicknesses. As can be seen in the depicted example, the differing thicknesses may be produced by extending regions of different thickness different distances into the interior of the seal-forming structure 3100 such that the exterior surface of the seal-forming structure 3100 remains smooth. The exterior surface may not be uneven at transitional areas between the regions of different thickness. Thus, the exterior of the exemplary seal-forming structures 3100 is continuous and smooth.

In the depicted example, naris openings 3102 may be formed through the medial region 3114. The naris openings 3102 are positioned to generally align with patient's corresponding naris to provide the flow of pressurised gas to the patient's nares for inhalation and for exhaled gas to be passed back into the seal-forming structure 3100 for discharge to atmosphere via the vent 3400. Within the medial region 3114, there may also be a bridge portion 3104 positioned between the naris openings 3102.

In an example, the seal-forming structure 3100 in different examples may be sized and shaped differently and, accordingly, each variation may provide an optimal fit for patients having noses and faces shaped and sized differently.

In an example, the seal-forming structure 3100 may include two or more different sizes/shapes. For example, FIGS. 38-39 show an exemplary small size seal-forming structure 3100, FIGS. 40-41 show an exemplary small-wide size seal-forming structure 3100, and FIGS. 42-43 show an exemplary medium size seal-forming structure 3100. As illustrated, size dimensions and/or contours of the seal-forming structure may be varied to provide alternative seal forming surfaces for different patients.

In an example, one or more thickened portions (e.g., thickened portion of silicone) may be provided to one or more regions of the seal-forming structure 3100 to add support and stability to the one or more regions, e.g., to ensure cushion stability and seal performance. In an example, the one or more thickened portions may be produced by increasing the thickness of the seal-forming structure 3100 in one or more regions into the interior of the seal-forming structure 3100 such that the exterior surface of the seal-forming structure 3100 remains continuous and smooth. The one or more thickened portions may include similar or different thicknesses relative to one another. In an example, the thickness of thickened portion(s) and/or the specific positioning of the thickened portion(s) along the seal-forming structure 3100 may be at least partially dependent on the size of the seal-forming structure 3100.

For example, FIGS. 62 to 67 show an exemplary small-wide size seal-forming structure 3100 including a thickened portion 3120 along a top side of the seal-forming structure 3100 (closer to the nose bridge) and a thickened portion 3121 along a bottom side of the seal-forming structure 3100 (closer to the upper lip), e.g., thickened portions 3120, 3121 provided along lower sides of the seal-forming structure 3100 close to the frame connection structure 3150 in a medial region 3114 of the seal-forming structure 3100.

In contrast, FIGS. 68 to 71 show an exemplary medium size seal-forming structure 3100 including thickened portions 3122 along a bottom side of the seal-forming structure 3100 (closer to the upper lip), e.g., thickened portions 3122 provided along lower sides of the seal-forming structure 3100 close to the frame connection structure 3150 in respective lateral support regions 3108 of the seal-forming structure 3100. In this example, no additional thickened portions are provided to the medium size seal-forming structure 3100 along a top side of the seal-forming structure 3100 (closer to the nose bridge).

However, it should be appreciated that other examples, e.g., thickness and/or positioning, of thickened portions in one or more regions of the seal-forming structure 3100 are possible.

5.3.2 Frame Connection Structure

As shown in FIGS. 25 to 30, the frame connection structure 3150 is structured and arranged to removably and repeatedly connect the cushion assembly 3075 to the frame assembly 3500, e.g., to facilitate cleaning, replacement, and/or to change for a different cushion assembly 3075 having a differently sized seal-forming structure 3100 as described above in relation to FIGS. 38-43.

The frame connection structure 3150 includes a seal connecting portion 3160 adapted to connect to the seal-forming structure 3100 and a frame connecting portion 3170 adapted to connect to the frame assembly 3500.

The frame connection structure 3150 may be permanently (e.g., overmolded) or removably (e.g., interference fit assembly) connected to the seal-forming structure 3100.

Overmolded Construction

In the illustrated example, the frame connection structure 3150 and the seal-forming structure 3100 comprise an overmolded construction to form a one-piece, integrated component.

For example, the frame connection structure 3150 comprises a first part or base mold and the seal-forming structure 3100 comprises a second part or overmold that is provided (e.g., by overmolding) to the first part.

In an example, the frame connection structure 3150 comprises a material that is more rigid than the seal-forming structure 3100. In an example, the frame connection structure 3150 and the seal-forming structure 3100 may comprise a similar material (e.g., thermoplastic elastomer (TPE) or silicone), with the frame connection structure 3150 having a higher durometer (e.g., higher Shore A hardness) than the seal-forming structure 3100, thereby providing a dual-durometer component.

In an example, the cushion assembly 3075 may be formed by a 2-shot sequential overmolding process in which different materials are injected in the same molding machine to form the cushion assembly 3075. For example, in the first step, the molding machine injects a first material into a closed cavity (i.e., first shot) to form the frame connection structure 3150 (i.e., the first part or base mold) into its shape. In the second step, the molding machine injects a second material into the remaining space of the closed cavity (i.e., second shot) to form the seal-forming structure 3100 (i.e., the second part or overmold) into its shape as an overmold onto the frame connection structure 3150. In an example, the frame connection structure 3150 may comprise an insert after the first shot, and the molding machine may move the mold cores and/or the insert (i.e., frame connection structure 3150) to create a second cavity for forming the seal-forming structure 3100 in the second shot.

In an example, the seal-forming structure 3100 may be overmolded to the frame connection structure 3150 from a material that is able to chemically bond or self-adhere to the material of the frame connection structure 3150. For example, as shown in FIG. 30, the seal connecting portion 3160 of the frame connection structure 3150 may provide one or more interfacing surfaces 3615 (e.g., land area) structured to bond with the seal-forming structure 3100. Such bond may be made stronger by increasing the land area. In an example, the seal connecting portion 3160 may provide a chemical bond without a mechanical interlock. As a result, the connection includes no cracks, a gas tight seal, and clean interface.

As a result, the entire cushion assembly 3075 may comprise silicone material with areas of different hardness. In an example, the frame connection structure 3150 (i.e., the first shot or base mold) may comprise a higher durometer silicone material (e.g., Shore A hardness greater than 60 Shore A, e.g., 65 Shore A, 60-70 Shore A, 60-90 shore A, up to 70 Shore A, up to 90 Shore A), and the seal-forming structure 3100 (i.e., the second shot or overmold) may comprise a lower durometer silicone material than the frame connection structure 3150 (e.g., Shore A hardness greater than 30 Shore A, e.g., 40 Shore A, 30-50 Shore A, less than 50 Shore A).

In an example, the frame connection structure 3150 (i.e., the first shot or base mold) may comprise a higher durometer LSR material, and the seal-forming structure 3100 (i.e., the second shot or overmold) may comprise a lower durometer LSR material. However, it should be appreciated that other suitable materials may be used.

The higher durometer, frame connection structure 3150 comprises a more rigid material adapted for connection to the frame assembly 3500. As illustrated, the frame connecting portion 3170 of the frame connection structure 3150 forms a barbed end or undercut 3175 that acts as an interface or catch adapted to connect to the frame assembly 3500. The use of silicone material and the overmolding process for forming the frame connection structure 3150 allows for demolding of the barbed end or undercut, which allows the cushion assembly to comprise a smaller size and profile (e.g., smaller and easier to fabricate than overmolding seal onto a hard plastic clip). The use of higher durometer, silicone material for the frame connection structure 3150 also has the advantages of being more robust against physical damage by external forces (e.g., crush-resistant unlike a hard plastic clip) and having less expensive manufacturing costs.

In the illustrated example, the frame connection structure 3150 is arranged along an interior surface or interior periphery of the seal-forming structure 3100 such that the frame connection structure 3150 is arranged or oriented towards the interior of the cushion assembly, i.e., the frame connection structure 3150 projects inwardly from the interior surface or interior periphery of the seal-forming structure 3100 towards the cavity of the seal-forming structure 3100, which forms at least a portion of the plenum chamber 3200. This arrangement allows the frame connection structure 3150 and undercut 3175 thereof to be stretched over and onto the frame assembly 3500 for attachment.

In an example, the frame connection structure 3150 and undercut 3175 thereof extends around the entire perimeter or the entire interior periphery of the seal-forming structure 3100. In an alternative example, the frame connection structure 3150 and undercut 3175 thereof may extend along one or more selected portions of the perimeter of the seal-forming structure 3100, e.g., along a partial interior periphery of the seal-forming structure 3100.

In an example, the frame connection structure 3150 may provide a profile that forms a smooth and continuous curve along the periphery of the cavity of the seal-forming structure 3100, e.g., frame connection structure 3150 flush with the seal-forming structure 3100. In an example, the length of the frame connection structure 3150 protruding into the cavity may be the same along the entire perimeter of the seal-forming structure 3100. It should be appreciated that, in alternative examples, the profile of the frame connection structure 3150 may vary along one or more portions of the periphery the seal-forming structure 3100. For example, the length of the frame connection structure 3150 may vary along one or more portions of the perimeter of the seal-forming structure 3100.

The lower durometer, seal-forming structure 3100 comprises a softer, more comfortable material adapted for sealing with a patient's face. In addition, a sealing lip 3850 is formed along with the seal-forming structure 3100 of the lower durometer material. As described below, the sealing lip 3850 is arranged along an interior surface or interior periphery of the seal-forming structure 3100 and adapted to form a seal with the frame assembly 3500 (e.g., when pressure is increased within the plenum chamber 3200), e.g., to prevent leaks for more effective treatment and patient satisfaction.

In the illustrated example, the frame connection structure 3150 is provided along the edge of the cavity of the seal-forming structure 3100, and the sealing lip 3850 is arranged inward of the frame connection structure 3150 within the cavity. The frame connection structure 3150 and the sealing lip 3850 form a space therebetween to receive a portion of the frame assembly 3500 for attachment of the cushion assembly 3075 to the frame assembly 3500 as described below.

In an example, the frame connection structure 3150 (i.e., the first shot or base mold) may comprise a similar color or a different color than the seal-forming structure 3100 (i.e., the second shot or overmold), e.g., both the frame connection structure 3150 and the seal-forming structure 3100 comprise a clear or generally transparent color.

In an example, the frame connection structure 3150 (i.e., the first shot or base mold) may comprise a similar surface finish or a different surface finish than the seal-forming structure 3100 (i.e., the second shot or overmold), e.g., the frame connection structure 3150 comprises a highly polished surface finish and the seal-forming structure 3100 comprises a textured surface finish.

FIGS. 31 and 32 are alternative views of the cushion assembly 3075 showing a contrast between the frame connection structure 3150 and the seal-forming structure 3100 according to an example of the present technology.

5.3.3 Frame Assembly

As best shown in FIGS. 15 to 24, the frame assembly 3500 comprises a main body 3510 and a cover 3580 provided to an anterior side of the main body 3510.

In an example, the main body 3510 and the cover 3580 may be constructed (e.g., molded) of a relative rigid material, e.g., polypropylene, polycarbonate.

The main body 3510 includes a body portion 3520, a cushion connecting portion 3530, and a cover connecting portion 3540. Also, as described in more detail below, the main body 3510 and the cover 3580 cooperate to form the vent 3400 and cooperate to maintain diffusing members 3450, e.g., filter materials, of the vent 3400 within the frame assembly 3500.

In the illustrated example, each of a pair of rigidizer arms 3302 of the positioning and stabilising structure 3300 are connected to respective sides of the main body 3510 by a respective one of a pair of flexible joints 3305. In an example, the flexible joints 3305 may be permanently connected to the main body 3510 and may be permanently connected to respective rigidizer arms 3302, e.g., via overmold, interference fit assembly. However, the rigidizer arms 3302 may be connected to the main body 3510 in other suitable manners.

The cover 3580 includes an anterior wall 3585 and a tube portion 3590. The tube portion 3590 comprises the connection port 3600 for connection to a short tube 4180 of the air circuit 4170. In an example, the cover 3580 may also be referred to as a tube connector.

In the illustrated example, the short tube 4180 may be directly connected or otherwise provided to the connection port 3600 without the use of an elbow or swivel elbow. For example, the short tube 4180 may be directly connected to an anterior side of the tube portion 3590 of the cover 3580. The short tube 4180 may be permanently or removably connected to the connection port 3600. Permanent connection may be by way of overmolding or interference fit assembly. In an alternative example, the short tube 4180 may be connected to the connection port 3600 via an elbow or swivel elbow. In yet another example, the air circuit 4170 may be connected (e.g., directly or via an elbow) to the connection port 3600 without the use of a short tube 4180.

In the illustrated example, the anterior side of the anterior wall 3585 includes contoured surfaces that blend into the anterior side of the tube portion 3590, e.g., for aesthetics as the anterior wall and anterior side of the tube portion 3590 provides a front side of the patient interface 3000.

In the illustrated example, the posterior side of the tube portion 3590 protrudes from a posterior side of the anterior wall 3585. The cover connecting portion 3540 of the main body 3510 is in the form of a tube adapted to receive the posterior side of the tube portion 3590, e.g., in telescoping manner, to align and connect the cover 3580 to the main body 3510. As illustrated, the tube portion 3590 and the cover connecting portion 3540 includes a snap or interference fit assembly, e.g., posterior side of the tube portion 3590 includes a peripheral groove 3595 adapted to engage a peripheral bead 3545 along the interior of the cover connecting portion 3540 (e.g., see FIG. 13). However, it should be appreciated that the cover 3580 may be connected to the main body 3510 in other suitable manners, e.g., either in a removable fashion or a more permanent fashion.

In the illustrated example, the posterior side of the anterior wall 3585 provides a stop to prevent over-insertion of the tube portion 3590 into the cover connecting portion 3540 of the main body 3510. Also, in an example, the recessed region 3550 in the anterior side of the main body 3510 includes a plurality of ribs 3560 along its perimeter that form a portion of the vent 3400, and such ribs 3560 may provide a step 3562 structured and arranged to provide a stop for the outer edge of the anterior wall 3585. Such stops maintain spacing between the anterior wall 3585 and the sides and bottom of the recessed region 3550, which forms a diffusion section for the vent 3400 including diffusing members 3450, as discussed in more detail below.

In an example, the cover 3580 and the main body 3510 may each include an alignment feature to ensure that the cover 3580 and the main body 3510 are correctly aligned or oriented for assembly. For example, as best shown in FIGS. 57 and 58, the cover 3580 may include a protrusion 3581 (e.g., male alignment feature) adapted to receive a corresponding recess 3511 (e.g., female alignment feature) in the main body 3510. However, other suitable alignment features are possible.

In an example, the frame assembly 3500 (e.g., see main body 3510 and anterior wall of the cover 3580) includes a curvature (e.g. when viewed from the top as shown in FIGS. 20 and 24) intended to follow the natural curvature of patient's upper lip and may avoid concentration of contact pressure on any specific point of the patient's upper lip such that contact pressure from headgear tension is evenly spread over the patient's upper lip, e.g., to minimise or eliminate skin breakdown caused by prolonged concentrated contact pressure. Another advantage for the curvature is that less material may be required, which leads to an overall weight reduction for the patient interface 3000. The curvature also minimizes any protrusion of the patient interface 3000 in the anterior direction from the patient's face which improves the unobtrusiveness of the patient interface 3000.

In an example, the frame assembly 3500 may be made in one size but the cushion assembly 3075 may be made in multiple sizes that are attachable to the single frame assembly 3500 by commonly sized connections features, e.g., cushion sizes include different sized seal-forming structures with common sized frame connection structures for attachment to the common frame assembly 3500.

5.3.4 Connection Between Cushion Assembly and Frame Assembly

In the illustrated example, the frame connecting portion 3170 of the cushion assembly 3075 and the cushion connecting portion 3530 of the frame assembly 3500 includes an interference fit assembly.

For example, the frame connecting portion 3170 of the cushion assembly 3075 forms the barbed end or undercut 3175, and the cushion connecting portion 3530 of the frame assembly 3500 includes a channel with an undercut 3535 along a posterior wall of the channel. As shown in FIG. 13, the barbed end or undercut 3175 of the frame connecting portion 3170 is structured and arranged to engage over and behind the undercut 3535 of the cushion connecting portion 3530 to releasably connect the cushion assembly 3075 to the frame assembly 3500. In an example, the barbed end of the frame connecting portion 3170 and the channel of the frame assembly 3500 forms a tongue and groove arrangement to removably and repeatedly connect the cushion assembly 3075 to the frame assembly 3500.

In an example, the relatively flexible material of the cushion assembly 3075 allows the frame connection structure 3150 and the frame connecting portion 3170 thereof to be stretched over the cushion connecting portion 3530 until the barbed end or undercut 3175 of the frame connecting portion 3170 can catch or interface with the undercut 3535 of the cushion connecting portion 3530, e.g., frame connection structure 3150 forms a relatively flexible ring that can be stretched over the relatively harder frame assembly 3500 for attachment.

As shown in FIG. 30, the frame connecting portion 3170 of the frame connection structure 3150 may include a tapered or angled leading surface 3171 to guide and facilitate outward deflection of the frame connecting portion 3170 over and behind the cushion connecting portion 3530 of the frame assembly 3500, e.g., tapered or angled leading surface 3171 adapted to engage a tapered or angled leading surface on cushion connecting portion 3530 of the frame assembly 3500 to facilitate assembly.

In an example, the higher durometer, frame connection structure 3150 may be or act as a "cushion clip" structured and arranged to removably and repeatedly clip the cushion assembly 3075 to the frame assembly 3500. For example, the increased hardness provided by the higher durometer material of the frame connection structure 3150 may act as clip structure structured to reduce deformation of the frame connection structure 3150, thereby allowing the frame connection structure 3150 to maintain engagement between the cushion assembly 3075 and the frame assembly 3500 and resist removal of the cushion assembly 3075 from the frame assembly 3500.

The cushion assembly 3075 and the frame assembly 3500 may be disconnected by applying enough force for the frame connection structure 3150 of the cushion assembly 3075 to be stretched out of the channel to escape or clear the undercut 3535 of the cushion connecting portion 3530 of the frame assembly 3500.

Sealing Lip

As noted above, a sealing lip 3850 is formed along with the seal-forming structure 3100 of the lower durometer material. As best shown in FIGS. 29-30, the sealing lip 3850 is in the form of a flexible flap arranged along an interior surface or interior periphery of the seal-forming structure 3100. The sealing lip 3850 protrudes into a cavity of the seal-forming structure 3100, which forms at least a portion of the plenum chamber 3200.

In an example, as shown in FIG. 13, the sealing lip 3850 is structured and arranged to engage the frame assembly 3500 to form a pneumatic seal with the cushion connecting portion 3530 of the frame assembly 3500 (e.g., posterior wall of the channel). In an example, the sealing lip 3850 may be structured and arranged to engage the frame assembly 3500 when the cushion assembly 3075 is initially connected to the frame assembly 3500, e.g., sealing lip 3850 arranged to deflect against the cushion connecting portion 3530 of the frame assembly 3500 by interference. When pressure within the plenum chamber 3200 is increased above atmospheric pressure for treating breathing disorders, the pneumatic seal is strengthened and increases the sealing force as the sealing lip 3850 is urged with greater force against the frame assembly 3500.

In an alternative example, the sealing lip 3850 may be spaced from or adjacent to the frame assembly 3500 when the cushion assembly 3075 is initially connected to the frame assembly 3500, and the sealing lip 3850 forms the seal with the frame assembly 3500 when pressure is increased within the plenum chamber 3200.

The sealing lip 3850 is sufficiently long so that the sealing lip 3850 does not get caught or trapped in the frame assembly 3500 when the frame connection structure 3150 of the cushion assembly 3075 is stretched over the cushion connecting portion 3530 of the frame assembly 3500 during assembly.

In an example, the length of the sealing lip 3850 may be the same along the entire perimeter of the seal-forming structure 3100. In alternative examples, the length of the sealing lip 3850 may vary along one or more portions of the perimeter of the seal-forming structure 3100.

For example, as shown in the example of FIGS. 72 and 73, the sealing lip 3850 may be longer at the two lateral ends or sides of the seal-forming structure 3100 to prevent the sealing lip 3850 from being caught or trapped when the cushion assembly 3075 is stretched and released laterally during its assembly onto the frame assembly 3500. This configuration is best shown in FIG. 73 which shows the portions of the sealing lip 3850 at the two lateral ends or sides of the seal-forming structure 3100 being longer (i.e., protruding further into the cavity of the seal-forming structure 3100) than the portions of the sealing lip 3850 at the top (superior) and bottom (inferior) sides of the seal-forming structure 3100.

Further, the curvature of the sealing lip 3850 may vary along one or more portions of the perimeter of the seal-forming structure 3100. For example, as best shown in FIG. 72, the longer, sealing lip 3850 at the two lateral ends or sides of the seal-forming structure 3100 may also include a curvature so that the sealing lip 3850 at the two lateral ends or sides of the seal-forming structure 3100 protrudes or curves further away from the frame connection structure 3150 than the portions of the sealing lip 3850 at the top (superior) and bottom (inferior) sides of the seal-forming structure 3100. Such arrangement may also facilitate assembly of the cushion assembly 3075 onto the lateral ends of the frame assembly 3500 without the sealing lip 3850 being caught or trapped, e.g., sufficient space provided between the frame connection structure 3150 and the sealing lip 3850 to allow connection of the frame connection structure 3150 without the sealing lip 3850 getting trapped in the frame assembly 3500 during assembly.

Alignment Features

In an example, the patient interface 3000 may include visual indicators and/or tactile indicators to prevent or minimise misorientation and improper assembly/disassembly. This may ensure proper assembly/disassembly, avoid inadvertent damage to the patient interface 3000, and also ease any user frustration associated with assembly/disassembly.

In an example, the cushion assembly 3075 and the frame assembly 3500 may each include an alignment feature to ensure that the cushion assembly 3075 and the frame assembly 3500 are correctly aligned or oriented for assembly.

For example, as best shown in FIGS. 16 to 18, the cushion connecting portion 3530 of the frame assembly 3500 may include one or more protrusions 3537 (e.g., male alignment feature) within the channel adapted to receive a corresponding one of one or more recesses 3177 (e.g., female alignment feature) along the frame connecting portion 3170 of the cushion assembly 3075. As illustrated, the protrusions 3537/recesses 3177 are only provided on one side of the frame assembly 3500/cushion assembly 3500 (e.g., superior side) to ensure proper orientation of the cushion assembly 3075 when connected to the frame assembly 3500.

In an alternative example, as shown in FIGS. 59-61, the cushion connecting portion 3530 of the frame assembly 3500 may include a single protrusion 3537 on a lateral side of the frame assembly 3500 that is adapted to receive a corresponding recess 3177 along a lateral side of the frame connecting portion 3170 of the cushion assembly 3075.

In another example, as shown in FIGS. 72-75, the cushion connecting portion 3530 of the frame assembly 3500 may include a single protrusion 3577 on a central, superior side of the frame assembly 3500 that is adapted to receive a corresponding cut-out 3179 along a central, superior side of the cushion assembly 3075.

In the example of FIGS. 16-18 and 59-61, the recess(s) 3177 are provided on the inner side of the periphery of the frame connection structure 3150. In the example of FIGS. 72-75, the cut-out 3179 comprises a complete cut-through on the periphery of the frame connection structure 3150 so that a distinct recess is provided on the edge of the cushion assembly 3075. In contrast to the example of FIGS. 16-18 and 59-61, the cut-out configuration of FIGS. 72-75 and its location on a central, superior side of the cushion assembly 3075 may provide a clearer, visual indication to the patient to allow them to more easily assemble the cushion assembly 3075 to the frame assembly 3500 in the correct orientation.

In should be appreciated that the alignment feature may include alternative shapes and locations. For example, the alignment feature may be provided along any portion or portions along the periphery of the cushion assembly and frame assembly, and the alignment feature may include any suitable shape, e.g., cut-out or recess on inner or outer side of the frame connection structure 3150. Further, it should be appreciated that any suitable number of alignment features may be provided (e.g., any suitable number of cut-outs and/or recesses), and alignment feature alternatives may be combinable with one another, e.g., see FIG. 75 including frame assembly 3500 with both protrusion 3577 and protrusions 3537 adapted to receive a cut-out 3179 and recesses 3177 (not shown) on the inner side of the frame connection structure 3150. In each example, the alignment feature is arranged such that misalignment and incorrect assembly of the cushion assembly 3075 to the frame assembly 3500 may be reduced. In an example, the alignment feature may prevent assembly unless the alignment feature of the cushion assembly 3075 and the frame assembly 3500 are aligned with one another.

5.3.5 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.6 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face. In an example the strap may be configured as a tie.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

Referring to FIGS. 4-7 and 44-56, a positioning and stabilising structure 3300 is shown according to an example of the present technology. In the illustrated example, the positioning and stabilising structure 3300 comprises a pair of rigidizer arms 3302 and a headgear strap assembly 3330 provided to the pair of rigidizer arms 3302. The rigidizer arms 3302 and the headgear strap assembly 3330 cooperate to hold the patient interface 3000 of the present technology in sealing position in use, e.g., rigidizer arms 3302 direct tension vectors generated by the headgear strap assembly 3330 so that the seal-forming structure 3100 seals against the base of the patient's nose.

As noted above, each of a pair of rigidizer arms 3302 is connected to respective sides of the main body 3510 of the frame assembly 3500 by a respective one of a pair of flexible joints 3305. However, the rigidizer arms 3302 may be connected to the main body 3510 in other suitable manners.

In the illustrated example, the headgear strap assembly 3330 includes a pair of straps 3340, 3350 (e.g., each constructed of an elastic textile) which are connected to one another by an adjustment mechanism, e.g., a buckle 3360, which permits length adjustment, e.g., in addition to the length adjustment provided by the elasticity of the straps 3340, 3350 as described below.

As illustrated, the pair of straps comprises a first, longer strap 3340 and a second, shorter strap 3350, the first strap 3340 being longer than the second strap 3350 in its original length in a neutral, non-stretched state.

Each strap 3340, 3350 may be made of an elastic material and may have elastic properties. In other words, each strap may be elastically stretched to increase the length of the strap, e.g., by a stretching force applied by the patient, and upon release of the stretching force, returns or contracts to its original length in a neutral state. Each strap may be made of or comprise any elastomeric material such as elastane, TPE, silicone etc. The material of each strap may also represent a combination of any of the above materials with other materials. Each strap may be a single layer or multi-layer strap. Each strap may be woven, knitted, braided, molded, extruded or otherwise formed. Each strap may comprise or may be made of a textile material such as a woven material. Such material may comprise artificial or natural fibers for, on the one hand, providing desired and beneficial surface properties such as tactile properties and skin comfort. On the other hand, the material of each strap may include elastomeric material for providing the desired elastomeric properties. In the illustrated example, each strap is stretchable. This enables the entire length of each strap to be stretched which leads to a comfortable force displacement profile.

The first strap 3340 includes a side strap portion 3342 and a back strap portion 3344. As illustrated, the back strap portion 3344 includes a split region that splits the back strap portion 3344 into two back strap portions 3344a, 3344b, i.e., the side strap portion 3342 bifurcates into two back strap portions 3344a, 3344b. The second strap 3350 includes a side strap portion 3352.

In the illustrated example, one end of the side strap portion 3352 is non-adjustably connected to the buckle 3360, and the two back strap portions 3344a, 3344b of back strap portion 3344 are wound or threaded through the buckle 3360 to permit adjustment relative to the buckle 3360.

The headgear strap assembly 3330 is rigidised at a certain section, for example, from the frame assembly 3500 up to a position proximal to the patient's cheekbone by the inserted rigidiser arms 3302. Each strap 3340, 3350 of the headgear strap assembly 3330 may take the form of a hollow ribbon structured to receive a respective one of the rigidiser arms 3302 therein. Each strap may be considered to be threaded over a respective one of the rigidiser arms 3302 when it is slipped onto the respective rigidiser arm 3302 and secured at one end of the respective rigidiser arm 3302 proximal to the frame assembly 3500.

In the illustrated example, each strap 3340, 3350 has a tube-like configuration as can be taken from the schematic view in FIG. 44A indicating an oval or circular shape, as well as by the exemplary cross-sectional view according to FIG. 44B. However, it will be appreciated that the positioning and stabilising structure 3300 may take any other shape such as flat or sheet-like shape, single, multi-layer or laminate construction.

The side strap portions 3342, 3352 of respective straps 3340, 3350 each include a button-hole 3343, 3353, e.g., slit-like configuration. The button-holes 3343, 3353 may be located at the outer surface of respective straps 3340, 3350, i.e., the surface facing away from the patient when being worn, and are adapted to receive a respective rigidiser arm 3302 in order to insert the rigidiser arm 3302 into the interior of the tube- or sleeve-like strap 3340, 3350 or to remove it therefrom. Alternatively, the button-holes 3343, 3353 may be located at the inner surface of respective straps 3340, 3350. In an example, each side strap portion 3342, 3352 may include a pocketed end adapted to receive an end of the respective rigidiser arm 3302 proximal to the frame assembly 3500.

In the illustrated, each end of the first strap 3340 includes a reinforcement portion or finger tab 3345, 3347, and the end of the second strap 3350 opposite to the buckle 3360 includes a reinforcement portion or finger tab 3355. In an example, each reinforcement portion or finger tab 3345, 3347, 3355 comprises a different material than the straps 3340, 3350, e.g., TPE material. In an example, each reinforcement portion or finger tab 3345, 3347, 3355 may be overmolded to respective ends of the straps 3340, 3350, however each reinforcement portion or finger tab 3345, 3347, 3355 may be connected to the straps in other suitable manners.

Each reinforcement portion or finger tab 3345, 3347, 3355 provides reinforcement to respective ends of the straps 3340, 3350, e.g. to avoid or mitigate the likelihood of a patient tearing or ripping the straps 3340, 3350. Further, the reinforcement portion or finger tabs 3345, 3355 helps provide a visual and tactile indication to the patient on how to slip on or remove the straps 3340, 3350 from respective rigidiser arms 3302 and may assist in identifying the location of the button-holes 3343, 3353. Also, the reinforcement portion or finger tab 3347 is provided (e.g., overmolded) to the end of the two back strap portions 3344a, 3344b after the two back strap portions 3344a, 3344b are wound or threaded through the buckle 3360 in order to prevent removal of the strap 3340 from the buckle 3360. Further, the reinforcement portion or finger tab 3347 provides a visual and tactile indication for adjustment of the back strap portion 3344 relative to the buckle 3360.

As shown in FIGS. 4, 55, and 56, the side strap portions 3342, 3352 of respective straps 3340, 3350 are adapted to extend along the sides of a patient's head when being worn while back strap portion 3344 of strap 3340 is adapted to extend along the back of a patient's head.

In order for the headgear strap assembly 3330 to be stretched in use, the length of the headgear strap assembly 3330 may be less than the average small head circumference of patients. For example, the length of the headgear strap assembly 3330 (e.g., the length of the headgear assembly with the back strap portion 3340 fully retracted with respect to the buckle 3360 as shown in FIG. 45) may be less than 600 mm in one example and less than 500 mm in another example. However, headgear strap assembly 3330 of different lengths may be provided to patients depending on their head circumference which may be gender specific.

In the illustrated example, the straps 3340, 3350 are joined by the buckle 3360 which permits length adjustment in addition to the length adjustment provided by the elasticity of the straps 3340, 3350. As illustrated, the buckle 3360 includes a main body 3362 with a first end portion 3364 and a second end portion 3366. In the illustrated example, the first end portion 3364 is curved or angled upwardly relative to the second end portion 3366. The second end portion 3366 is connected to an end of the strap 3350, e.g., via overmolding. The main body 3362 includes openings for receiving back strap portions 3344a, 3344b, i.e., a first opening 3370 configured to receive both back strap portions 3344a, 3344b and a pair of second openings 3372a, 3372b configured to respective ones of the back strap portions 3344a, 3344b. A cross-bar 3380 delineates the first opening 3370 from the second openings 3372a, 3372b, and cross-bar 3382 delineates opening 3372a from opening 3372b.

As illustrated, the back strap portions 3344a, 3344b are threaded up through the first opening 3370, around the cross-bar 3380, and down through respective ones of the second openings 3372a, 3372b. Each of the second openings 3372a, 3372b includes an angled edge or surface 3375 arranged to resist adjustment in use.

In an example, the buckle 3360 comprises a relatively rigid material, e.g., polypropylene, polyethylene, and may include an overmold, e.g., comprising TPE material. For example, in the exemplary cross-section of the buckle 3360 in FIGS. 51 and 52, the buckle 3360 includes a relatively rigid base 3390, e.g., polypropylene, polyethylene, with a softer overmold 3391, e.g., TPE. In the illustrated example, the overmold 3391 is not provided along the openings 3370, 3372a, 3372b. In an example, one or portions may be polished, e.g., regions surrounding the openings 3370, 3372a, 3372b as shown by the hatched areas in FIG. 50, e.g., to reduce friction and facilitate gliding or sliding adjustment of the back strap portions 3344a, 3344b relative to the buckle 3360. However, other suitable material are possible.

FIGS. 53-56 are exemplary views showing strap adjustment of the headgear strap assembly 3330 according to an example of the present technology. The headgear strap assembly 3330 allows for precise adjustment of the tensioning and therefore ensuring better sealing of the cushion assembly 3075, especially after repeated use and/or washing of the headgear strap assembly 3330 which may lead to a loss of the strap elasticity. Adequate tensioning by the headgear strap assembly 3330 may be especially important for the nasal cradle type seal-forming structure 3100 of the present technology, e.g., compared to a pillows type seal-forming structure where less tension is required for sealing.

The adjustment mechanism (e.g., a buckle 3360) is operable to allow the (effective) length of the elastic straps 3340, 3350 to be adjusted by the patient to maintain the required stretch force and fit over time. For example, the elastic straps 3340, 3350 may be joined by the buckle 3360 in a first adjusted position (e.g., with the back strap portion 3340 substantially retracted with respect to the buckle 3360 as shown in FIGS. 45 and 55) and one or more second adjusted positions (e.g., with the back strap portion 3340 overlapped to a different extent than the first adjusted positon as shown in FIG. 56). In each adjusted position, the headgear strap assembly 3330 may comprise (1) a neutral or unstretched state in which the headgear strap assembly 3330 comprises a neutral or unstretched length (i.e., no stretching force applied to the elastic straps 3340, 3350 to elastically stretch the straps 3340, 3350), and (2) one or more extended or stretched states in which the headgear strap assembly 3330 comprises one or more extended or stretched lengths (i.e., stretching force applied to the elastic straps 3340, 3350 to elastically stretch and increase the length of the straps 3340, 3350). In each adjusted position, the material of the straps 3340, 3350 limits the extended or stretched length in the extended position to a certain extent, i.e., the maximum or effective length the headgear strap assembly 3330 in each adjusted position. When the elastic strap 3340 is adjusted relative to the buckle 3360 (e.g., from a first adjusted position to a second adjusted position), the neutral or unstretched length of the headgear strap assembly 3330 changes, e.g., the length shortens when adjusted from a first adjusted position to a second adjusted position. Such shortened length in the neutral or unstretched state also shortens the extended or stretched lengths, e.g., the maximum or effective length the headgear strap assembly 3330 in the second adjusted position is shortened. This arrangement allows adjustment of the maximum or effective stretchable length, e.g., to accommodate loss of strap elasticity so as to maintain a comfortable force displacement profile. Thus, the elasticity of the straps 3340, 3350 provides an adjustment mechanism to permit length adjustment in a given adjusted position, and the buckle 3360 provides an additional adjustment mechanism to permit length adjustment in addition to the extent of length adjustment provide by the elasticity of the straps 3340, 3350.

As shown in FIG. 53, the buckle 3360 is in a locked position when the buckle extends generally parallel to the back strap portions 3344a, 3344b to resist unintentional adjustment due to friction between the back strap portions 3344a, 3344b, respective free ends of the back strap portions 3344a, 3344b, and the angled edge or surface 3375 in respective second openings 3372a, 3372b. As shown in FIG. 54, the buckle 3360 can be lifted or pivoted to an unlocked position so that the buckle extends transverse to the back strap portions 3344a, 3344b to allow adjustment due to reduced friction between the back strap portions 3344a, 3344b, respective free ends of the back strap portions 3344a, 3344b, and the angled edge or surface 3375 in respective second openings 3372a, 3372b. That is, the buckle 3360 in the unlocked position may be angled to allow for the back strap portions 3344a, 3344b to glide easily relative to the buckle 3360 for length adjustment. This arrangement is achieved by multiple forward and backwards bends of the back strap portions 3344a, 3344b wrapping around the cross-bar 3380 within the buckle 3360, e.g., Capstan effect working principle.

Such arrangement provides a simple, easy-to-use, buckle adjustment mechanism for the patient, especially when the patient interface is donned by the patient. In an example, such adjustment arrangement may be performed by one hand and may include one-step adjustment, e.g., simply pull the free end of the back strap portions 3344a, 3344b (e.g., via reinforcement portion or finger tab 3347) relative to the buckle 3360 to tighten and simply pivot and pull the buckle 3360 relative to the back strap portions 3344a, 3344b to loosen.

FIG. 55 is a side view of a patient interface shown on a patient's head according to an example of the present technology, the patient interface being shown with the headgear strap assembly in a first adjusted position, e.g., looser position. FIG. 56 is a side view of a patient interface shown on a patient's head according to an example of the present technology, the patient interface being shown with the headgear strap assembly in a second adjusted position, e.g., tighter position.

FIGS. 83A to 86B are various views showing the fitting, adjusting, and removing of the patient interface 3000 according to an example of the present technology.

Figure 83A:
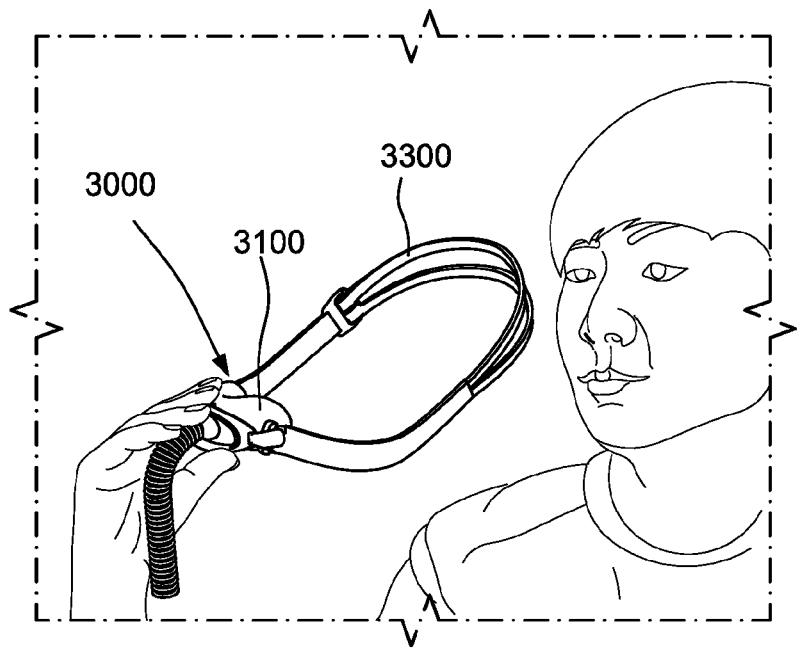

For example, in FIG. 83A, the patient begins fitting the patient interface 3000 by holding the patient interface 3000 away from the patient's nose ensuring that the positioning and stabilising structure 3300 is curving or oriented upwards. This facilitates orientation and engagement of the seal-forming structure 3100 with respect to the patient's nose and facilitates orientation and engagement of the positioning and stabilising structure 3300 over the top of the patient's head.

Figure 83B:
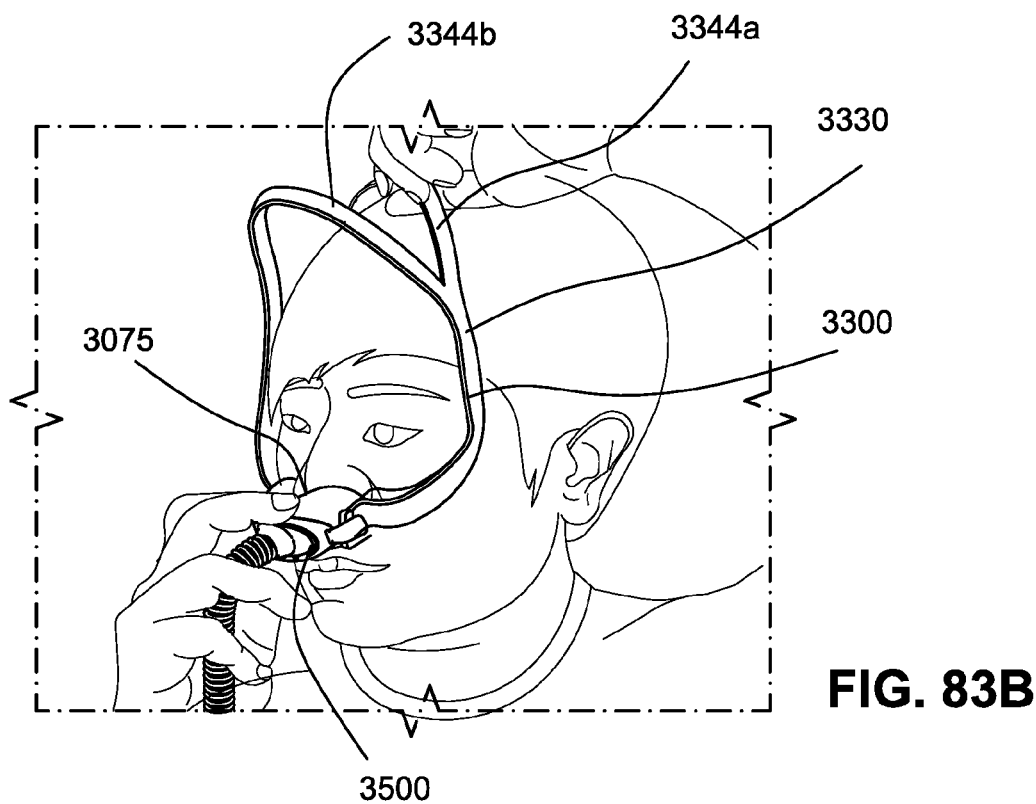
Figure 83C:
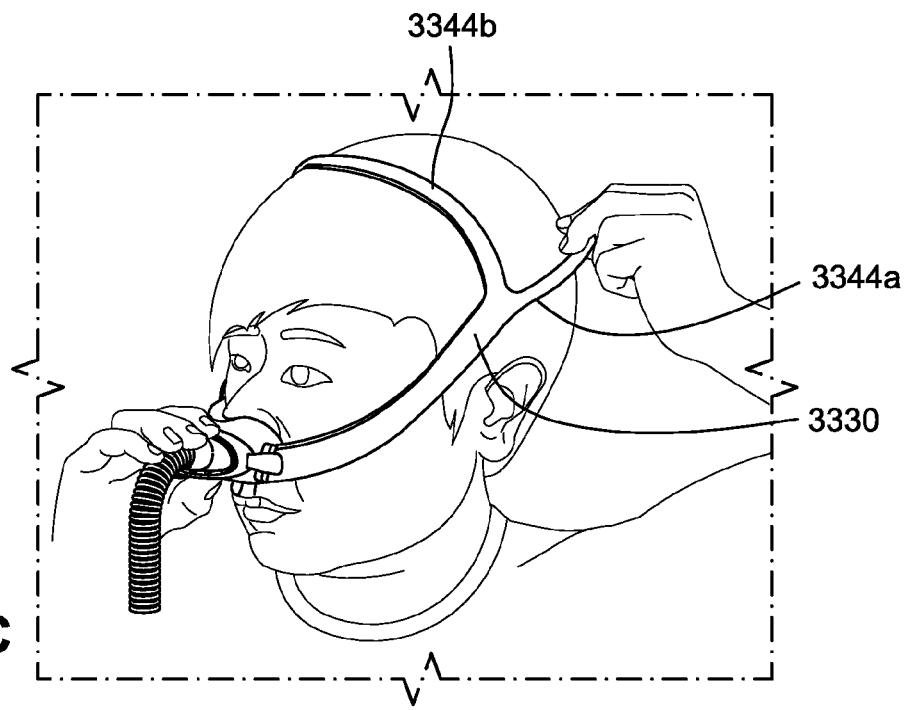
Figure 83D:
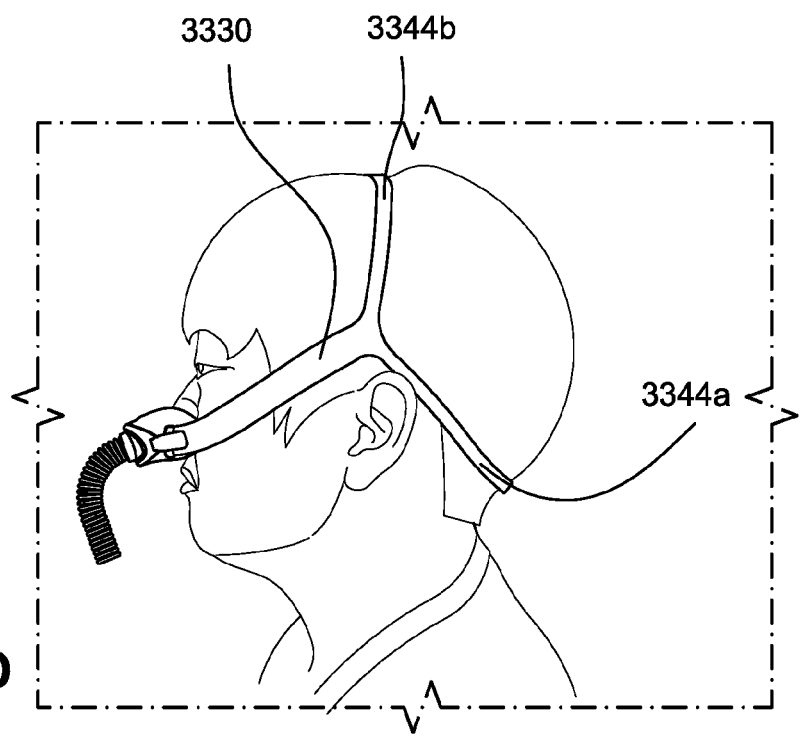

FIG. 83B shows the patient placing the cushion assembly 3075 and the seal-forming structure 3100 thereof under the patient's nose and ensuring that it sits comfortably against the patient's face. Such figure also shows the patient beginning to don the positioning and stabilising structure 3300, i.e., by pulling a lower one of the back strap portions 3344a with one hand while holding the frame assembly 3500/cushion assembly 3075 with the other hand to stretch the headgear strap assembly 3330 over the patient's head. FIGS. 83C and 83D show the headgear strap assembly 3330 stretched around the back of the patient's head to hold the patient interface 3000 against the patient's nose, e.g., with an upper one of the back strap portions 3344b sitting comfortably on top of the patient's head.

As illustrated, one of the split back strap portions 3344b is positioned superior to the patient's occipital lobe while the other of the split back strap portions 3344a is positioned inferior to the patient's occipital lobe, e.g., to cup the back of the patient's head for support and stability. However, it should be appreciated that the back strap portions 3344a, 3344b may be positioned in different positions along the back of the patient's head, e.g., to adjust tension or position for patient preference and/or comfort. For example, as shown in FIGS. 55 and 56, both back strap portions 3344a, 3344b may be positioned more adjacent to one another towards a top of the patient's head, e.g., both positioned generally superior to the patient's occipital lobe. FIGS. 84A and 84B are exemplary views showing adjustment of the split back strap portions 3344a, 3344b to achieve a comfortable fit, e.g., adjust the split back strap portions 3344a, 3344b by spreading them apart to loosen or draw them closer together to tighten.

If additional adjustment of the headgear strap assembly 3330 may be required, adjustment may be conducted via the buckle 3360 as described above. For example, the headgear strap assembly 3330 may be tightened by pulling the free end of the back strap portions 3344a, 3344b (e.g., via reinforcement portion or finger tab 3347) away from the buckle 3360 as shown in FIG. 86A. The headgear strap assembly 3330 may be loosened by gripping the strap portions on either side of the buckle 3360 and pulling as shown in FIG. 86B, or by pulling the buckle 3360 relative to the strap portions.

It should be appreciated that the headgear strap assembly 3330 may be assembled to the patient interface 3000 so that the buckle 3360 can be located on either the right-hand side of the patient's head or the left-hand side of the patient's head, e.g., depending on patient preference to facilitate adjustment while being worn. For example, it may be preferable for the buckle 3360 to be located on the right-hand side of the patient's head for a right-handed patient to facilitate right-handed adjustment of the buckle 3360 by the patient.

The patient interface 3000 is now fitted and ready for use, i.e., the short tube 4180 of the patient interface 3000 may be connected to the air circuit 4170 for delivery of pressurised gas from the air circuit 4170 to the patient interface 3000.

As shown in FIG. 85, the patient interface 3000 may be removed by pulling the frame assembly 3500/cushion assembly 3075 along with the back strap portions 3344a, 3344b up and over the patient's head.

5.3.7 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 2 or more holes, about 5 to about 50 holes, about 10 to about 40 holes, about 10 to about 20 holes, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

FIGS. 4-24 illustrate a vent 3400 according to an example of the present technology. In the illustrated example, the vent 3400 is provided to the frame assembly 3500, and the vent 3400 comprises diffusing members 3450, e.g., filter materials, along the vent flow path structured and arranged to diffuse the exhaust vent flow to produce less noise. The diffused vent flow also reduces or eliminates jetting to that vent flow will not jet onto the bed and/or a partner adjacent the patient interface.

As illustrated, the main body 3510 includes an interior surface 3512 (along the posterior side) adapted to be oriented towards the interior of the plenum chamber 3200 in use, i.e., the pressurizable volume, and an exterior surface 3514 (along the anterior side) adapted to be oriented towards atmosphere in use. A multi-hole vent arrangement 3515 is provided to the main body 3510 on each side of the cover connecting portion 3540. Each multi-hole vent arrangement 3515 includes a plurality of vent orifices 3516 extending through the main body 3510 from the interior surface 3512 to the exterior surface 3514 to allow gas to be discharged to atmosphere. The exterior surface 3514 forms a bottom of the recessed region 3550 in the anterior side of the main body 3510.

In the illustrated example, as best shown in FIGS. 21-22, each multi-hole vent arrangement 3515 is arranged in an arc or U-shape with the open end oriented towards the cover connecting portion 3540. A spacer 3518, e.g., U-shaped protrusion, is provided to the exterior surface 3514 and extends along the interior periphery of a respective multi-hole vent arrangement 3515 to support a respective diffusing member 3450. The spacer 3518 supports the diffusing member 3450 in spaced relation from the exterior surface 3514 and the outlet end of each of the vent orifices 3516, e.g., see FIG. 9.

Also, a plurality of ribs 3560 are provided along the outer perimeter of the recessed region 3550, which provides spaced ribs 3560 along the outer periphery of each multi-hole vent arrangement 3515. In the illustrated example, each of the spaced ribs 3560 along the outer periphery of each multi-hole vent arrangement 3515 includes a stepped configuration including a first, lower step 3561 and a second, upper step 3562.

In the illustrated example, the first, lower step 3561 of each of the spaced ribs 3560 is structured and arranged to support the outer edge of a respective diffusing member 3450. Accordingly, the spacer 3518 along with the first steps 3561 of the spaced ribs 3560 collectively form a raised platform to support the diffusing member 3450 in spaced relation from the exterior surface 3514 and the outlet end of each of the vent orifices 3516, e.g., to minimize noise. Also, such spacing or offset of the diffusing member 3450 from the outlet end of each of the vent orifices 3516 creates an air gap, which ensures that the vent orifices 3516 do not become occluded by the diffusing member 3450 at any time.

As noted above, the second, upper step 3562 of each of the spaced ribs 3560 is structured and arranged to provide a stop for the outer edge of the anterior wall 3585 when the cover 3580 is connected to the main body 3510. In an alternative example, the second, upper step 3562 of each of the spaced ribs may not be provided, e.g., see FIG. 58 which shows ribs 3560 each including only a first step 3561.

When the cover 3580 is connected to the main body 3510, the anterior wall 3585 is supported in spaced relation from the exterior surface 3514 or bottom of the recessed region 3550 to accommodate and retain the diffusing member 3450 between the anterior wall 3585 and the spacer 3518/first steps 3561, i.e., main body 3510 and cover 3580 form a casing or cartridge for the diffusing member 3450. Moreover, as described below, the outer edge or outer periphery of the anterior wall 3585 is spaced from the outer edge or periphery of the recessed region 3550, such spacing or gap between the anterior wall 3585 and the periphery of the recessed region 3550 forming a vent outlet 3420 of the vent 3400.

As illustrated, each diffusing member 3450 is arranged to cover the respective multi-hole vent arrangement 3515 so that flow exiting the vent orifices 3516 of the multi-hole vent arrangement 3515 flows into the diffusing member 3450. In an example, the diffusing member 3450 may be constructed of a porous material that allows gas to flow through the material but diffuses any jet or other flow formation exiting the vent orifices 3516, e.g., non-woven fibrous material, woven fibrous material. In an example, the diffusing member 3450 may comprise a diffusing material which may be similar to or the same as a filter material or filter media. In an example, the diffusing member 3450 may comprise a thickness of about 0.1-10 mm, e.g., 3-8 mm, 5-7 mm, 6-8 mm, e.g., 7 mm, however other suitable thicknesses are possible. In the illustrated example, the diffusing member 3450 comprises a single layer, however it should be appreciated that the diffusing member 3450 may comprise two or more layers, e.g., stacked layers, of similar or dissimilar diffusing materials.

In an example, the cover 3580 is removably connected to the main body 3510, e.g., to allow cleaning and/or replacement of the diffusing members 3450. Alternatively, the entire frame assembly 3500 may be replaced, rather than replace the individual diffusing members 3450.

The main body 3510 and the cover 3580 cooperate to form a diffusion section including a diffusion section inlet 3410 (i.e., the outlet end of each of the vent orifices 3516) and a diffusion section outlet 3420 (i.e., gap between the anterior wall 3585 and the periphery of the recessed region 3550), the diffusion section outlet 3420 corresponding to a vent outlet of the vent 3400. As illustrated, the spaced ribs 3560 are disposed within the diffusion section between the diffusion section inlet 3410 and the diffusion section outlet 3420 to divide vent flow around the perimeter of the frame assembly 3500.

In the illustrated example, the spaced ribs 3560 are arranged to support respective diffusing members 3450 as well as divide vent flow. In the illustrated example, additional ribs 3565 may be provided along superior and inferior sides of the cover connecting portion 3540. Such ribs 3565 cooperate with the ribs 3560 to divide vent flow, however such ribs 3565 are not arranged to support respective diffusing members 3450. In an alternative example, such ribs 3565 may not be provided.

Also, in an alternative example, one or more ribs may be provided to the cover 3580. For example, one or more ribs on the cover 3580 may cooperate with one or more ribs provided to the main body 3510 to divide vent flow. In another example, one or more ribs may be provided to the cover 3580 in lieu of ribs provided to the main body 3510 to divide vent flow.

In an example, the one or more ribs may comprise an integral one-piece construction with the main body 3510 and/or the one or more ribs may comprise an integral one-piece construction with the cover 3520, e.g., one or more ribs molded in one-piece with the main body 3510 and/or the cover 3520. In an alternative example, the one or more ribs may be formed separately from the main body 3510 and assembled to the main body 3510 in a separate process and/or the one or more ribs may be formed separately from the cover 3520 and assembled to the cover 3520 in a separate process, e.g., one or more ribs separately molded and individually assembled to the main body 3510 and/or the cover 3520. However, it should be appreciated that the one or more ribs may be provided to the vent in other suitable manners.

In the illustrated example (e.g., see FIG. 14), the spaced ribs 3560, 3565 act as flow dividers that establish spaced and separated vent flow paths V that divide or apportion exhaust vent flow around the periphery of the frame assembly 3500 throughout the therapeutic pressure. That is, the spaced ribs 3560, 3565 are positioned and oriented with respect to the diffusion section inlet 3410 and the diffusion section outlet 3420 to divide the turbulent kinetic energy at the diffusion section inlet 3410 (i.e., the outlet end of each of the vent orifices 3516) into segments to optimize exhaust vent flow and minimize noise. In an example, the spaced ribs 3560, 3565 may divide the turbulent kinetic energy into substantial equal segments so that the energy may be uniformly directed to the diffusion section outlet 3420, i.e., the vent outlet of the vent 3400. However, it should be appreciated that the spaced ribs 3560, 3565 may divide flow into unequal and/or equal segments.

It should be appreciated that the anterior wall 3585 forms a diffusion section outlet 3420, i.e., vent outlet of the vent 3400, that is spaced radially outwardly of the vent inlet 3517 of the vent 3400 (i.e., the inlet end of each of the vent orifices 3516) and the diffusion section inlet 3410 (i.e., the outlet end of each of the vent orifices 3516). That is, vent flow cannot flow straight through the vent orifices 3516 to the diffusion section outlet 3420, i.e., the vent outlet, and must flow at least in part radially from the vent inlet 3517 to the vent outlet 3420.

In use, the vent 3400 is provided to the patient interface 3000 to allow a flow of gas from an interior of the patient interface, e.g., the plenum chamber 3200, to an exterior of the patient interface 3000, e.g., to atmosphere. The vent 3400 is structured and arranged to provide a vent flow path that passes through the plurality of vent orifices 3516 of each multi-hole vent arrangement 3515 into the diffusion section, through respective diffusing members 3450, and then through divided vent flow paths V provided by the spaced ribs 3560, 3565 to the vent outlet 3420. In an example, all flow may not necessarily pass through the diffusing members 3450, e.g., at least some of the flow may bypass the diffusing members 3450 and flow directly from the vent orifices to the divided vent flow paths provided by the spaced ribs to the vent outlet 3420.

The vent 3400 is structured and arranged to improve diffusivity in vent flow to generate lower turbulent kinetic energy, and therefore lower noise, e.g., to improve patient sleep quality. Diffusivity at least partly depends on air flow through vent holes and along the vent flow path, and air velocity throughout the vent flow path. High air velocity has high turbulent kinetic energy, and turbulent kinetic energy is an indicator for noise.

In the illustrated example, the vent 3400 provides several features to generate the lower turbulent kinetic energy. For example, each multi-hole vent arrangement 3515 includes vent orifices 3516 structured and arranged to prevent cross flow and allow substantially even distribution of air flow volume into the diffusion section. The spacer 3518 and spaced ribs 3560 support the diffusing member 3450 in spaced relation the vent orifices 3516, e.g., to minimize noise and prevent occlusion by the diffusing member 3450. Further, the spaced ribs 3560, 3565 act as a flow separator to separate the exhaust flow for lower turbulent kinetic energy.

Aspects of the vent 3400 may be tuned or optimized to provide a desired flow-pressure curve within a therapeutic pressure range. In an example, one or more characteristics of aspects of the vent 3400 may be tuned, e.g., based on venting requirement, sound requirement, treatment requirement, etc.

For example, the shape, size, number, orientation, and spacing arrangement of the ribs 3560, 3565 may be optimized to regulate flow.

In an example, the number of ribs 3560, 3565 along the recessed region may change, e.g., as the size of the vent assembly changes and/or the number and size of the vent orifices changes. In an example, the spacing between ribs may be about 7-9 mm. In example, the frame assembly 3500 may include 5-30 ribs, however other suitable numbers of ribs are possible. For example, the frame assembly 3500 may include 10-20 ribs, 8-15 ribs. In an example, 3-15 ribs (e.g., 5-10 ribs) may be associated with each multi-hole vent arrangement 3515.

In an example, the ribs 3560, 3565 may extend in a generally orthogonal/tangential direction to the main body 3510 of the frame assembly 3500. For example, the ribs 3560, 3565 may extend in a generally orthogonal direction to a major face (e.g., exterior surface 3514) of the main body 3510. This orientation of the ribs may minimize any dead space in the vent, e.g., compared to the ribs being oriented at an acute angle to the main body 3510. This orientation of the ribs may also help the airflow to exit the vent outlet 3420 (i.e., gap between the anterior wall 3585 and the periphery of the recessed region) in a direction that is generally orthogonal to the general plane of the main body 3510, thereby directing the airflow away from the patient's face in use.

In an example, each of the ribs 3560, 3565 includes a generally small thickness, e.g., 1-2 mm, e.g., 1.2 mm. This smaller thickness maximizes the venting space of the air, e.g., by creating wider vent flow paths. However, other suitable thicknesses are possible.

In an example, the shape, size, orientation, and number of vent orifices 3516 for each multi-hole vent arrangement 3515 may be tuned. In an example, each vent orifice is generally circular and may have a diameter in the range of about 0.7-1.2 mm, e.g., 1 mm. In an example, each vent orifice may include a taper or draft angle, e.g., each vent orifice may decrease in diameter from the inlet end at the interior surface to the outlet end at the exterior surface. In the illustrated example, each multi-hole vent arrangement 3515 includes 8 orifices, however other suitable numbers of orifices are possible. For example, each multi-hole vent arrangement 3515 may include 2-30 orifices, e.g., 5-20 orifices, 5-10 orifices, 6-8 orifices.

In an example, the axis of the flow path through each of the vent orifices 3516 may be parallel or angled away from one another such that cross-flow is avoided to prevent generation of additional noise.

In an example, the size of the anterior wall 3585 may be tuned to adjust the size of the vent outlet 3420, i.e., gap between the anterior wall 3585 and the periphery of the recessed region).

In an example, the thickness, material, and shape of each diffusing member 3450 may be tuned. In an example, each diffusing member 3450 is shaped to cover the vent orifices 3516 of the respective multi-hole vent arrangement.

In an example, it should be appreciated that the tuning of one or more parameters may be implemented in conjunction with one or more other parameters of the vent 3400 to optimize diffusion and the reduction of turbulent kinetic energy to reduce noise. For example, certain ratios between parameters may be tuned to optimize diffusion. In an example, the size/number of ribs 3560, 3565 may be tuned in conjunction with the size/number of vent orifices 3516. For example, an exemplary ratio of the number of ribs to the number of orifices may be 0.5 to 1.0, e.g., 0.6 to 0.8, however other suitable ratios are possible. In another example, the size/number of ribs 3560, 3565 may be tuned in conjunction with overall dimensions of the patient interface 3000.

While the vent 3400 is described in relation to a nasal-cradle type patient interface, it should be appreciated that one or more aspects of the vent 3400 may be applicable to other types of patient interface, e.g., nasal, full-face, nasal prong type patient interfaces.

In an example, the frame assembly 3500 and vent 3400 thereof shown in FIGS. 4-24 may comprise a frame/vent arrangement for single-patient, multi-use (SPMU) applications, e.g., for home use. In an example, an alternative frame assembly may be provided to the patient interface for multi-patient, multi-use (MPMU) applications, e.g., for sleep lab or hospital uses.

FIGS. 76-82C illustrate a patient interface 6000 including a MPMU frame assembly 6500 according to an example of the present technology. In the illustrated example, the patient interface 6000 is substantially similar to patient interface 3000, but replaces frame assembly 3500 with frame assembly 6500 for MPMU applications. As illustrated, the frame assembly 6500 also functions as a central hub to which the cushion assembly 3075, the positioning and stabilizing structure 3300, and the short tube 4180 are connected, e.g., either in a removable fashion or a more permanent fashion.

In this example, the frame assembly 6500 is similar to frame assembly 3500 but comprises a different vent arrangement. As illustrated, the frame assembly 6500 includes a vent 6400 that does not include a diffusion section as in vent 3400, only a multi-hole vent arrangement 6515 provided to the main body 6510 on each side of the connection port 3600. Such frame assembly 6500 provides structure that may be more amenable to MPMU applications and requirements, e.g., facilitate cleaning/decontamination between uses, less parts, more rigid/durable to withstand repeated use.

Each multi-hole vent arrangement 6515 includes a plurality of vent orifices 6516 extending through the main body 6510 from the interior surface 6512 (adapted to be oriented towards the interior of the plenum chamber 3200 in use, i.e., the pressurizable volume) to the exterior surface 6514 (adapted to be oriented towards atmosphere in use) to allow gas to be discharged to atmosphere.

In the illustrated example, the vent orifices 6516 of each multi-hole vent arrangement 6515 may be arranged in columns. As illustrated in FIGS. 81, 82A, and 82B, the exterior surface 6514 of the main body may provide spaced-apart (e.g., and generally parallel) surface areas 6525 with a stepped layout, with the outlet end of vent orifices 6516 for each column arranged along a respective one of the surface areas 6525. That is, the exterior surface 6514 of the main body may include ridges or ribs 6524 that provide such stepped arrangement of surface areas 6525. In the illustrated example, the ridges 6524 are arranged on each side of the connection port 3600 such that the surface areas 6525 progressively step down away from the connection port 3600, e.g., elevation of the surface areas 6525 progressively decreases away from the connection port 3600. Such arrangement orients the axis of the flow path through each of the vent orifices 6516 to be parallel or angled away from one another such that cross-flow is avoided to prevent noise. In an example, the ridges or ribs 6524 may facilitate manufacturing (e.g., molding) of the frame assembly 6500 and vent 6400 thereof.

It should be appreciated each multi-hole vent arrangement 6515 may include any suitable number of columns, e.g., 2-10 columns, 3-5 columns, and each column may include any suitable number of vent orifices, e.g., 1-20 vent orifices, 2-10 orifices, 2-5 orifices. Also, it should be appreciated that each multi-hole vent arrangement 6515 may include vent orifices arranged in alternative manners, e.g., rows, radially, random.

The shape, size, orientation, and number of vent orifices 6516 for each multi-hole vent arrangement 6515 may be tuned. In an example, each vent orifice is generally circular and may have a diameter in the range of about 0.7-1.2 mm, e.g., 1 mm. In an example, each vent orifice may include a taper or draft angle, e.g., each vent orifice may decrease in diameter from the inlet end at the interior surface to the outlet end at the exterior surface. In the illustrated example, each multi-hole vent arrangement 6515 includes 18 orifices, however other suitable numbers of orifices are possible. For example, each multi-hole vent arrangement 6515 may include 2-40 orifices, e.g., 5-25 orifices, 10-20 orifices.

The short tube 4180 may be permanently or removably connected to the connection port 3600. In an example, as shown FIG. 82C, the short tube 4180 and the connection portion 3600 may include a snap or interference fit assembly, e.g., cuff 4185 of the short tube 4180 includes a peripheral groove 4186 adapted to engage a peripheral bead 3605 along the interior of the connection port 3600. However, it should be appreciated that the short tube 4180 may be connected to the connection port 3600 in other suitable manners, e.g., either in a removable fashion or a more permanent fashion.

Similar to frame assembly 3500, a pair of rigidizer arms 3302 of the positioning and stabilising structure 3300 are connected to respective sides of the frame assembly 6500 by a respective one of a pair of flexible joints 3305. The headgear strap assembly 3330 may be connected to the rigidiser arms 3302 as described above.

Also, the frame assembly 6500 comprises a cushion connecting portion 6530, similar to cushion connecting portion 3530 of frame assembly 3500, structured and arranged to releasably connect the cushion assembly 3075 to the frame assembly 6500 as described above.

5.3.8 Decoupling Structure(s)

In one form the patient interface 3000 includes at least one decoupling structure, for example, a swivel or a ball and socket.

5.3.9 Connection Port

Connection port 3600 allows for connection to the air circuit 4170.

5.3.10 Forehead Support

In one form, the patient interface 3000 includes a forehead support 3700. For example, FIG. 3A shows a non-invasive patient interface 3000 in accordance with one aspect of the present technology comprising a seal-forming structure 3100, a plenum chamber 3200, a positioning and stabilising structure 3300, a vent 3400, one form of connection port 3600 for connection to air circuit 4170, and a forehead support 3700.

5.3.11 Anti-Asphyxia Valve

In one form, the patient interface 3000 includes an anti-asphyxia valve.

5.3.12 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block of the RPT device 4000 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.4.1 Oxygen Delivery

In one form of the present technology, supplemental oxygen may be delivered to one or more points in the pneumatic path, such as upstream of the pneumatic block, to the air circuit 4170 and/or to the patient interface 3000.

5.5 Glossary

For the purposes of the present technology disclosure, in certain forms of the present technology, one or more of the following definitions may apply. In other forms of the present technology, alternative definitions may apply.

5.5.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.5.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.5.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.5.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.5.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.5.4 Anatomy
5.5.4.1 Anatomy of the Face

Ala: the external outer wall or "wing" of each nostril (plural: alar)

Alar angle:

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Lip, lower (labrale inferius):

Lip, upper (labrale superius):

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.5.4.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.5.4.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.5.5 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space:

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.5.6 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.5.6.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.5.6.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.5.6.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.5.6.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.6 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.7 Reference Signs List

| Feature Item | Number |
|---|---|
| patient | 1000 |
| bed partner | 1100 |
| patient interface | 3000 |
| cushion assembly | 3075 |
| naris openings | 3102 |
| bridge portion | 3104 |
| lateral support regions | 3108 |
| mid - lateral regions | 3110 |
| medial region | 3114 |
| thickened portion | 3120 |
| thickened portion | 3121 |
| thickened portion | 3122 |
| frame connection structure | 3150 |
| seal connecting portion | 3160 |
| frame connecting portion | 3170 |
| undercut | 3175 |
| recess | 3177 |
| cut-out | 3179 |
| plenum chamber | 3200 |
| chord | 3210 |
| superior point | 3220 |
| inferior point | 3230 |
| positioning and stabilising structure | 3300 |
| rigidizer arms | 3302 |
| flexible joints | 3305 |
| headgear strap assembly | 3330 |
| strap | 3340 |
| side strap portion | 3342 |
| button - hole | 3343 |
| back strap portion | 3344 |
| finger tab | 3345 |
| finger tab | 3347 |
| strap | 3350 |
| side strap portion | 3352 |
| button - hole | 3353 |
| finger tab | 3355 |
| buckle | 3360 |
| main body | 3362 |
| first end portion | 3364 |
| second end portion | 3366 |
| first opening | 3370 |
| surface | 3375 |
| cross - bar | 3380 |
| cross - bar | 3382 |
| base | 3390 |
| overmold | 3391 |
| vent | 3400 |
| diffusion section inlet | 3410 |
| diffusion section outlet/vent outlet | 3420 |
| diffusing members | 3450 |
| frame assembly | 3500 |
| main body | 3510 |
| recess | 3511 |
| interior surface | 3512 |
| exterior surface | 3514 |
| multi - hole vent arrangement | 3515 |
| vent orifices | 3516 |
| vent inlet | 3517 |
| spacer | 3518 |
| body portion | 3520 |
| cushion connecting portion | 3530 |
| undercut | 3535 |
| protrusion | 3537 |
| cover connecting portion | 3540 |
| bead | 3545 |
| recessed region | 3550 |

-continued

| Feature Item | Number |
|---|---|
| ribs | 3560 |
| first step | 3561 |
| second step | 3562 |
| ribs | 3565 |
| protrusion | 3577 |
| cover | 3580 |
| protrusion | 3581 |
| anterior wall | 3585 |
| tube portion | 3590 |
| groove | 3595 |
| connection port | 3600 |
| bead | 3605 |
| interfacing surface | 3615 |
| forehead support | 3700 |
| sealing lip | 3850 |
| RPT device | 4000 |
| air circuit | 4170 |
| short tube | 4180 |
| cuff | 4185 |
| groove | 4186 |
| humidifier | 5000 |
| back strap portion | 3344a |
| back strap portion | 3344b |
| opening | 3372a |
| opening | 3372b |
| patient interface | 6000 |
| vent | 6400 |
| frame assembly | 6500 |
| main body | 6510 |
| interior surface | 6512 |
| exterior surface | 6514 |
| multi-hole vent arrangement | 6515 |
| vent orifices | 6516 |
| ridge | 6524 |
| surface area | 6525 |
| cushion connecting portion | 6530 |

The invention claimed is:

1. A patient interface to deliver a flow of air at a positive pressure with respect to ambient air pressure to an entrance to the patient's airways including at least the entrance of a patient's nares while the patient is sleeping, to ameliorate sleep disordered breathing, the patient interface comprising:
   a frame assembly; and
   a cushion assembly configured to removably and repeatably connect to the frame assembly,
   wherein the frame assembly and the cushion assembly form at least part of a plenum chamber pressurizable to a therapeutic pressure,
   wherein the cushion assembly comprises a one-piece construction including a seal-forming structure constructed and arranged to form a seal with a region of a patient's face surrounding the entrance to the patient's airways and a frame connection structure constructed and arranged to removably and repeatably connect the cushion assembly to the frame assembly,
   wherein the seal-forming structure comprises a first elastomeric material and the frame connection structure comprise a second elastomeric material,
   wherein the first elastomeric material comprises a first Shore A durometer and the second elastomeric material comprises a second Shore A durometer,
   wherein the second Shore A durometer is higher than the first Shore A durometer,
   wherein the frame connection structure comprises an undercut that acts as an interface or catch adapted to connect to the frame assembly,
   wherein the frame connection structure is arranged along an interior surface or interior periphery of the seal-forming structure such that the frame connection structure and the undercut thereof is arranged or oriented towards an interior of the cushion assembly that forms at least a portion of the plenum chamber, wherein the cushion assembly further comprises a flexible sealing flap provided to the seal-forming structure and comprising the first elastomeric material, wherein the flexible sealing flap is configured and arranged to form a seal with the frame assembly when the cushion assembly is connected to the frame assembly, wherein the flexible sealing flap is arranged inward of the frame connection structure within the plenum chamber, and wherein the flexible sealing flap protrudes further from the interior periphery into the plenum chamber than the frame connection structure.

2. The patient interface according to claim 1, wherein the seal-forming structure comprises a nasal cradle cushion adapted to from a seal against at least an underside of the patient's nose.

3. The patient interface according to claim 1, wherein the seal-forming structure and the frame connection structure comprise an overmolded construction to form a one-piece integrated component.

4. The patient interface according to claim 3, wherein the frame connection structure comprises a base mold and the seal-forming structure comprises an overmold provided to the base mold.

5. The patient interface according to claim 1, wherein each of the first elastomeric material and the second elastomeric material comprises a TPE or silicone material.

6. The patient interface according to claim 1, wherein the frame connection structure comprises one or more interfacing surfaces structured to bond with the seal-forming structure.

7. The patient interface according to claim 1, wherein the first Shore A durometer is in the range of 30-50 Shore A and the second Shore A durometer is in the range of 60-90 Shore A.

8. The patient interface according to claim 1, wherein the frame assembly is relatively harder than the frame connection structure.

9. The patient interface according to claim 1, wherein the frame connection structure and the undercut thereof extend around the entire perimeter or interior periphery of the seal-forming structure.

10. The patient interface according to claim 1, wherein the frame connection structure comprises one or more interfacing surfaces configured to engage the interior surface of the seal-forming structure.

11. The patient interface according to claim 1, wherein the frame connection structure comprises a separate and distinct part from the seal-forming structure that is connected to the seal-forming structure to form the cushion assembly.

12. The patient interface according to claim 1, wherein the flexible sealing flap and the undercut of the frame connection structure form a space therebetween to receive a portion of the frame assembly.

13. The patient interface according to claim 12, wherein the frame assembly comprises a barbed end, wherein the undercut of the frame connection structure is configured and arranged to engage behind the barbed end when the cushion assembly is connected to the frame assembly, and wherein the barbed end forms the portion of the frame assembly such that the barbed end is received in the space between the flexible sealing flap and the undercut when the cushion assembly is connected to the frame assembly.

14. The patient interface according to claim 13, wherein the barbed end comprises a tapered or angled leading surface, and wherein the tapered or angled leading surface is configured to guide and facilitate outward deflection the frame connection structure over and behind the barbed end.

15. The patient interface according to claim 1, wherein the frame connection structure and the seal-forming structure comprise different surface finishes.

16. The patient interface according to claim 1, wherein the flexible sealing flap is configured and arranged to engage and resiliently deflect against the frame assembly to form the seal.

17. The patient interface according to claim 16, wherein the flexible sealing flap is configured and arranged such that, when the plenum chamber is pressurized to the therapeutic pressure, the flexible sealing flap is urged with greater force against the frame assembly to strengthen and increase sealing force between the flexible sealing flap and the frame assembly.

18. The patient interface according to claim 1, wherein the flexible sealing flap includes a length that varies along one or more portions of a perimeter of the seal-forming structure.

19. The patient interface according to claim 18, wherein the length of the flexible sealing flap at lateral sides of the seal-forming structure is longer than the length of the flexible sealing flap at superior and inferior sides of the seal-forming structure.

20. A CPAP system for providing gas at positive pressure for respiratory therapy to a patient, the CPAP system comprising:
an RPT device configured to supply a flow of gas at a therapeutic pressure;
a patient interface according to claim 1; and
an air delivery conduit configured to pass the flow of gas at the therapeutic pressure from the RPT device to the patient interface.

* * * * *